US012575895B2

(12) United States Patent　　　　(10) Patent No.:　US 12,575,895 B2
Mosadegh et al.　　　　　　　　　　(45) Date of Patent:　Mar. 17, 2026

(54) MIXED REALITY IMAGE GUIDANCE FOR MEDICAL INTERVENTIONS

(71) Applicant: Cornell University, Ithaca, NY (US)

(72) Inventors: Bobak Mosadegh, New York, NY (US); Matin Torabinia, New York, NY (US)

(73) Assignee: Cornell University, Ithaca, NY (US)

( * ) Notice: Subject to any disclaimer, the term of this patent is extended or adjusted under 35 U.S.C. 154(b) by 362 days.

(21) Appl. No.: 18/246,120

(22) PCT Filed: Sep. 22, 2021

(86) PCT No.: PCT/US2021/051500

§ 371 (c)(1),
(2) Date: Mar. 21, 2023

(87) PCT Pub. No.: WO2022/066730

PCT Pub. Date: Mar. 31, 2022

(65) Prior Publication Data

US 2023/0363832 A1　　Nov. 16, 2023

Related U.S. Application Data

(60) Provisional application No. 63/082,450, filed on Sep. 23, 2020.

(51) Int. Cl.
　*A61B 34/20*　　　(2016.01)
　*A61B 34/10*　　　(2016.01)
　*G06T 7/33*　　　(2017.01)
(52) U.S. Cl.
　CPC ............. *A61B 34/20* (2016.02); *A61B 34/10* (2016.02); *G06T 7/344* (2017.01);
　　　　　　(Continued)

(58) Field of Classification Search
None
See application file for complete search history.

(56) References Cited

U.S. PATENT DOCUMENTS 8,706,185 B2　4/2014　Foley et al.
9,104,902 B2　8/2015　Xu et al.
　　　　　　(Continued)

FOREIGN PATENT DOCUMENTS

WO　　WO-2019165430 A1 *　8/2019　............. A61B 34/10

OTHER PUBLICATIONS

Buther, et al. "List mode-driven cardiac and respiratory gating in PET" J Nucl Med. 2009;50(5):674-81. Epub Apr. 18, 2009. doi: 10.2967/jnumed.108.059204. PubMed PMID: 19372491 (Year: 2009).
　　　　　　(Continued)

*Primary Examiner* — Miya J Cato
(74) *Attorney, Agent, or Firm* — Foley & Lardner LLP

(57)　　　　　ABSTRACT

Disclosed are approaches that may provide image-guidance to interventionalists by providing true 3D visualization and quantitative feedback in real-time. A guidance system may allow a physician to manipulate a medical device and see a 3D rendering with quantitative feedback floating in mixed reality, next to standard monitors. Image tracking may detect and co-register the medical device's 3D position using, for example, bi-plane C-arm X-ray fluoroscopy and provide a 3D trajectory as quantitative feedback. Patterns in a fluoroscopic image may be used to accurately determine an object's z-position from a single angle projection.

20 Claims, 48 Drawing Sheets

(52) U.S. Cl.
CPC ... *A61B 2034/104* (2016.02); *A61B 2034/105* (2016.02); *G06T 2207/10121* (2013.01)

(56) References Cited

U.S. PATENT DOCUMENTS

| | | | |
|---|---|---|---|
| 2014/0031668 A1 | 1/2014 | Mobasser et al. | |
| 2015/0223773 A1 | 8/2015 | John et al. | |
| 2020/0268469 A1* | 8/2020 | Wolf .................... | A61B 5/7275 |
| 2020/0405397 A1 | 12/2020 | Liu et al. | |
| 2021/0090344 A1 | 3/2021 | Geri et al. | |
| 2021/0113293 A9 | 4/2021 | Silva et al. | |
| 2021/0236209 A1 | 8/2021 | Black et al. | |
| 2021/0289188 A1 | 9/2021 | Casas | |
| 2022/0160430 A1* | 5/2022 | Landon .................. | A61B 90/36 |
| 2022/0202493 A1* | 6/2022 | Gibby .................... | A61B 34/10 |
| 2023/0071306 A1* | 3/2023 | Miller .................. | A61B 5/6852 |
| 2023/0172600 A1* | 6/2023 | Dumpe .................. | A61B 34/20 |
| | | | 606/90 |

OTHER PUBLICATIONS

Desjardins, et al. "ECG-gated cardiac CT" AJR Am J Roentgenol. 2004; 182( 4):993-1010. Epub Mar. 25, 2004. doi: 10.2214/ajr.182. 4.1820993. PubMed PMID: 15039178 (Year: 2004).

Fallavollita, Pascal. "Is single-view fluoroscopy sufficient in guiding cardiac ablation procedures?" Int J Biomed Imaging. 2010; 2010:631264. doi: 10.1155/2010/631264. PubMed PMID: 20368770; PMCID: PMC2846336. (Year: 2010).

International Preliminary Report on Patentability in PCT PCT/US2021/051500 Dtd Mar. 28, 2023.

International Search Report and Written Opinion on PCT PCT/US2021/051500 dated Dec. 27, 2021.

Jang, et al. "Development of a Hybrid Training Simulator for Structural Heart Disease Interventions" Advanced Intelligent Systems. 2020;2(12):2000109 (Year: 2020).

Koivumaki, et al. "An integrated bioimpedance—ECG gating technique for respiratory and cardiac motion compensation in cardiac PET" Phys Med Biol. 2014;59(21):6373-85. Epub Oct. 9, 2014. doi: 10.1088/003 I-9155/59/21/6373. PubMed PMID: 25295531 (Year: 2014).

Linte et al. "On mixed reality environments for minimally invasive therapy guidance: Systems architecture, successes and challenges in their implementation from laboratory to clinic" Computerized Medical Imaging and Graphics (CMIG 2013), vol. 37, No. 2, pp. 83-97 (Year: 2013).

Liu et al. "An augmented reality system for image guidance of transcatheter procedures for structural heart disease" PLOS ONE. 2019; 14(7):e0219174. doi: 10.1371/journal.pone.0219174 (Year: 2019).

Ronneberger, et al. "U-net: Convolutional networks for biomedical image segmentation" International Conference on Medical image computing and computer-assisted intervention; 2015: Springer (Year: 2015).

Sra et al. "Identifying the third dimension in 2D fluoroscopy to create 3D cardiac maps" JCI Insight. 2016; 1(21):e90453. doi: 10.1172/jci.insight.90453. PubMed PMID: 28018976; PMCID: PMC5161213 (Year: 2016).

Torabinia et al. "Deep learning-driven catheter tracking from bi-plane X-ray fluoroscopy of 3D printed heart phantoms" Mini-invasive Surgery, 5 (Year: 2021).

Vernikouskaya et al. "Patient-specific registration of 3D CT angiography (CTA) with X-ray fluoroscopy for image fusion during transcatheter aortic valve implantation (TAVI) increases performance of the procedure" Clinical Research in Cardiology, vol. 107, No. 6, pp. 507-516 (Year: 2018).

\* cited by examiner

STANDARD
2D FLUORO

MIXED REALITY
DISPLAY

Position
x: -1.0
y: -2.0
z: -6.0
θ: -45 deg

PHYSICIAN
UPDATES CATHETER
POSITION &
ACQUIRES NEW
FLUORO IMAGE

SOFTWARE
CO-REGISTERS
CATHETER FROM
FLUORO WITH HEART
FROM CT

QUANTITATIVE FEEDBACK

Figure 12:
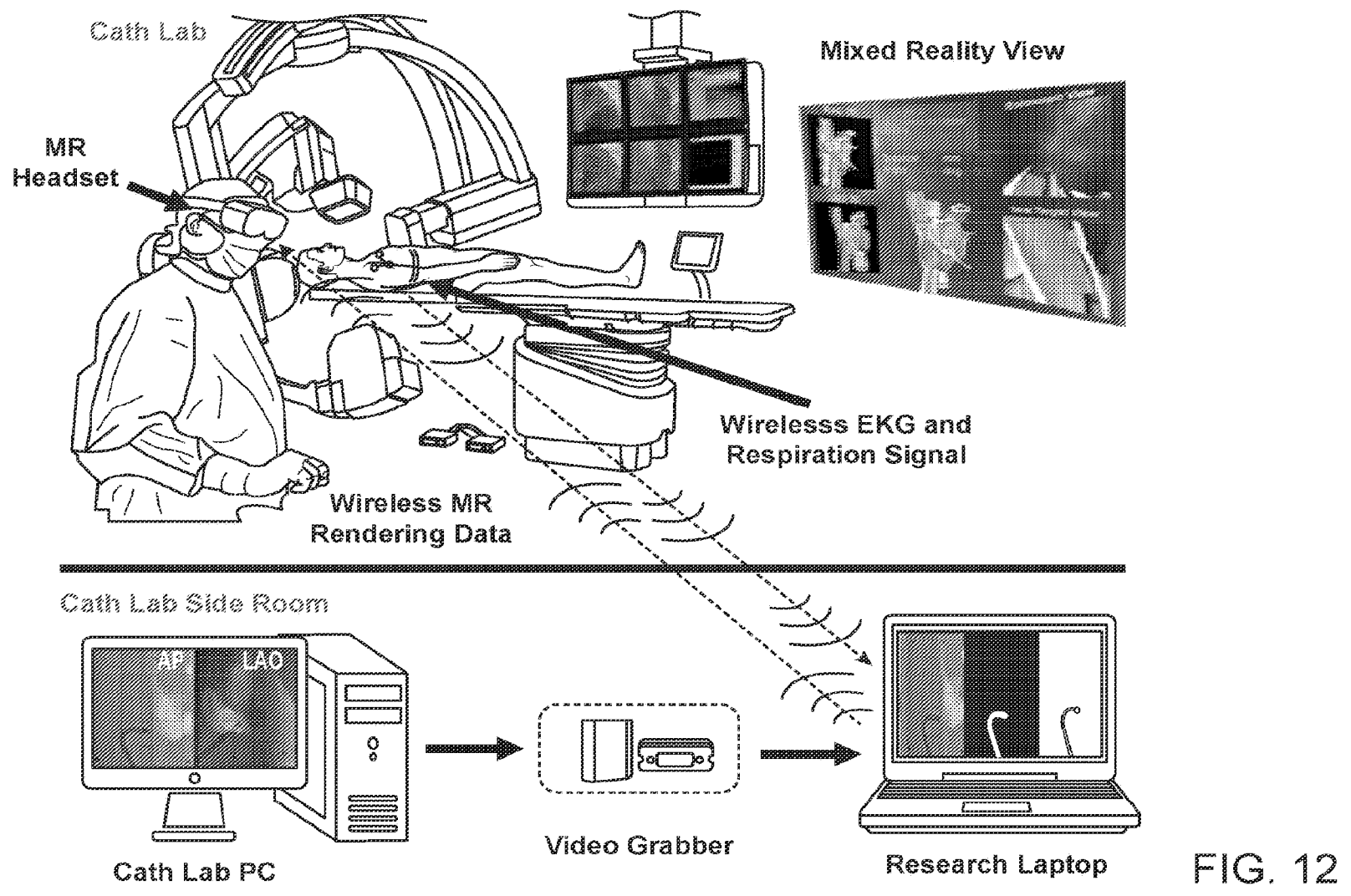

Mixed Reality View

Wirelesss EKG and Respiration Signal

Wireless MR Rendering Data

Cath Lab

MR Headset

Cath Lab Side Room

Cath Lab PC

Video Grabber

Research Laptop

(B) Patient-specific 3D printed model

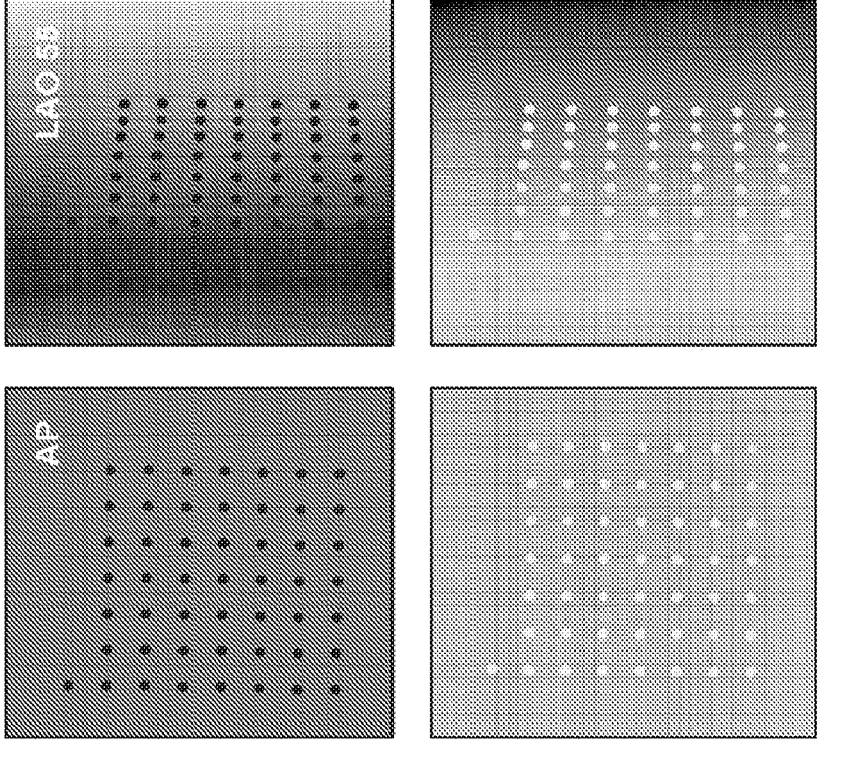
FIG. 14B
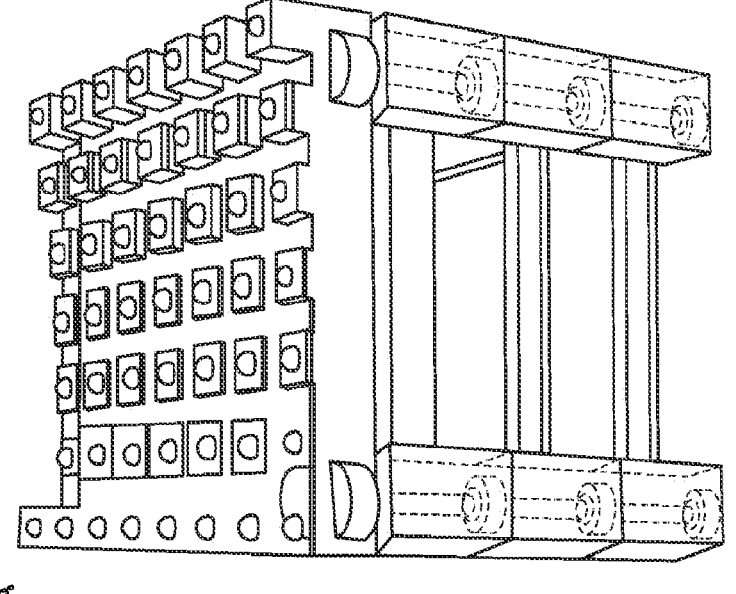
FIG. 14A (B) Segmentation output (A) Fluoroscopic Image (D) Detection of POI (C) Post processing

(A) Bi-plane Imaging for calculating Ground Truth Z

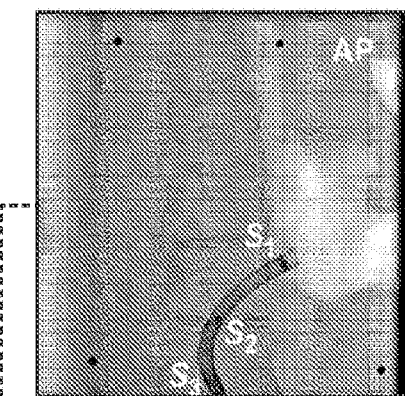 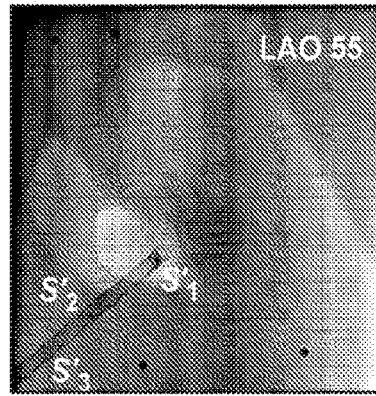

(B) Equation to solve for $z$ and $z'$ from bi-plane images

$$S = \begin{bmatrix} x \\ y \\ z \end{bmatrix} = T_{3d} \cdot S' = \begin{bmatrix} \cos\theta & 0 & \sin\theta \\ 0 & 1 & 0 \\ -\sin\theta & 0 & \cos\theta \end{bmatrix} \begin{bmatrix} x' \\ y' \\ z' \end{bmatrix}$$

(C) Detected Ground Truth values for catheter positions

$$S_1 = \begin{bmatrix} x_1 \\ y_1 \\ z_1 \end{bmatrix} \qquad S_2 = \begin{bmatrix} x_2 \\ y_2 \\ z_2 \end{bmatrix} \qquad S_3 = \begin{bmatrix} x_3 \\ y_3 \\ z_3 \end{bmatrix}$$

(D) CNN Regression

(E) CNN outputs 3D coordinates of catheter

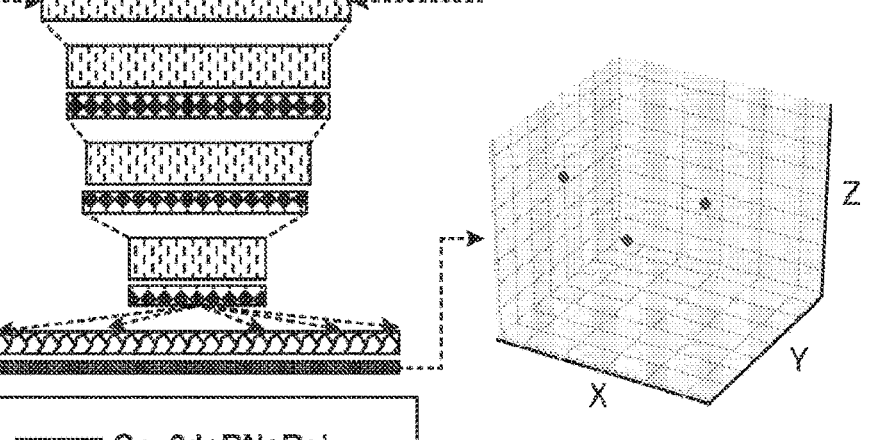

Cnv2d+BN+ReLu
Max pooling
Fully connected
Regression

FIG. 16

Inhale

Exhale

(A) Acquisition of CT scan at 2 respiratory phases coupled with chest measurement with respiratory transducer
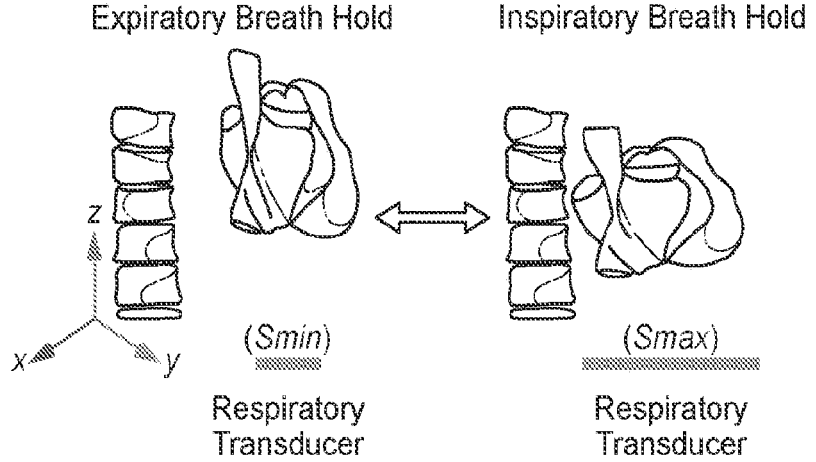
Expiratory Breath Hold                    Inspiratory Breath Hold
$(Smin)$                                          $(Smax)$
Respiratory                                    Respiratory
Transducer                                     Transducer
(B) Physician specifies target point for each respiratory phase
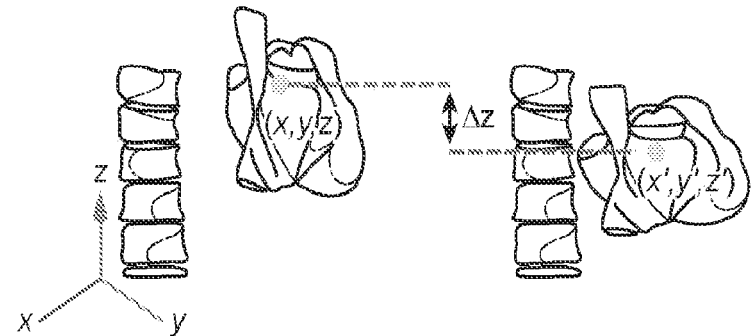
(C) Interpolation of respiration sensor
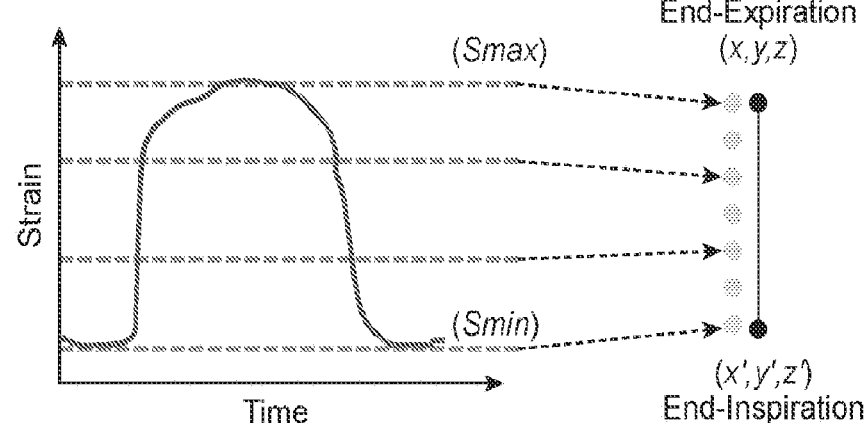
FIG. 18

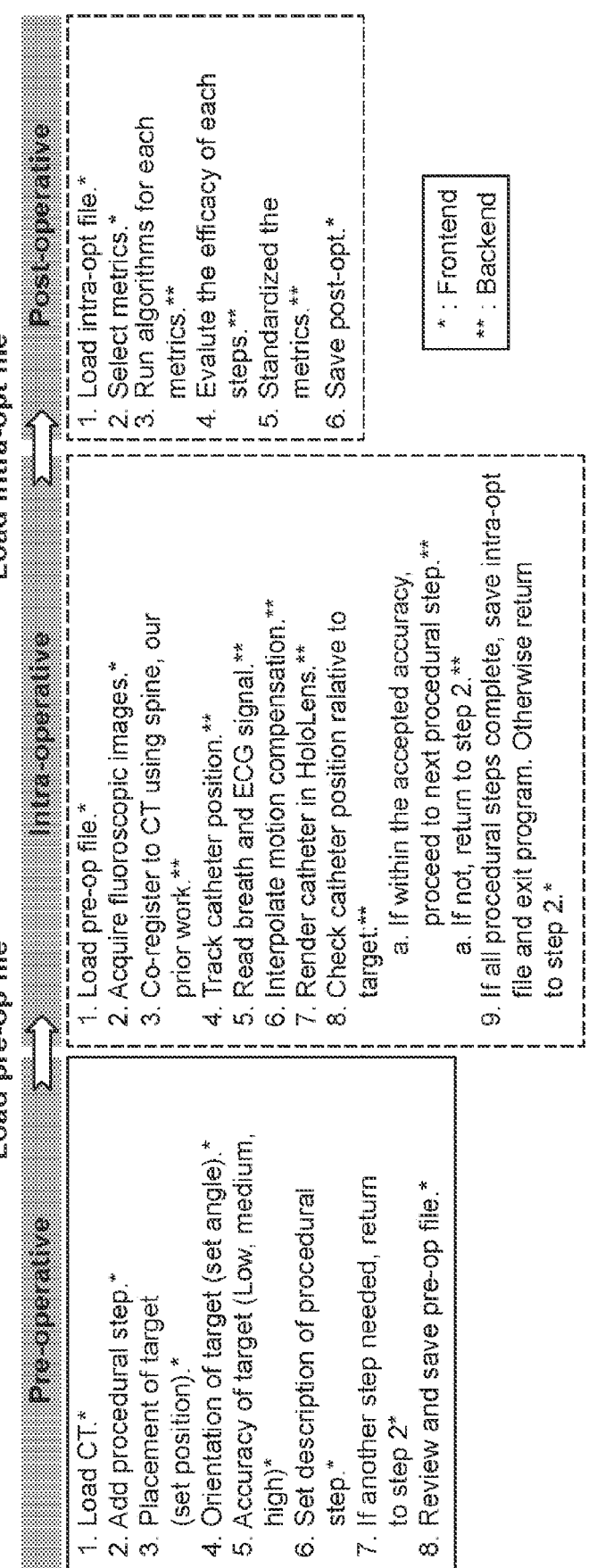

Load pre-op file     Load intra-opt file

Pre-operative

1. Load CT.*
2. Add procedural step.*
3. Placement of target (set position).*
4. Orientation of target (set angle).*
5. Accuracy of target (Low, medium, high)*
6. Set description of procedural step.*
7. If another step needed, return to step 2*
8. Review and save pre-op file.*

Intra-operative

1. Load pre-op file.*
2. Acquire fluoroscopic images.*
3. Co-register to CT using spine, our prior work.**
4. Track catheter position.**
5. Read breath and ECG signal.**
6. Interpolate motion compensation.**
7. Render catheter in HoloLens.**
8. Check catheter position relative to target.**
   a. If within the accepted accuracy, proceed to next procedural step.**
   a. If not, return to step 2.**
9. If all procedural steps complete, save intra-opt file and exit program. Otherwise return to step 2.*

Post-operative

1. Load intra-opt file.*
2. Select metrics.*
3. Run algorithms for each metrics.**
4. Evaluate the efficacy of each steps.**
5. Standardized the metrics.**
6. Save post-opt.*

* : Frontend
** : Backend

FIG. 20

(C) Inference test for Model A (A) Model Optimization (B) Spatial distribution Effect (C) Inference test for Model B (A) Model Optimization (B) Spatial distribution Effect (C) Inference test for Model C

| Hyperparameter | Learning rate | Batch size | Epochs number | Augmentation | Total size |
|---|---|---|---|---|---|
| Set #1 | 1e-3 | 32 | 80 | False | 529 images |
| Set #2 | 1e-3 | 32 | 110 | False | 529 images |
| Set #3 | 7e-4 | 32 | 250 | True* | 1058 images |

FIG. 26A

| Hyperparameter | Learning rate | Batch size | Epochs number | Augmentation | Total size |
|---|---|---|---|---|---|
| Set #1 | 5e-4 | 32 | 190 | True * (2x) | 1058 images |
| Set #2 | 7e-4 | 32 | 200 | True * (3x) | 1587 images |
| Set #3 | 7e-4 | 32 | 200 | 10-fold** | 2116 images |
| Set #4 | 7e-4 | 32 | 250 | True * (4x) | 2116 images |

FIG. 26B

| Hyperparameter | Learning rate | Batch size | Epochs number | Augmentation | Total size |
|---|---|---|---|---|---|
| Set #1 | 1e-2, decay=1e-3, rate=0.9 | 32 | 150 | True *(6x) | 3408 images |
| Set #2 | 1e-2, decay=1e-3, rate=0.9 | 32 | 200 | True *(6x) | 3408 images |
| Set #3 | 1e-2, decay=1e-5, rate=0.3 | 32 | 200 | True *(6x) | 3408 images |

FIG. 26C

MIXED REALITY IMAGE GUIDANCE FOR MEDICAL INTERVENTIONS

CROSS-REFERENCES TO RELATED APPLICATIONS

This application is a U.S. National Phase Application under 35 U.S.C. § 371 of International Application No. PCT/US2021/051500, filed on Sep. 22, 2021, which claims the benefit of and priority to U.S. Provisional Patent Application No. 63/082,450, entitled "Mixed Reality Image Guidance For Cardiac Interventions," filed Sep. 23, 2020, the contents of which are hereby incorporated by reference in their entireties.

BACKGROUND

Procedures utilizing an intra-cardiac catheter have become more prevalent as advances in transcatheter devices for structural heart diseases continue to develop. Procedures that have become particularly popular are transcatheter aortic valve replacement for aortic stenosis, use of MitraClip for mitral valve repair, left atrial ablations and left atrial appendage occlusion for patients with atrial fibrillation. Since these procedures are complex and relatively new, often these procedures are only done in specialized centers, by highly skilled experts. Furthermore, there is growing evidence that the success of these interventions are correlated with the proper position and angle of the catheter during the procedure. Thus, tools that can better guide, instruct, and/or train the interventionalist to perform these and other medical procedures will result in higher success rates and lower complications, such as perforations and iatrogenic septal defects.

Currently, pre-procedural planning consists of analyzing images acquired prior to a procedure to evaluate anatomic structure and dimensions. This information is used to determine a viable path of delivery for the device, select a device size, and assess approach angles for it. Although pre-procedural planning can help determine the feasibility of a medical procedure, it provides little insight as to how the procedure is being performed in real time. Ideally, real-time imaging would provide quantitative metrics for the accuracy of the approach angle and position of one or more medical devices (e.g., a catheter) during deployment. This real-time feedback would allow the interventionalist to make adjustments, as needed, prior to each step of the procedure. Furthermore, such data could serve as a basis for establishing effective standardized metrics for specific steps of an intervention, allowing researchers to study their correlation to effective clinical outcomes.

With a growing geriatric population estimated to triple by 2050, minimally invasive procedures that are image-guided are becoming both more popular and necessary for treating a variety of diseases. For example, more than 60 million Americans are currently estimated to have a structural heart defect, and more than a million of them will have a cardiac intervention every year. Unfortunately, these (and other medical) procedures can still result in death, or life-threatening complications, due to accidental punctures and device embolization, or can have limited efficacy due to misalignment of an implanted device.

SUMMARY

An overall goal of various embodiments of the disclosed approach is to provide the next generation of image-guidance and/or medical device navigation to clinicians (e.g., physicians) or other interventionalists by providing true 3D visualization and quantitative feedback in real-time. The impact of various embodiments of this approach will be derived from the integration of these technologies into clinical workflows of clinicians. Furthermore, various embodiments may comprise an open-source system that is compatible with a variety of imaging equipment, allowing the disclosed approach to be readily adoptable by, for example, catheterization labs and medical device companies.

In various embodiments, real-time imaging, such as fluoroscopy, provides visual feedback to the interventionalist for procedures, such as for catheter guidance, but the heart or other organ itself may be transparent and the catheter or other medical device is only seen as a 2D projection (see, e.g., FIG. 3A). Thus, an interventionalist is required, for example, to navigate a catheter within the heart without seeing it or any of the structures within it, or knowing the 3D orientation of the catheter. Technologies like rotational angiography, which act similar to a CT scan, can produce 3D images during the procedure, but expose patients to excess radiation and lack the ability to provide real-time time feedback. Alternatively, fusion imaging allows for 3D imaging data of the heart tissue to be overlaid on a fluoroscopic image; but this technology has the drawback that the catheter and rendered tissue is still only seen as a 2D projection, providing little navigational instruction (see, e.g., FIG. 3B). Various embodiments of the disclosed approach, therefore, provide a new method of visualizing a catheter and/or other medical devices within the patient's heart and/or other organ by using a mixed reality (MR) headset that provides a true 3D rendering with depth perception. A major advantage of various embodiments is that 3D tracking of a medical device from a single fluoroscopic plane employs machine learning methods. In various embodiments, this guidance system will provide real-time quantitative feedback with single-millimeter accuracy, and provide performance analytics compared to pre-procedural planning (see, e.g., FIG. 3C).

MR headsets, and similar augmented reality systems, can provide digital enhancement to our vision based on pre-procedural and intra-procedural images. Since these systems can provide true 3D renderings, with depth perception, that can be placed anywhere in a laboratory (e.g., a catheterization lab), there is little or no risk of interfering with the visualization of the original 2D fluoroscopic image (see, e.g., FIG. 4). Despite these advantages, there has been little adoption of MR into clinical interventions due to limitations in hardware, lack of streamlined methods to generate 3D data for rendering in a MR environment, and an inability to provide real-time analytics of the procedures. Embodiments of the disclosed approach employ hardware and new techniques in machine learning in fully interactive systems and methods that can provide quantitative feedback based on pre-operative and intra-operative imaging and planning.

Although this disclosure discusses heart procedures as illustrative examples which can employ embodiments of methods and systems discussed herein, the disclosed approach can, in various embodiments, be applied to any other organ and/or tissue, including but not limited to the lungs, brain, liver, kidney, prostate, and/or uterus.

In certain aspects, various embodiments relate to a method of providing real-time image guidance and/or navigation for a medical procedure. The method may comprise: receiving a first image data set of an anatomical target in relation to at least one fiducial marker in a selected coordinate system; generating a 3D model of the anatomical target, in relation to the first image data set and the at least one fiducial marker, in the selected coordinate system; receiving at least one fluoroscopic image comprising the at least one fiducial marker and a medical device; generating a mask and/or a center coordinate of the at least one fiducial marker from the at least one fluoroscopic image; generating a 3D model of the medical device from the at least one fluoroscopic image in the selected coordinate system using a trained deep learning model to perform feature extraction of the medical device and the at least one fiducial marker and to determine a z-position of at least one portion of the medical device within the selected coordinate system; registering the 3D model of the medical device with the 3D model of the anatomical target in the selected coordinate system; and generating a real-time output image comprising the 3D model of the medical device registered with a geometry of the anatomical target in the selected coordinate system.

In various embodiments, the at least one fluoroscopic image comprises at least one single-plane fluoroscopic image. In various embodiments, every fluoroscopic image in the at least one fluoroscopic image is a single-plane fluoroscopic image.

In various embodiments, the first image data set may comprise preoperative images, images acquired during the medical procedure, or images acquired both preoperatively and during the medical procedure.

In various embodiments, the at least one fiducial marker may be stationary. In various embodiments, the at least one fiducial marker may be at least substantially stationary.

In various embodiments, the at least one fiducial marker is visible in both the act of receiving the first image data set of the anatomical target and the act of receiving the at least one fluoroscopic image comprising the medical device.

In various embodiments, the first image data may comprise fluoroscopy data and/or echocardiography data.

In various embodiments, the at least one fiducial marker may be (wholly or partially) internal to a subject. In various embodiments, the at least one fiducial marker may be (wholly or partially) external to the subject.

In various embodiments, the at least one fiducial marker may comprise a plurality of fiducial markers.

In various embodiments, the at least one fiducial marker may comprise at least one first fiducial marker (wholly or partially) internal to the subject and at least one second fiducial marker (wholly or partially) external to the subject.

In various embodiments, the at least one fiducial marker may comprise a synthetic radiopaque material.

In various embodiments, the at least one fiducial marker may comprise the spine.

In various embodiments, feature extraction may comprise edge detection and/or a radiographic feature around the feature.

In various embodiments, the feature extraction may comprise edge detection of a dimension of at least a portion of the medical device. In various embodiments, the feature extraction may comprise edge detection of a dimension of a fiducial marker borne by the medical device. In various embodiments, the feature extraction may comprise edge detection of a rotational position of at least a portion of the medical device. In various embodiments, the feature extraction may comprise edge detection of a rotational position of the fiducial marker borne by the medical device relative to one or more axes. In various embodiments, the feature extraction may comprise a combination of two or more, or all, of edge detection of a dimension of at least a portion of the medical device, edge detection of a dimension of a fiducial marker borne by the medical device, edge detection of a rotational position of at least a portion of the medical device, and/or edge detection of a rotational position of the fiducial marker borne by the medical device relative to one or more axes.

In various embodiments, the first image data set may comprise computed tomography (CT) images and/or magnetic resonance (MR) images.

In various embodiments, the medical device may be a catheter.

In various embodiments, the catheter may comprise a radiopaque marker.

In various embodiments, the generating a 3D model of the medical device from the at least one fluoroscopic image in the selected coordinate system using the trained deep learning model to perform feature extraction of the medical device and the at least one fiducial marker and to determine a z-position of at least one portion of the medical device within the selected coordinate system comprises determining at least one of a rotation angle, a translation, and/or a scaling factor based on a projection of the radiopaque marker in the at least one fluoroscopic image.

In various embodiments, the method may further comprise outputting a haptic output to a haptic device responsive to a predefined proximity of at least a portion of the 3D model of the medical device to a predetermined portion of the 3D model of the anatomical target in the selected coordinate system.

In various embodiments, the registering of the 3D model of the medical device with the 3D model of the anatomical target in the selected coordinate system may comprise registering respiratory motion, cardiac motion, or both respiratory motion and cardiac motion.

In various embodiments, the registering of the respiratory motion, cardiac motion, or both respiratory motion and cardiac motion may comprise processing image data, as between the first image data set and the received at least one fluoroscopic image, having a same phase of motion.

In various embodiments, the method may further comprise outputting the real-time output image comprising the 3D model of the medical device registered with the geometry of the anatomical target in the selected coordinate system to a display device.

In various embodiments, the display device may comprises a virtual reality (VR) headset, an augmented reality (AR) headset, a mixed reality (MR) headset, a wearable device comprising a heads-up-display, and/or an area display.

In various embodiments, the anatomical target is an organ and/or a tissue. In various embodiments, the anatomical target comprises an organ or a tissue. In various embodiments, the anatomical target is the heart. In various embodiments, the anatomical target comprises the heart.

In various embodiments, the generating of the real-time output image comprising the 3D model of the medical device registered with the geometry of the anatomical target in the selected coordinate system may yield quantitative feedback of z-axis position of at least a portion of the medical device relative to the anatomical target or another anatomical feature with an accuracy ranging from 0.1 millimeter (mm) to 5 mm and a precision of about 10 microns (μm) to 1 mm.

In various embodiments, the quantitative feedback of z-axis position of the at least a portion of the medical device relative to the anatomical target or another anatomical feature is output to a device providing auditory, visual and/or tactile guidance for open-loop instruction to a interventionalist.

In various embodiments, the quantitative feedback of z-axis position of the at least a portion of the medical device relative to the anatomical target or another anatomical feature may be output as a closed-loop instruction to a robotic controller of the medical device.

In certain other aspects, various embodiments relate to a system for image guidance comprising: one or more processors; a non-transitory memory device storing processor executable instructions to cause the one or more processors, upon execution of the executable instructions, to: receive a first image data set of an anatomical target in relation to at least one fiducial marker in a selected coordinate system; generate a 3D model of the anatomical target, in relation to the first image data set and the at least one fiducial marker, in the selected coordinate system; receive at least one fluoroscopic image comprising the at least one fiducial marker and a medical device; generate a mask and/or a center coordinate of the at least one fiducial marker from the at least one fluoroscopic image; generate a 3D model of the medical device from the at least one fluoroscopic image in the selected coordinate system using a trained deep learning model stored on the non-transitory memory device, or stored on one or more other non-transitory memory devices, to perform feature extraction of the medical device and the at least one fiducial marker and to determine a z-position of at least one portion of the medical device within the selected coordinate system; register the 3D model of the medical device with the 3D model of the anatomical target in the selected coordinate system; and generate a real-time output image comprising the 3D model of the medical device registered with the geometry of the anatomical target in the selected coordinate system.

In various embodiments, the at least one fluoroscopic image comprises at least one single-plane fluoroscopic image. In various embodiments, every fluoroscopic image in the at least one fluoroscopic image is a single-plane fluoroscopic image.

In various embodiments, the first image data set may comprises preoperative images, images acquired during the medical procedure, or images acquired both preoperatively and during the medical procedure.

In various embodiments, the at least one fiducial marker may be stationary or at least substantially stationary.

In various embodiments, the at least one fiducial marker may be visible in both the act of receiving the first image data set of an anatomical target and the act of receiving the at least one fluoroscopic image comprising the medical device.

In various embodiments, the first image data may comprise fluoroscopy data and/or echocardiography data.

In various embodiments, the at least one fiducial marker may be internal to a subject or is external to the subject.

In various embodiments, the at least one fiducial marker may comprise a plurality of fiducial markers.

In various embodiments, the at least one fiducial marker may comprise at least one first fiducial marker internal to the subject and at least one second fiducial marker external to the subject.

In various embodiments, the at least one fiducial marker may comprise a synthetic radiopaque material.

In various embodiments, the at least one fiducial marker may comprise the spine.

In various embodiments, the feature extraction may comprise edge detection.

In various embodiments, the feature extraction may comprise detection of a dimension of at least a portion of the medical device, a dimension of a fiducial marker borne by the medical device, a rotational position of at least a portion of the medical device, and/or a rotational position of the fiducial marker borne by the medical device relative to one or more axes.

In various embodiments, the first image data set may comprise computed tomography (CT) images and/or magnetic resonance (MR) images.

In various embodiments, the system may further comprise the medical device.

In various embodiments, the medical device may comprise a catheter. In various embodiments, the medical device may comprise a catheter with a radiopaque marker.

In various embodiments, the executable instructions stored on the non-transitory memory device may cause the one or more processors, upon execution of the executable instructions to generate the 3D model of the medical device from the at least one fluoroscopic image in the selected coordinate system using the trained deep learning model to perform feature extraction of the medical device and the at least one fiducial marker and to determine a z-position of at least one portion of the medical device within the selected coordinate system comprises determining at least one of a rotation angle, a translation, and/or a scaling factor based on a projection of the radiopaque marker in the at least one fluoroscopic image.

In various embodiments, the system may further comprise a haptic device. In various embodiments, the executable instructions stored on the non-transitory memory device may cause the one or more processors, upon execution of the executable instructions to output a haptic output to the haptic device responsive to a predefined proximity of at least a portion of the 3D model of the medical device to a predetermined portion of the 3D model of the anatomical target in the selected coordinate system.

In various embodiments, the executable instructions stored on the non-transitory memory device may cause the one or more processors, upon execution of the executable instructions to register the 3D model of the medical device with the 3D model of the anatomical target in the selected coordinate system in association with respiratory motion, cardiac motion, or both respiratory motion and cardiac motion.

In various embodiments, the executable instructions stored on the non-transitory memory device may cause the one or more processors, upon execution of the executable instructions to register respiratory motion, cardiac motion, or both respiratory motion and cardiac motion by processing image data, as between the first image data set and the received at least one fluoroscopic image, having a same phase of motion.

In various embodiments, the executable instructions stored on the non-transitory memory device may cause the one or more processors, upon execution of the executable instructions, to output the real-time output image comprising the 3D model of the medical device registered with the geometry of the anatomical target in the selected coordinate system to a display device.

In various embodiments, the system may further comprise a display device. In various embodiments, the display device may include a virtual reality (VR) headset, an augmented reality (AR) headset, a mixed reality (MR) headset, a wearable device comprising a heads-up-display, and/or an area display.

In various embodiments, the anatomical target is an organ and/or a tissue. In various embodiments, the anatomical target comprises an organ and/or a tissue. In various embodiments, the anatomical target is the heart. In various embodiments, the anatomical target comprises the heart.

In various embodiments, the executable instructions stored on the non-transitory memory device may cause the one or more processors, upon execution of the executable instructions and generation of the real-time output image comprising the 3D model of the medical device registered with the geometry of the anatomical target in the selected coordinate system, to output quantitative feedback of z-axis position of at least a portion of the medical device relative to the anatomical target or another anatomical feature with an accuracy ranging from 0.1 mm to 5 mm and a precision of about 10 um to 1 mm.

In various embodiments, the system may further comprise a device providing auditory, visual and/or tactile guidance for open-loop instruction to a interventionalist. In various embodiments, the executable instructions stored on the non-transitory memory device may cause the one or more processors, upon execution of the executable instructions, to output quantitative feedback of z-axis position of the at least a portion of the medical device relative to the anatomical target or another anatomical feature to the device to provide guidance for open-loop instruction to the interventionalist.

In various embodiments, the system may further comprise a robotic controller and a robot comprising an end effector to control the medical device. In various embodiments, the executable instructions stored on the non-transitory memory device may cause the one or more processors, upon execution of the executable instructions, to output quantitative feedback of z-axis position of the at least a portion of the medical device relative to the anatomical target or another anatomical feature as a closed-loop instruction to the robotic controller to cause the robot to move the end effector controlling the medical device to cause a related movement of the medical device.

In various embodiments, the system may further comprise a communication device to communicatively connect the system to an external device and/or an external system.

In various embodiments, the communication device may be a wireless communication device.

In various embodiments, the external device and/or the external system may be located remotely from the system, such as on the cloud, or may be situated locally (i.e., co-located) with respect to the system.

BRIEF DESCRIPTION OF FIGURES

The foregoing and other objects, aspects, features, and advantages of the disclosure will become more apparent and better understood by referring to the following description taken in conjunction with the accompanying drawings, in which:

FIG. 8 depicts z-calculation based on width of objects in fluoroscopic image, in which

FIG. 9 represents determining catheter orientation from elliptical projections of standard markers, in which

FIG. 11 represents cardiac motion, in which

FIG. 12 depicts a schematic of a mixed reality navigation system according to various potential embodiments. Fluoroscopic images may be converted in real-time to a 3D rendering with quantitative feedback of catheter (or other medical device) position and/or angle.

FIG. 13A: Image of 3D printed heart model on a bi-plane c-arm. FIG. 13B: Magnified view of patient-specific 3D printed heart model. FIG. 13C: Schematic of image transfer process and post-processed catheter tracking. FIG. 13D: Image-processing and deep learning steps of bi-plane images with tracking plot.

FIGS. 14A-14D depict deep learning models for z-calculation according to various potential embodiments. FIG. 14A: Image of 3D printed jig holding array of 50 metal spheres at various heights. FIG. 14B: Image of fluoroscopy images at two angles and auto-detection of those spheres. FIGS. 14C and 14D: Graph of error for each sphere based on true value measured from 3D CAD file for both bi-plane (FIG. 14C) and monoplane analysis (FIG. 14D).

FIGS. 16A-16E depict a workflow for preparing training datasets for a mono-plane deep learning architecture, according to various potential embodiments. FIG. 16A: detecting three points of interest on a catheter from bi-plane imaging dataset. FIG. 16B: With the detected POIs and the known rotation angle, the z-dimension is calculated using the equation.

FIGS. 16C and 16D: The ground truth value of the z-dimension for POIs and only AP (anteroposterior) fluoroscopic image may be used to train a CNN regression model in a supervised manner. FIG. 16E: output of the model is retrieving 3D coordinates from 2D fluoroscopic image as input.

FIGS. 17A-B: Schematic images of dynamic heart phantom in both its inspiratory and expiratory positions. FIGS. 17C-D: Actual image of phantom with left and right atrium.

FIG. 18 depicts cardiac motion compensation due to respiration by interpolation of respiration signal, according to various potential embodiments.

FIG. 19A: 2D projection of spine from 3D CT scan. FIG. 19B: Orientation detection against 2D fluoroscopic image. FIGS. 19C-E: Results for an example CNN-based segmentation of spine.

FIG. 20 depicts the frontend (i.e., all pre-operative features (1-8), intra-operative features 1, 2, and 9, and post-operative features 1, 2, and 6 in green) and backend features (i.e., intra-operative features 3-8 and post-operative features 3-5 in blue) of software for each stage of the intervention according to various potential embodiments.

FIG. 23A: The manual optimization of Model A and compare the Euclidian distance error. FIG. 23B: depicting the effect of spatial distribution of groundtruth during training, suggesting the high dependency of the fully connected layer weights on the spatial distribution of the inputs during training. FIG. 23C: corresponds to an inference test for Model A.

FIG. 24A: The manual optimization of Model B and compare the Euclidian distance error. FIG. 24B: highlighting the high dependency of the fully connected layer weights on the spatial distribution of the inputs during training. FIG. 24C: corresponds to an inference test for Model B.

FIG. 25A: The manual optimization of Model C and compare the Euclidian distance error. FIG. 25B: highlighting the high dependency of the fully connected layer weights on the spatial distribution of the inputs during training. FIG. 25C: corresponds to an inference test for Model C.

FIGS. 26A-26C provides summaries of hyperparameters optimization for 3 models according to various potential embodiments.

DETAILED DESCRIPTION

3-D printed models of cardiovascular structures are becoming more prevalent for use in visualizing patient anatomy and enabling devices to be deployed prior to procedures. More sophisticated models can be integrated into flow loops to better recapitulate the physical environment of the heart, and assess potential procedural issues. These advanced flow loops are particularly useful as training tools for cardiology fellows to develop their skills for transcatheter procedures without risking human or animal lives. By having a means to provide quantitative feedback via interfacing with virtual coaches, these models could provide a quantitative means to assess the ability of clinicians to perform these procedures effectively.

Figure 2A:
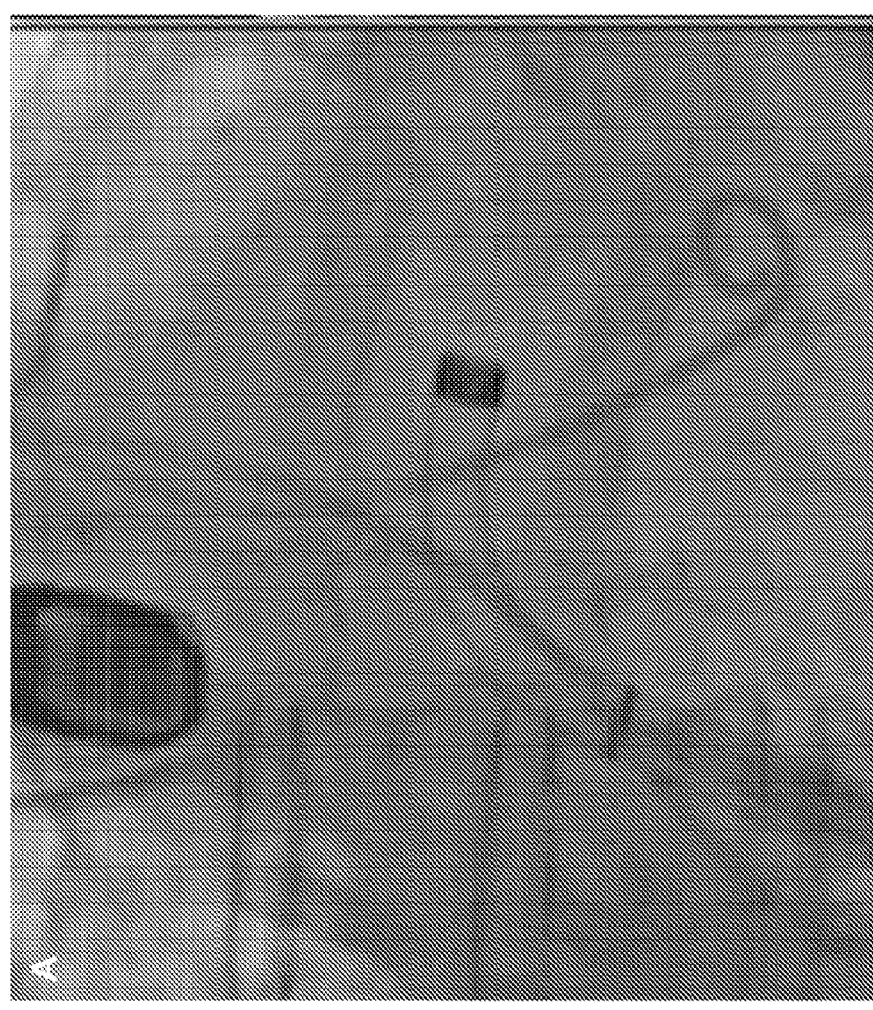
FIG. 2 provides example images of fluoroscopy (FIG. 2A), transesophageal echocardiography (TEE) (FIG. 2B), overlay of computed tomography (CT)/fluoroscopy (FIG. 2C), and overlay of 3-D TEE/fluoroscopy (FIG. 2D).
Figure 2B:
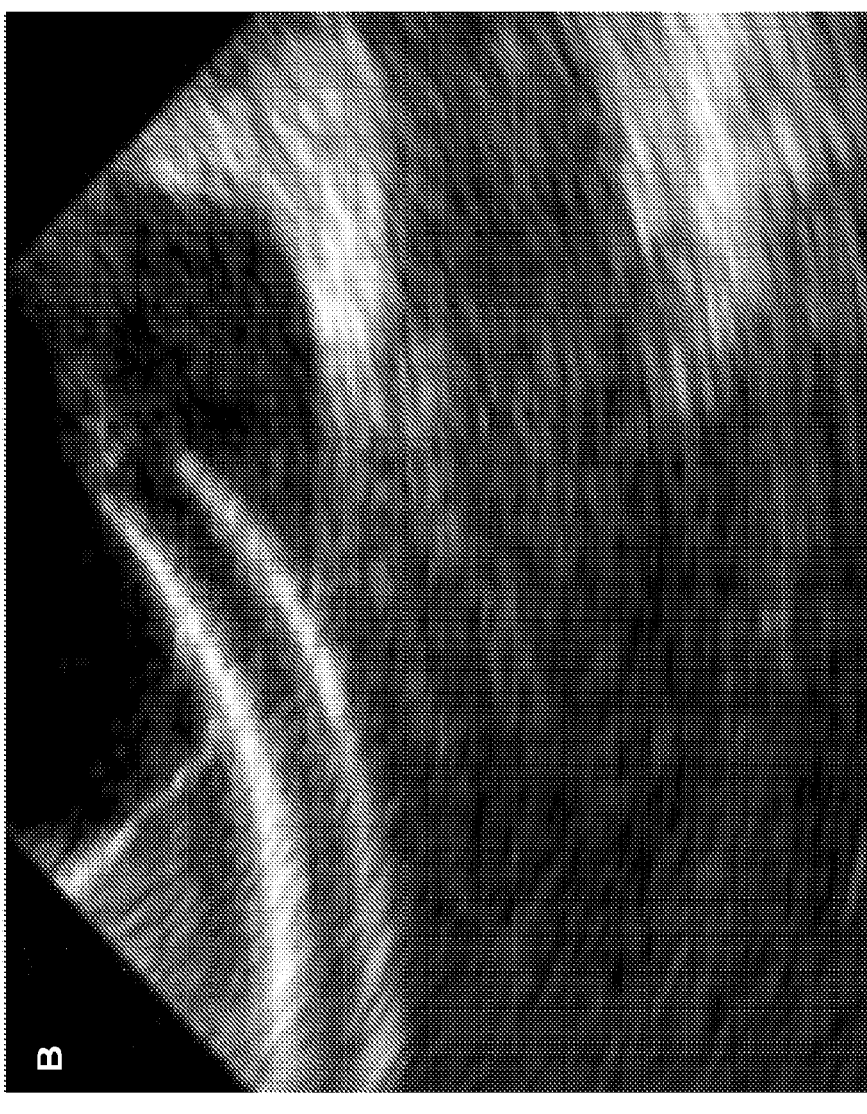

In a clinical setting, transcatheter procedures are generally performed under fluoroscopy (x-ray based imaging) and echocardiography (ultrasound-based imaging), since these two types of imaging modalities can provide real-time visualization of either the heart, catheter, or a device (see, e.g., FIGS. 2A, 2B). Fluoroscopy is the most prevalent form of imaging in catheterization laboratories, since it is the easiest to operate and interpret, provides real-time imaging, visualizes a large area, and can easily distinguish radiopaque markers commonly utilized on minimally invasive devices. However, the heart is transparent to fluoroscopy (see, e.g., FIG. 2A), so interventionalists use contrast agents in the blood flow to visualize temporarily the cardiac anatomy. Furthermore, fluoroscopy only provides a 2D projection, and therefore no depth information is in the image. Echocardiography methods are also common imaging modalities employed in a catheterization lab. However, the image quality may be less precise and may require the operation by another specialist, unnecessarily complicating the overall coordination of the system.

Figure 2C:
Figure 2D:
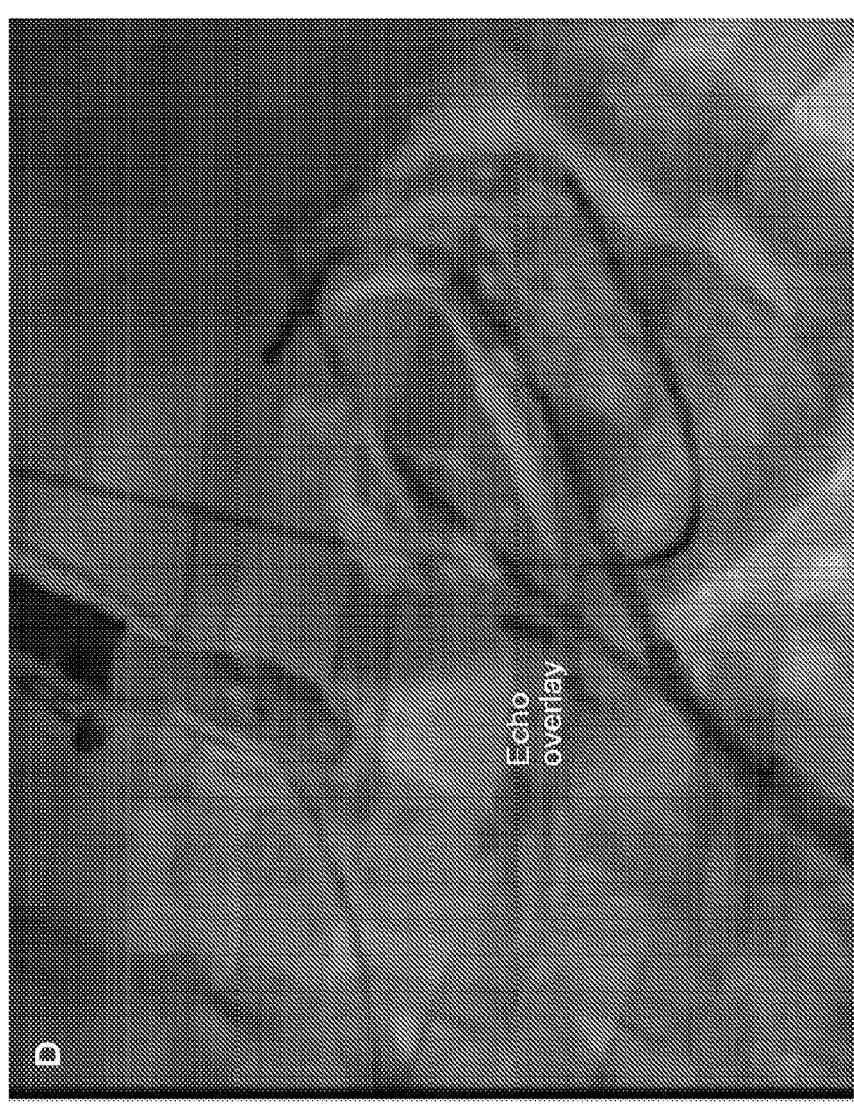

Recently, commercial systems that register real-time fluoroscopic and ultrasound imaging, as well as preoperative imaging modalities, such as computed tomography (CT) and magnetic resonance imaging, have been developed (e.g., Siemens ACUSON, Philips HeartNavigator), but they simply overlay the multi-modality images, as seen in FIGS. 2C and 2D. Although these systems may offer potential benefits, the steep learning curve of these systems may result in increased procedural time and radiation exposure. These limited benefits are partially explained by the fact that the method of overlaying images may in fact impair the interpretation of the original image by the interventionalist. In addition, these systems are very costly and will result in a slow adoption by hospitals. Most important, these systems do not directly interpret the 3D position of the catheter in fluoroscopy, only its 2D projection, and therefore interventionalists cannot directly orient the catheter's trajectory or depth within the cardiac anatomy.

Figure 5:
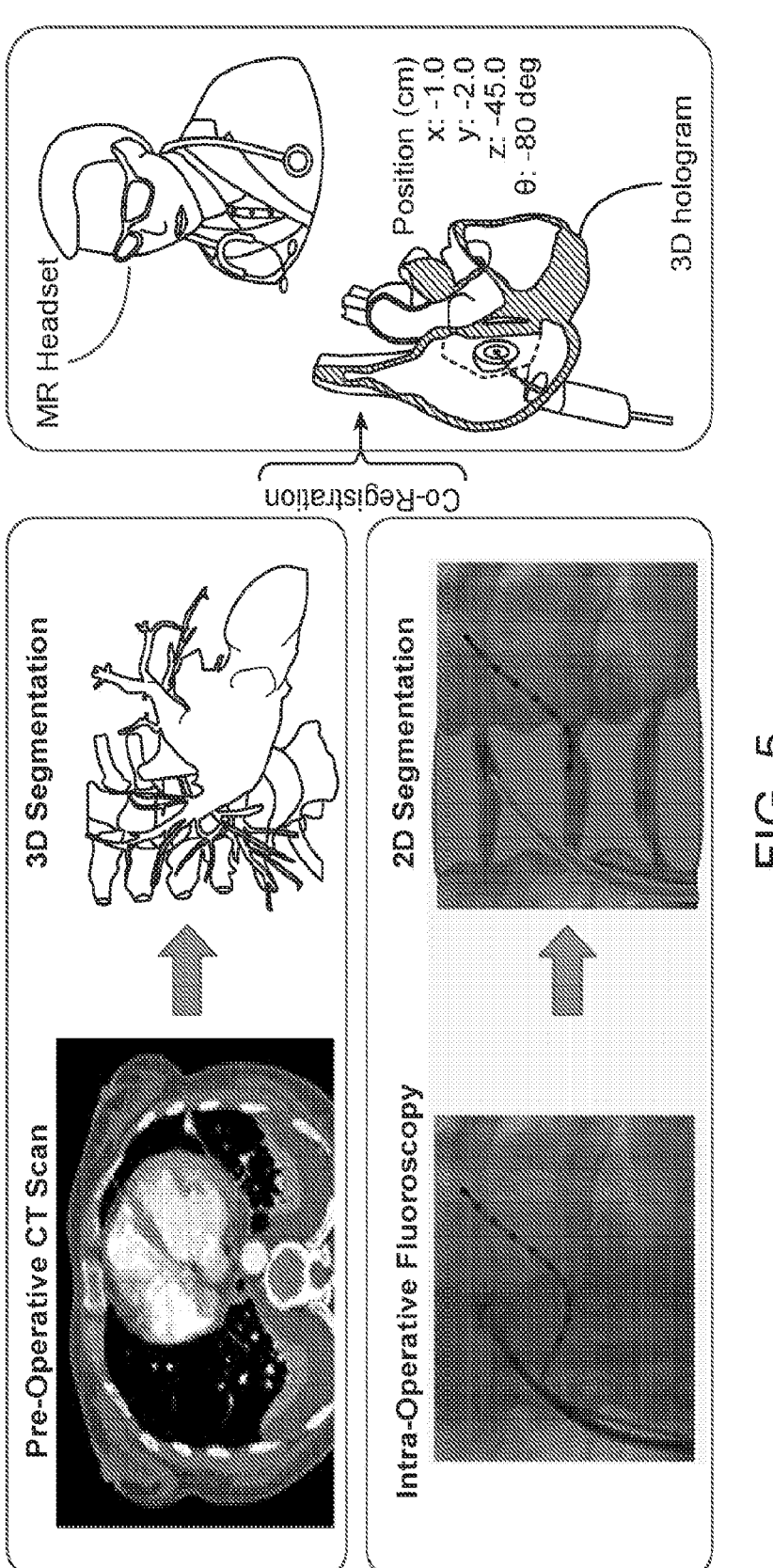
FIG. 5 depicts a schematic representing use of a CT scan to generate MR rendering and the spine as an intrinsic fiducial marker for co-registration according to various potential embodiments.

Various embodiments of the disclosed approach may employ an image-guidance system based on co-registering CT and fluoroscopy images for interventional cardiac procedures (see, e.g., FIG. 5). These two modalities may be chosen because CT provides a detailed 3D image of the whole heart's geometric anatomy, and fluoroscopy provides real-time images that can track a catheter effectively. To co-register these two imaging modalities, the spine may be chosen because it is present and relatively stable in both imaging modalities, and therefore can be used as an intrinsic fiducial marker. Various embodiments may provide real-time tracking of the catheter in 3D space from a single fluoroscopy plane by employing methods that will determine the 3D orientation of a catheter from a single fluoroscopic plane using machine learning methods that assess small differences in the projected image of the catheter at different depths, as described in more detail below. Additionally, the motion of the heart occurs due to both respiration and contraction, and therefore, will not always be in the same position as displayed in the CT scan, which can lead to error in the co-registration of the position of the catheter relative to the heart. Embodiments of the disclosed approach provide cardiac motion compensation by decoupling these two motions and helping ensure that the fluoroscopic images that are processed are selected during the same phase as the CT scan (e.g., end-diastole and deep inspiration) to minimize error in registration.

Real-time tracking of catheter in 3D space from a single fluoroscopy plane: Currently, there are strategies (e.g., rotational angiography) in which multiple fluoroscopic angles can be taken to reconstruct a 3D geometry during the procedure. This approach, however, induces significantly more radiation, is time-consuming and expensive, and cannot be done in real-time. However, for a catheter, which has a known geometry, its orientation can be deduced from taking just 2 angles. These two angles can be achieved using bi-plane fluoroscopy in which 2 sets of imaging equipment (i.e., c-arm) are used in parallel, but this doubles the amount of radiation for the patient and significantly increases it for the physician; beyond this, many catheterization labs do not have access to this expensive equipment. An alternative solution is to acquire 2 angles serially (each at a different angle) with a single c-arm. This approach also increases radiation exposure and is time consuming and impractical for most procedures, particularly if the c-arm is not motorized. Various embodiments of the disclosed approach may employ a machine learning model that can determine the z-position of a catheter to automate this 2D to 3D conversion from a single plane fluoroscopic image. This approach may be chosen because it could more easily be adopted by medical device manufacturers since it requires little to no change to current catheters and imaging equipment, thus, helping this approach have greater impact to clinical interventions.

Figure 6:
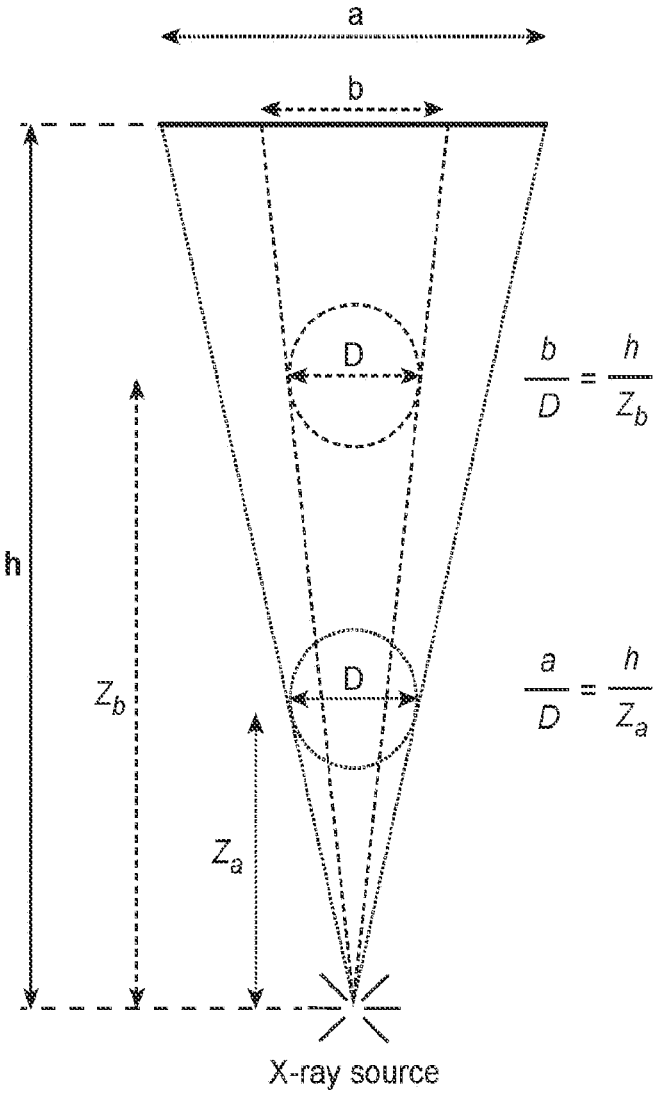
FIG. 6 depicts difference in projected image size due to z-position of object in fluoroscopy according to various potential embodiments.

In various embodiments, the general approach disclosed herein may leverage the fact that objects will appear larger as they are closer to the source of the c-arm. This allows for a calculation of the z-position (see, e.g., FIG. 6). Prior attempts to implement this approach have resulted in significant error (e.g., up to 1 cm) due to the limited resolution of the fluoroscopic image, and limited distance of the source to detector, despite getting average errors of about 2 to 4 millimeters (mm). Various embodiments of the disclosed approach advantageously use machine learning to automate the edge detection of specific features of a catheter to accurately calculate its z-position from its projected size. In various preferred embodiments, this may be done with the width of the catheter directly, but as alternative solutions, the anticipated projection shapes from custom-designed radio-opaque markers may be employed to more accurately determine the z-dimension of the catheter. A benefit of this method is that calculating several markers at once will limit the number of potential solutions since only a certain combination are possible given the fixed orientations of the catheter, and thus the relative positions of the markers. Table 1 summarizes advantages and disadvantages of these three detectable features of a catheter, which are described in more detail below.

TABLE 1

| Relative Ranking of Detectable Features | | |
| --- | --- | --- |
| Catheter Feature | Catheter Applicability | Z-Position Accuracy |
| Width (Standard Catheter) | High | Low |
| Elliptical Angle (Standard Markers) | Medium | Medium |
| Yaw, Pitch, Row (Custom-Marker) | Low | High |
| Width (Spherical Metal Ball Markers) | Low | Medium |

Figure 7:
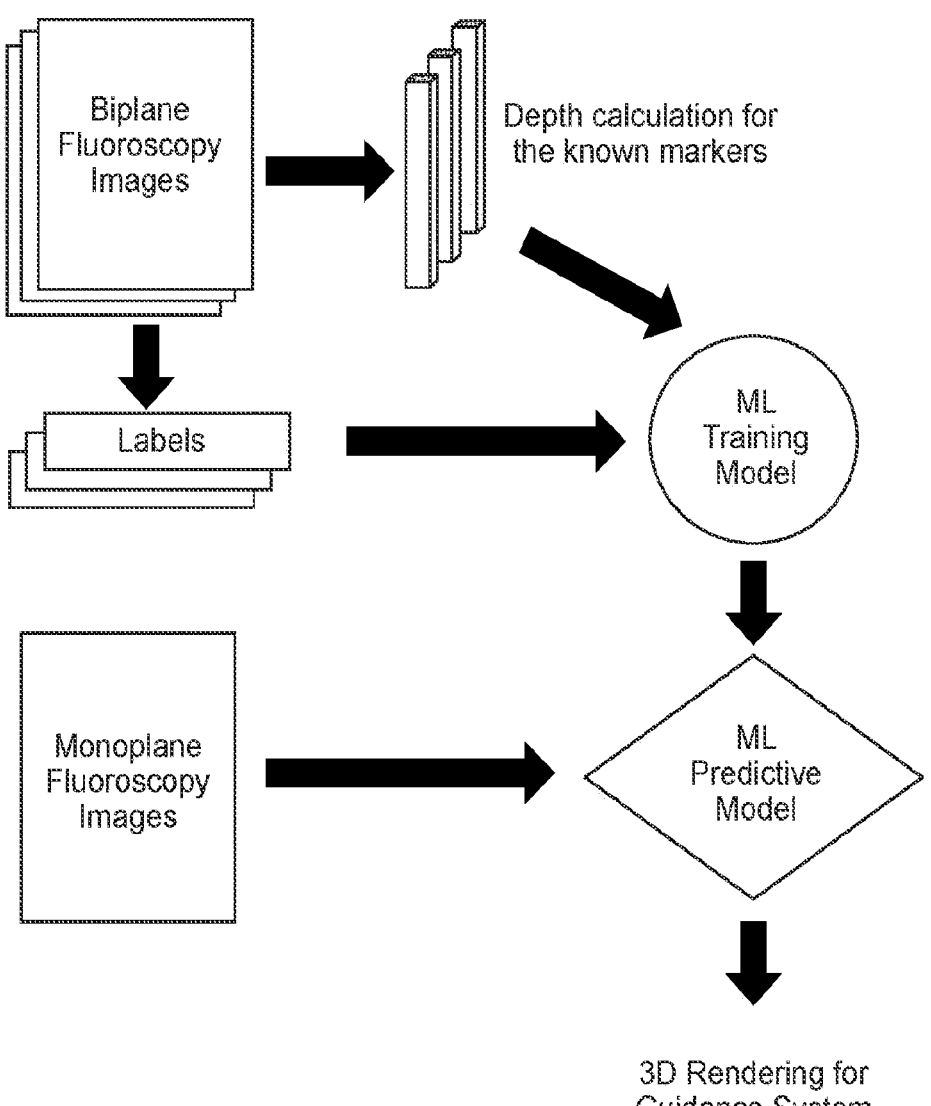
FIG. 7 depicts an example machine learning workflow for calculating z-position from a single fluoroscopic image according to various potential embodiments.
Figure 8A:
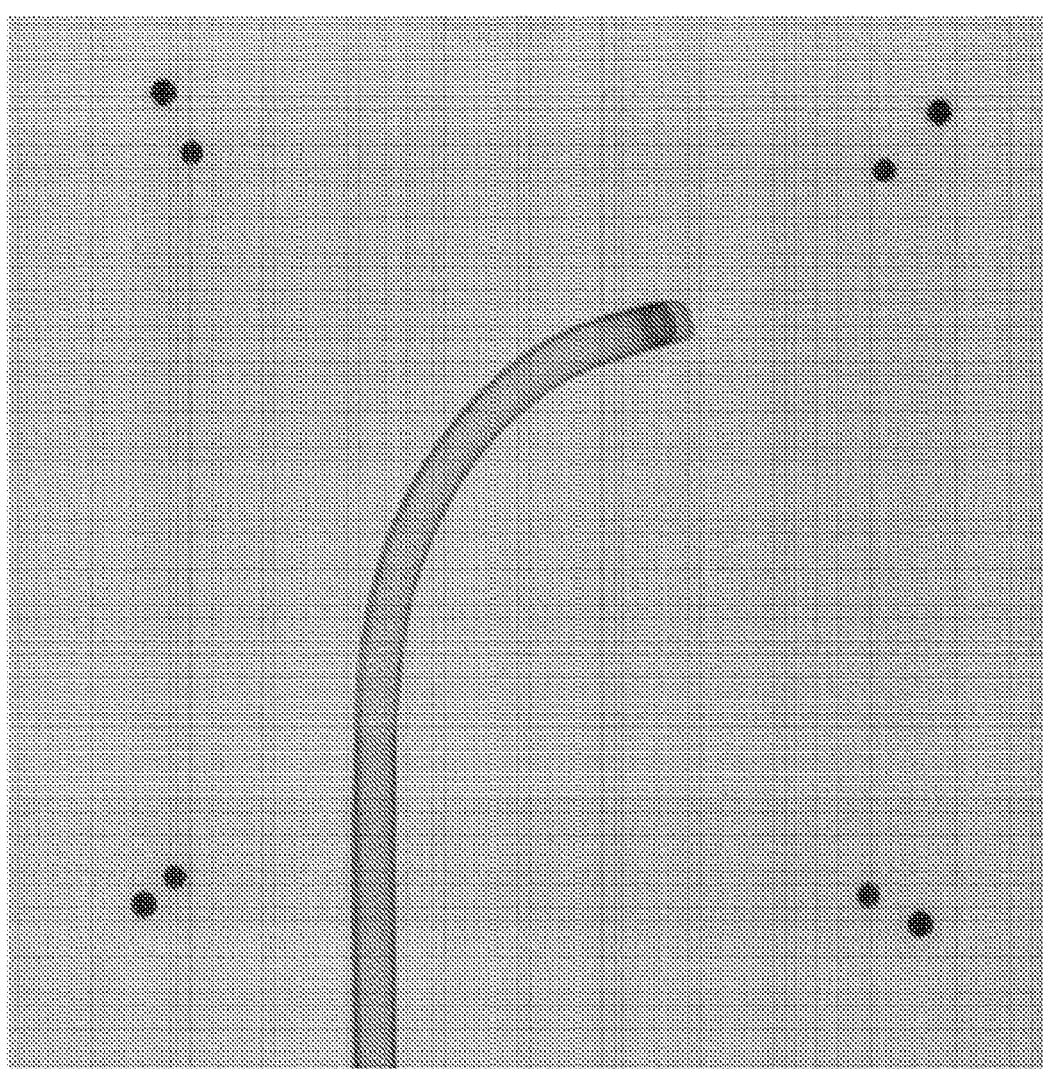
FIG. 8A depicts a fluoroscopy image with catheter and 2 mm reference balls.
Figures 8B, 8C:
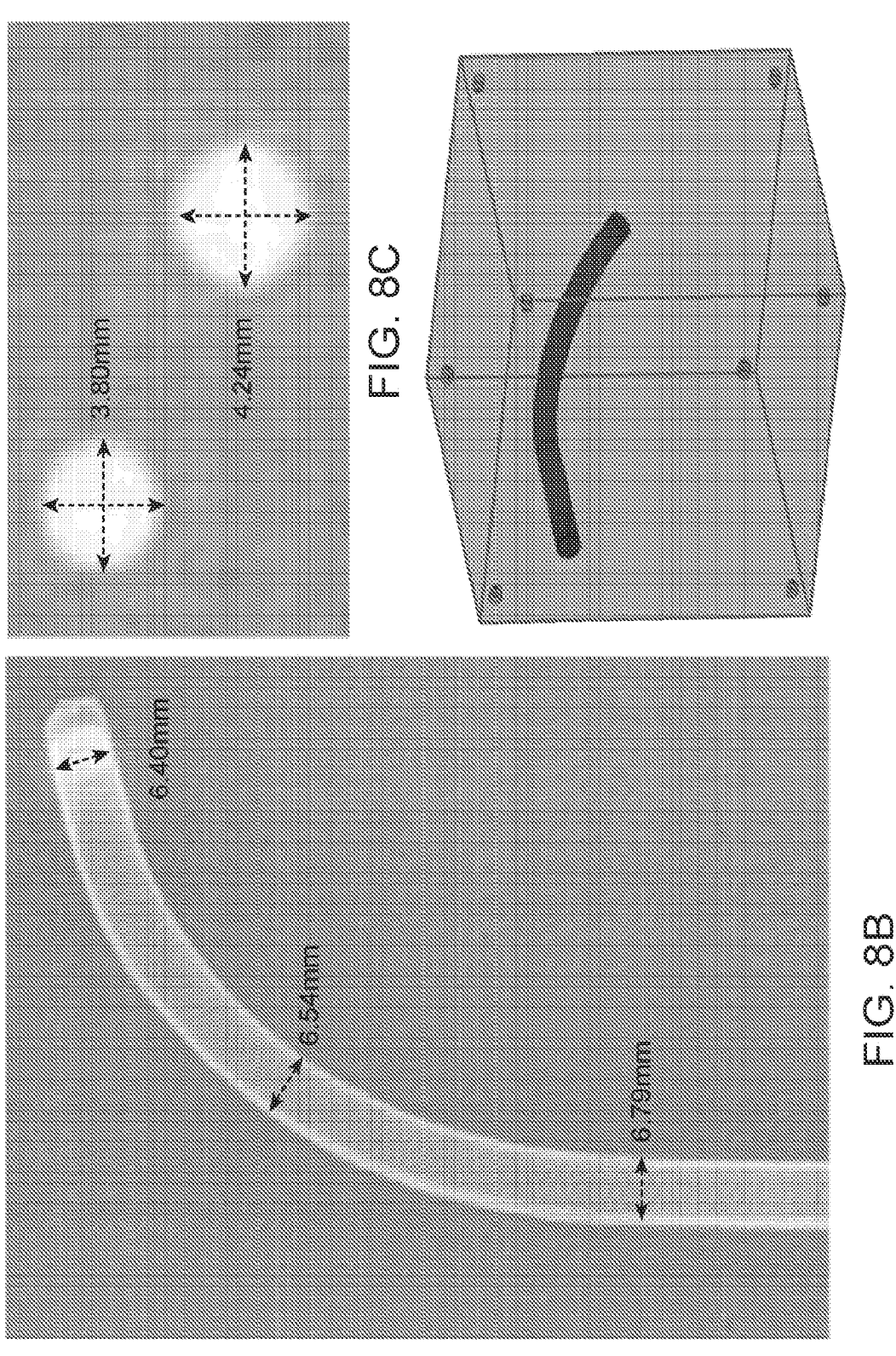
FIG. 8B depicts contrast adjustment and width measurements.
FIG. 8C depicts 3D reconstructions in CAD model based on calculations.
Figure 8D:
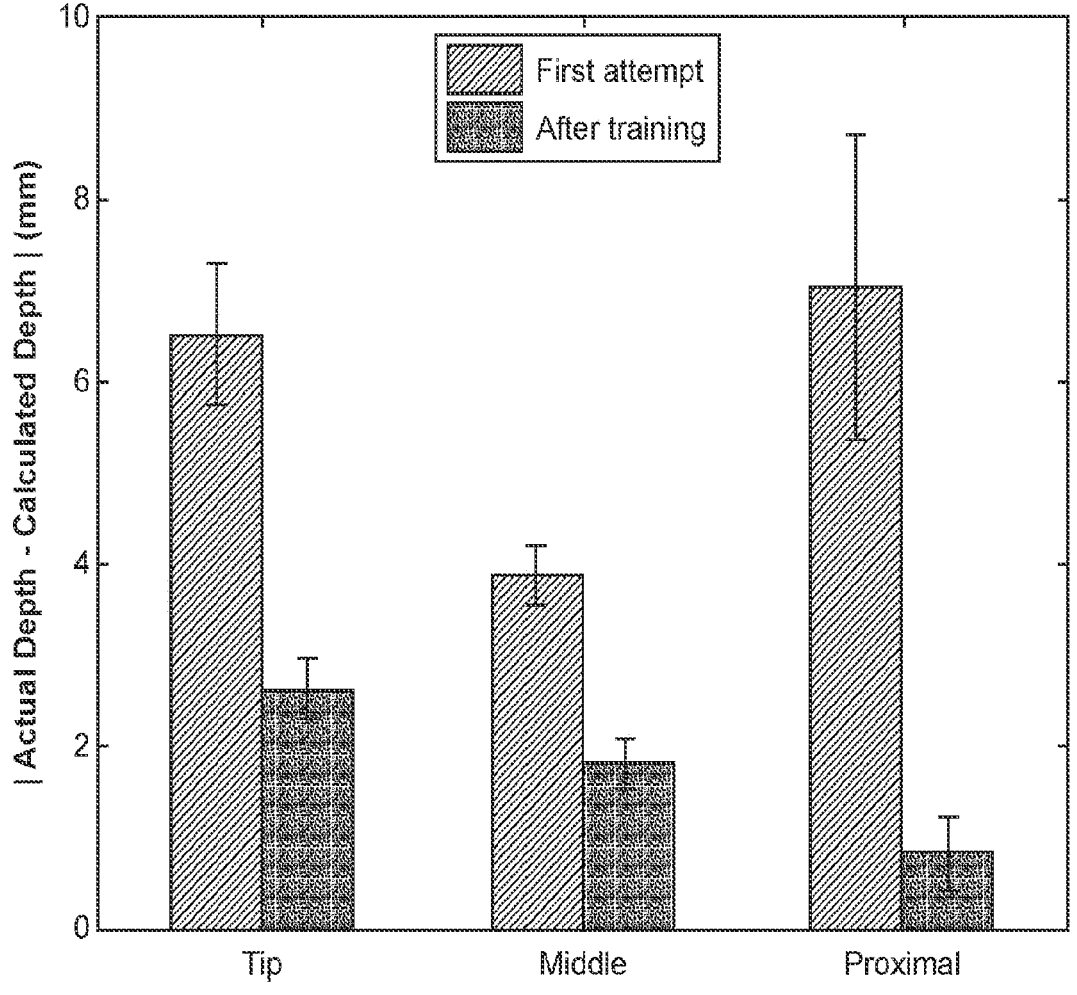
FIG. 8D depicts error in calculation during first attempt of measurement and after human-based training, according to various potential embodiments.

In various potential embodiments, deep learning models may be used for performing automated feature extraction to accomplish the z-position calculation (see, e.g., FIG. 7). Embodiments may employ U-Net, a supervised deep learning architecture for biomedical image segmentation. The z-position of the catheter may be calculated at several locations using bi-plane imaging. The approach may then back-calculate the corresponding width of the catheter and label it in the monoplane fluoroscopic images, which will serve as the ground truth for a supervised convolutional neural network (CNN) model. These ground truths will be fed into the U-Net model for segmentation of the catheter from the fluoroscopic images. In various embodiments, the model may be trained to segment the catheter at widths that correspond to its actual z-position. We will perform this on a data set of 50 patient CT scans that we will 3D print heart models and perform mock procedures where at least a thousand images will be acquired per patient. The 50 scans (50,000 images) will be divided into 3 parts: (i) training set (60%; 30 scans), (ii) validation set (20%; 10 scans), and (iii) testing set (20%; 10 scans). The training and validation set may be used during model training. The testing set will be used for model evaluation at the end of the model training. Additional patients will be obtained if further training or validation is needed. The performance of the model may be assessed on testing set by Dice coefficient and overall computational time. As preliminary data, we imaged a single catheter and performed the width measurements manually (see, e.g., FIG. 8). As can be seen, initial attempts resulted in worse measurements than after training with repeated measurements, suggesting that more optimal edge detection methods can result in higher accuracies. In various embodiments, if employing disclosed machine learning methods improves the precision of edge detection by even a factor 2, this can have a significant impact on interventional procedures.

Figure 9A:
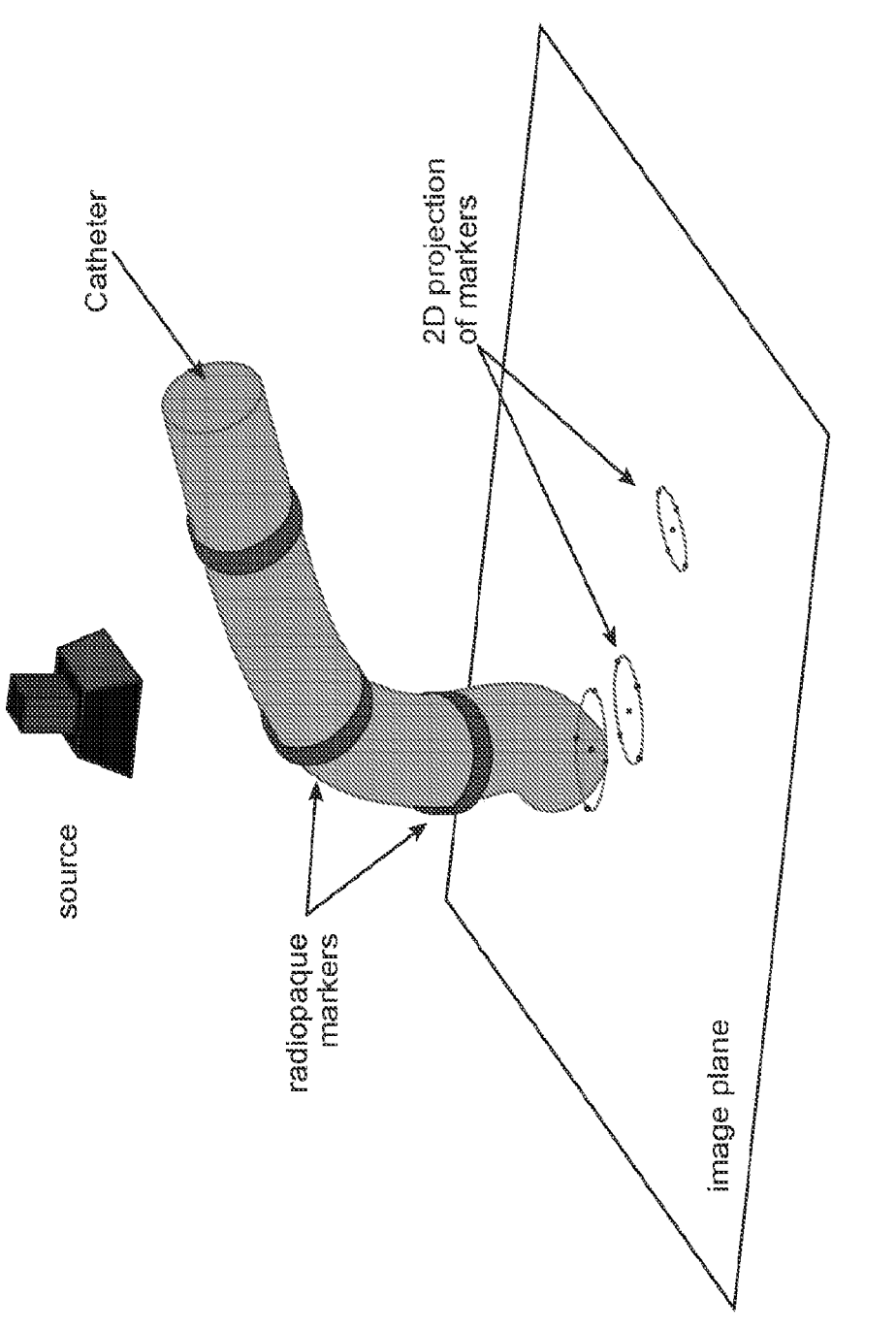
FIG. 9A depicts a schematic of mock catheter with circular radio-opaque markers.
Figure 9B:
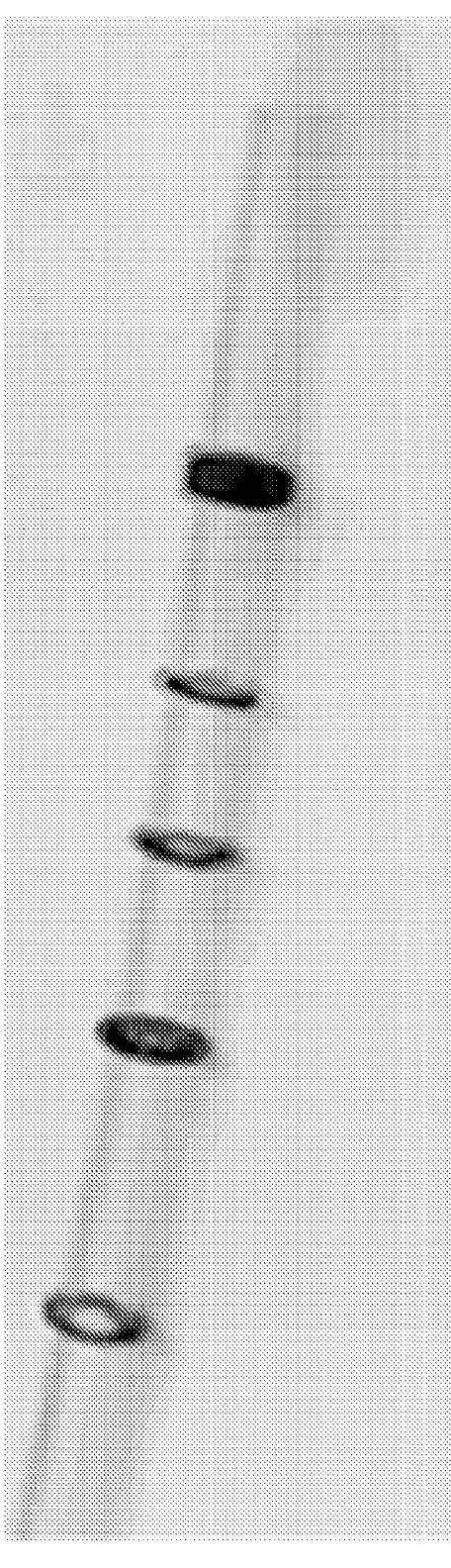
FIG. 9B depicts a mock catheter with markers.
Figure 9C:
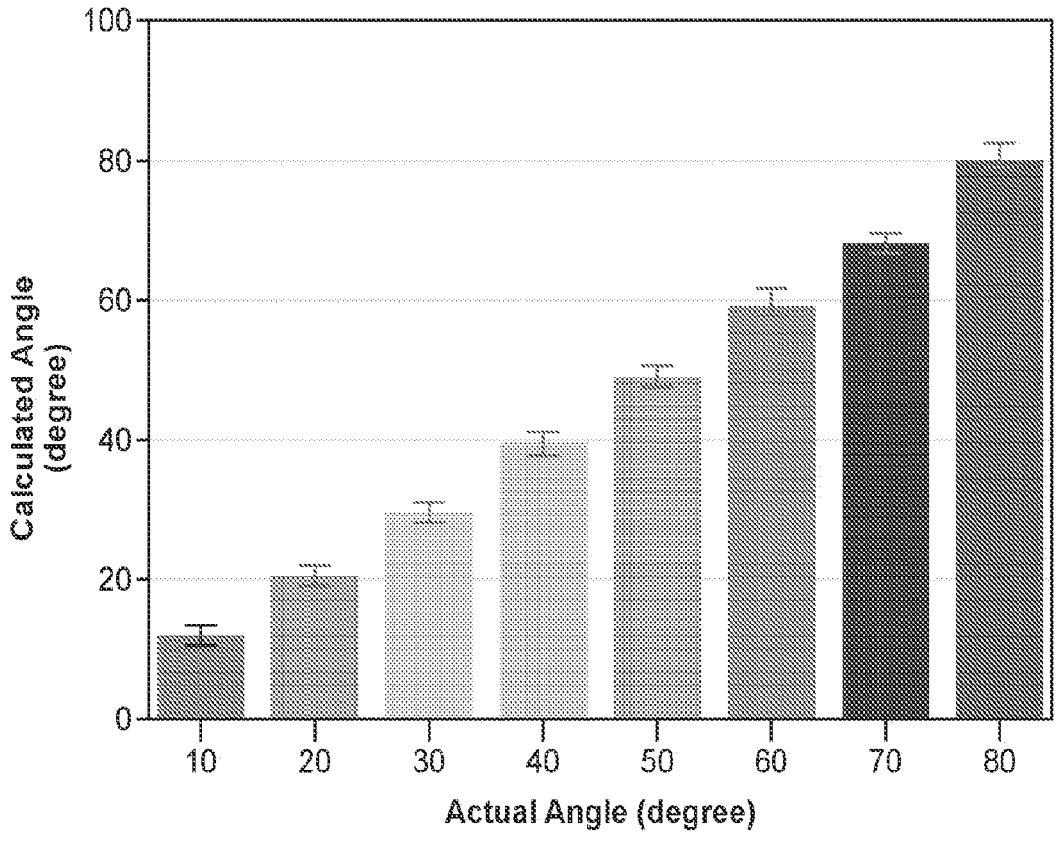
FIG. 9C depicts data showing angle measurements according to various potential embodiments.

We highlight three approaches for the radio-opaque markers that may be pursued for various embodiments of the disclosed approach, the first one that uses conventional circular markers (see, e.g., FIG. 9), the second one with a custom-shape marker (see, e.g., FIG. 10), and the third one utilizing spherical metal ball markers on the catheter. Using standard circular radio-opaque markers, the orientation of the catheter can be calculated by the elliptical contour in the 2D projection of the fluoroscopic image. The angle between the catheter's axial axis and the image plane may be calculated using $\theta=\cos^{-1}(b/a)$; where, a and b are the long and short axes, respectively. FIG. 9A shows a mock catheter used to illustrate this principal, and FIG. 9C shows eight groups of catheter orientations with an increment of 10 degrees that were successfully calculated.

Figure 10:
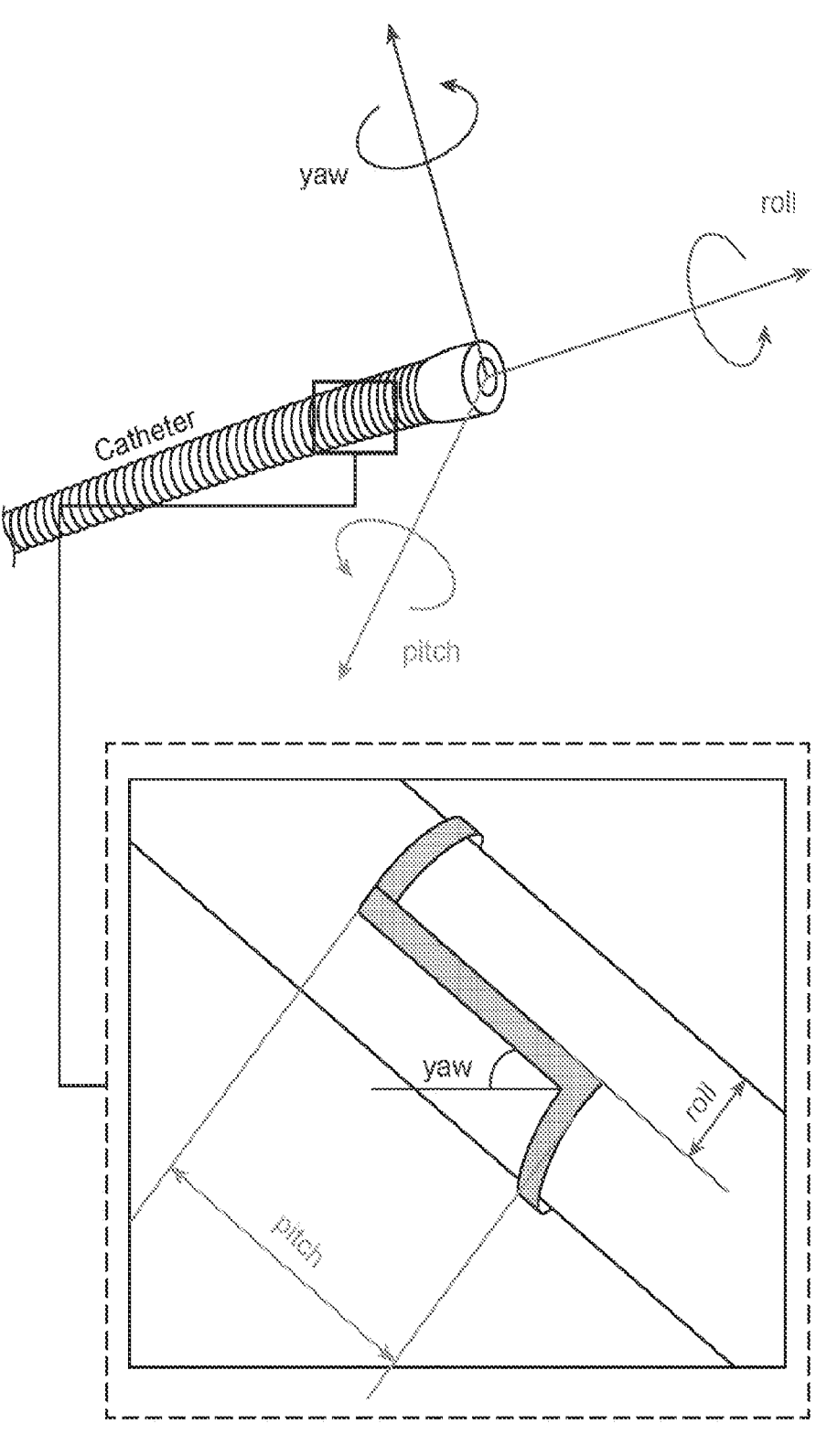
FIG. 10 represents custom-markers for orientating the occluder, depicting a schematic of custom-made radio-opaque markers that enable 3D alignment from fluoroscopic imaging according to various potential embodiments.

In various embodiments, another way to determine the 3D orientation is to calculate the out-of-plane angle (i.e., pitch angle) of the catheter using asymmetric radio-opaque markers (see, e.g., FIG. 10). The detection of the marker length on the image plane may be done using $\theta=\arccos d/l$, where $\theta$ is the pitch angle, d is the detected length of the radiopaque marker in the image plane, and/is the physical length of the radiopaque marker. Here, $d=\sqrt{(x-x_0)^2+(y-y_0)^2}$ as measured by the detected pixel positions. The calculation of the roll angle may be based on the marker's location, relative to the centerline of the catheter, $\varphi=\arcsin d/r$, where d is the distance between the marker and centerline of the catheter, and r is the radius of the catheter. The calculation of the yaw angle may be based on the detection of the endpoints of the radiopaque marker, $\omega=\arctan((y2-y1)/(x2-x1))$. By calculating these angles for each marker along the catheter, the path of the catheter can be quantified, including the final orientation of the device within the heart.

In various embodiments, incorporating spherical metal balls marker into a catheter makes it even easier compared to the circular radio-opaque markers. This is because the projection of spherical metal balls marker in the fluoroscopic image will be circular regardless of any catheter configuration. While in the case of the circular radio-opaque markers, the projection of the marker can vary from circular shape to an elliptical shape with and without void space. This variation can be leveraged to increase the accuracy of the Z calculation by considering orientation of each segment, but can be effected by background image artifacts as well.

Figure 3A:
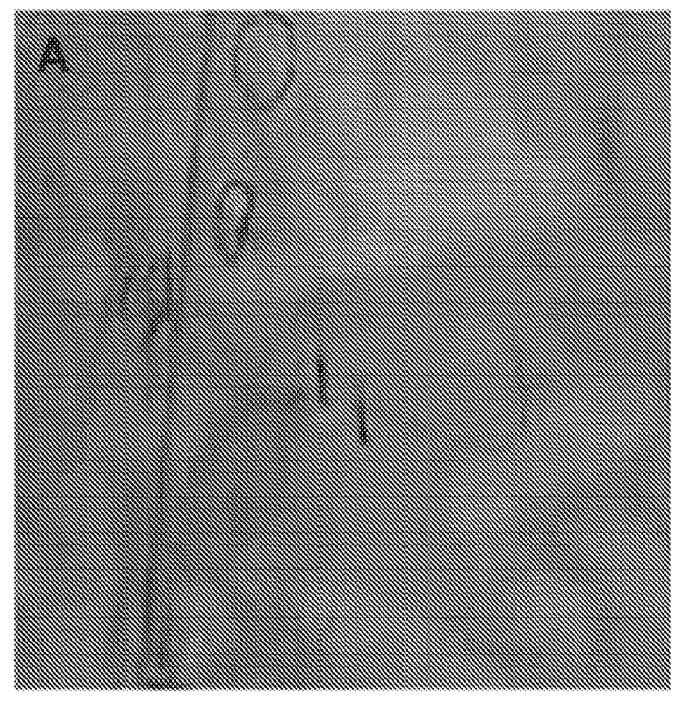
FIG. 3A depicts a standard fluoroscopic image.
Figure 3B:
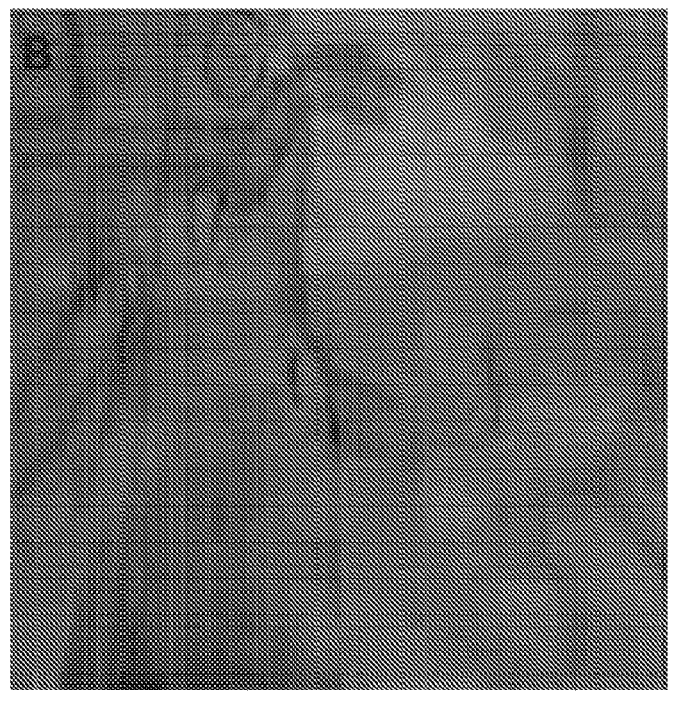
FIG. 3B, depicts a fusion image of a computerized tomography (CT) scan on a fluoroscopic image.
Figure 3C:
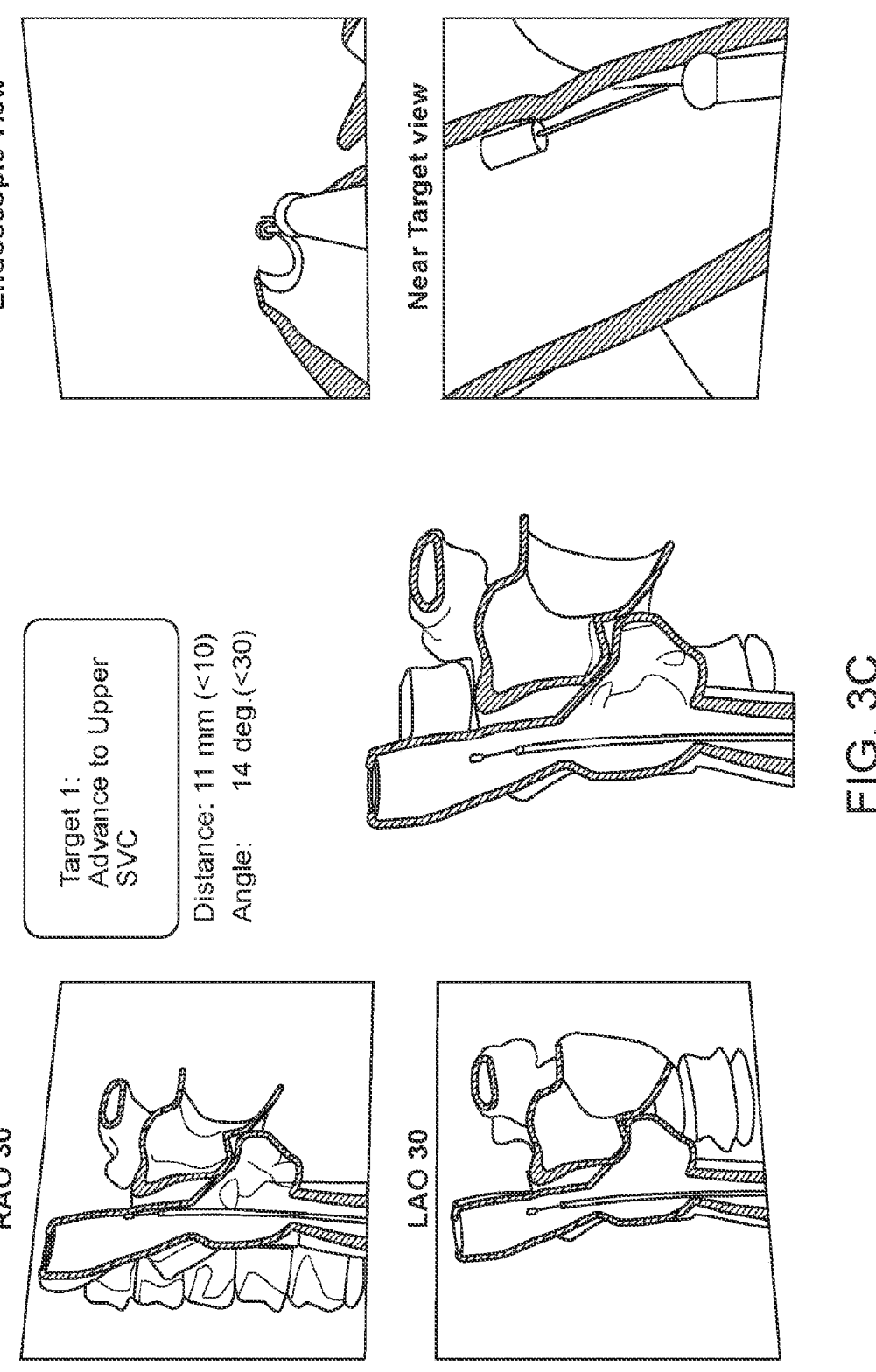
FIG. 3C depicts an image of a mixed reality (MR) display with quantitative feedback and multiple viewing angles, according to various potential embodiments.

In various embodiments, custom software may be employed to import the converted catheter orientation in the same coordinate space as the 3D CAD of the heart, which may be segmented from a pre-operative CT scan. An image grabber hardware may be used to acquire fluoroscopic images from the C-arm in the catheterization lab and send to the PC for real-time processing as described above. Visualization of the catheter may be done using multiple views (see, e.g., FIG. 3C). The user interface may be optimized based on user needs.

Cardiac motion compensation: The motion of the heart occurs due to both respiration and contraction, and therefore, will not always be in the same position as displayed in the CT scan, which can lead to error in the co-registration of the position of the catheter relative to the heart. Embodiments of the disclosed approach can decouple these two motions and ensure the fluoroscopic images that are processed, are selected during the same phase as the CT scan (i.e., end-diastole and deep inspiration) to minimize error in co-registration. Obtaining these phases may be done by either using sensors that are synchronized with our system, or direct image-processing algorithms.

Figures 11A, 11B:
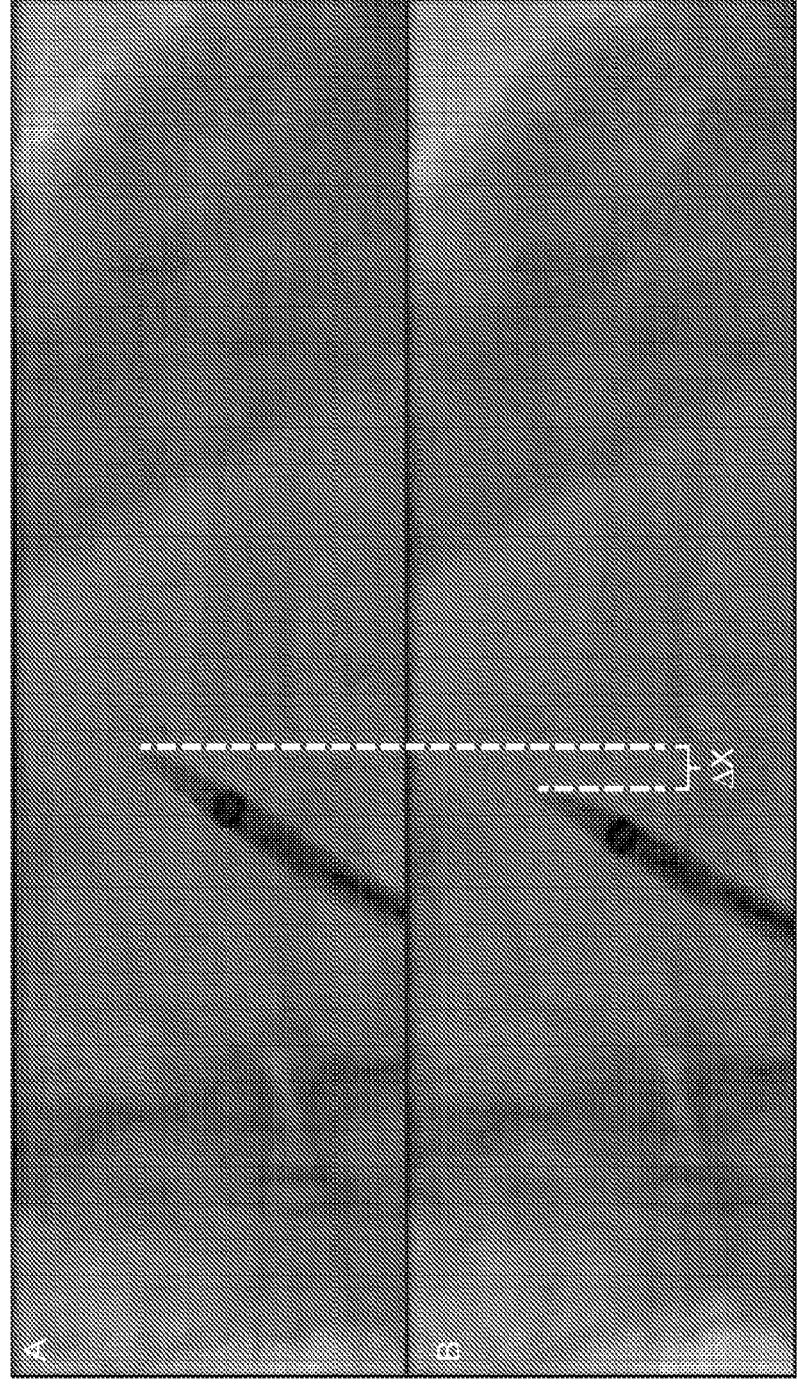
FIG. 11A depicts a fluoroscopic image at diastole.
FIG. 11B depicts a fluoroscopic image at systole.
Figure 11C:
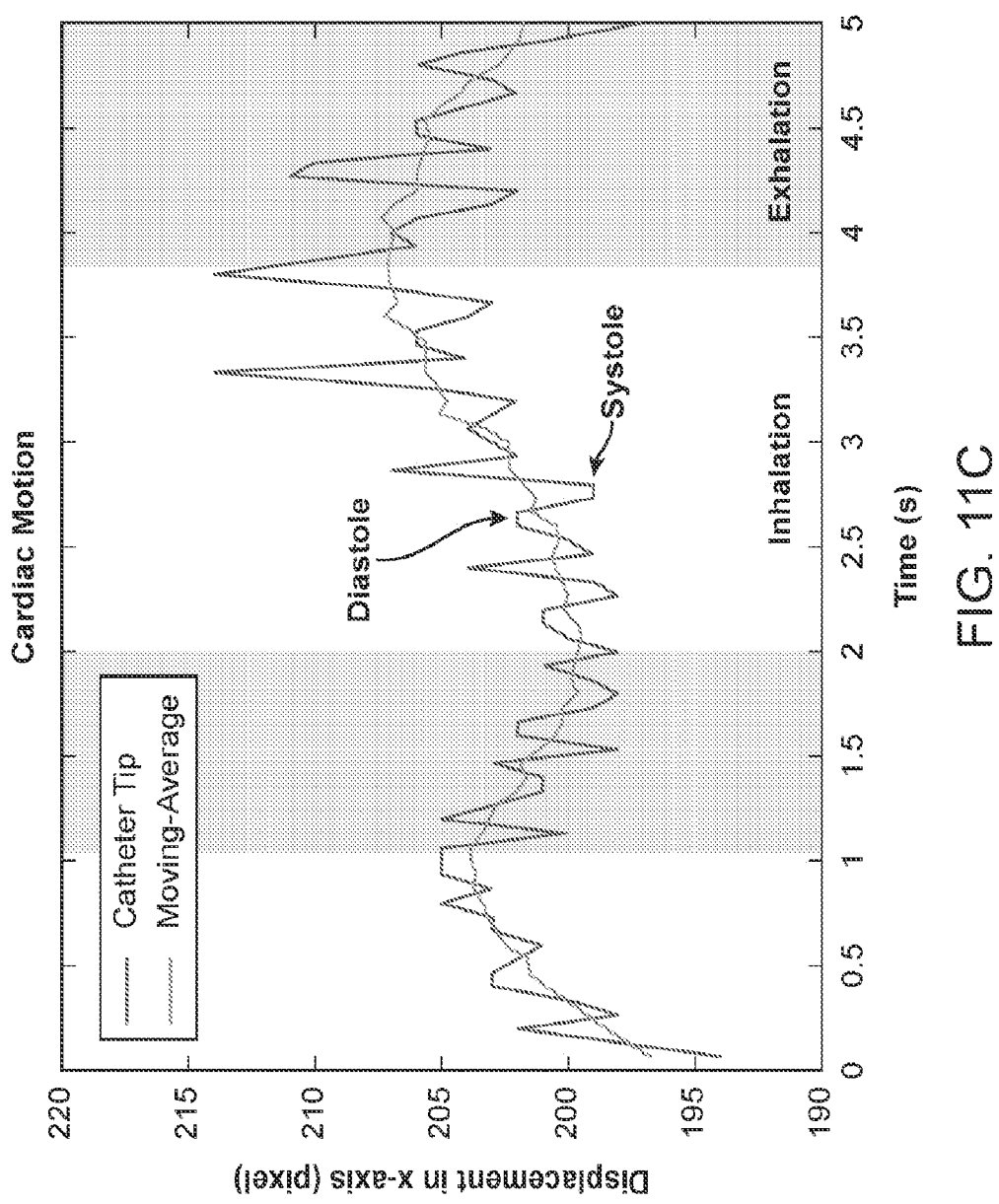
FIG. 11C depicts a graph of catheter tip displacement in x-direction and its moving average value according to various potential embodiments. Peaks in catheter tip indicates cardiac phase and the moving average indicates respiratory phase.
Figures 13A, 13B:
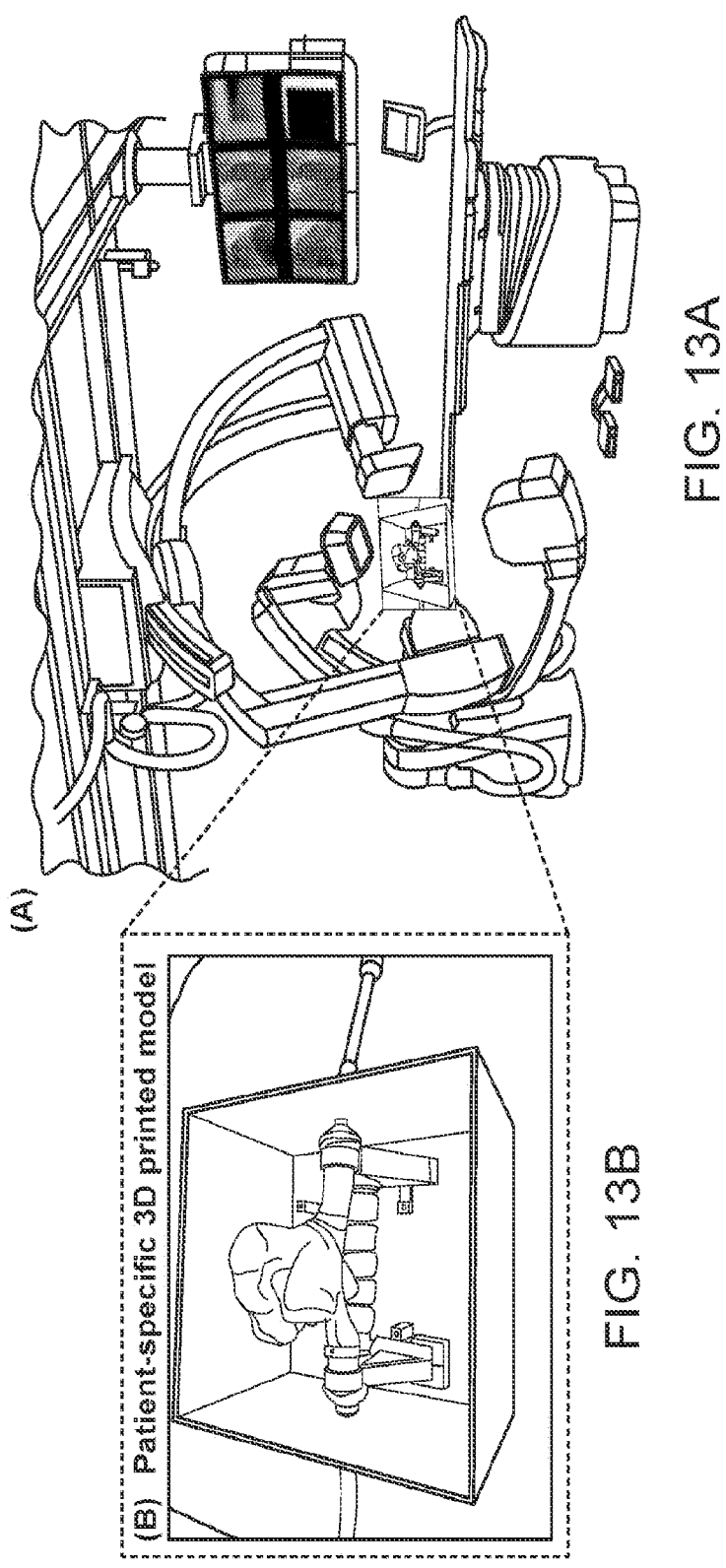
FIGS. 13A-13D depict schematics of a training system according to various potential embodiments.
Figures 13C, 13D:
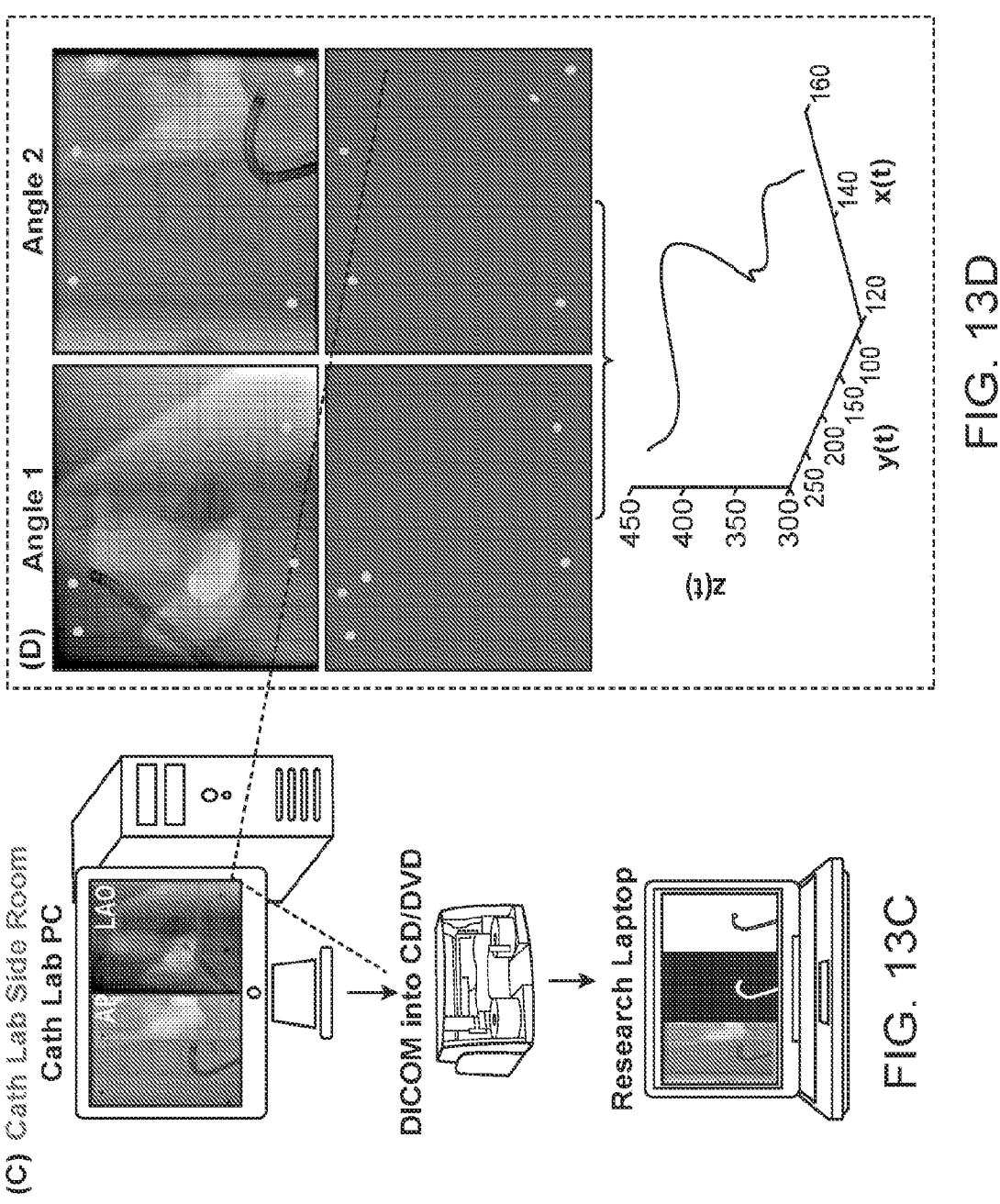
Figure 14C:
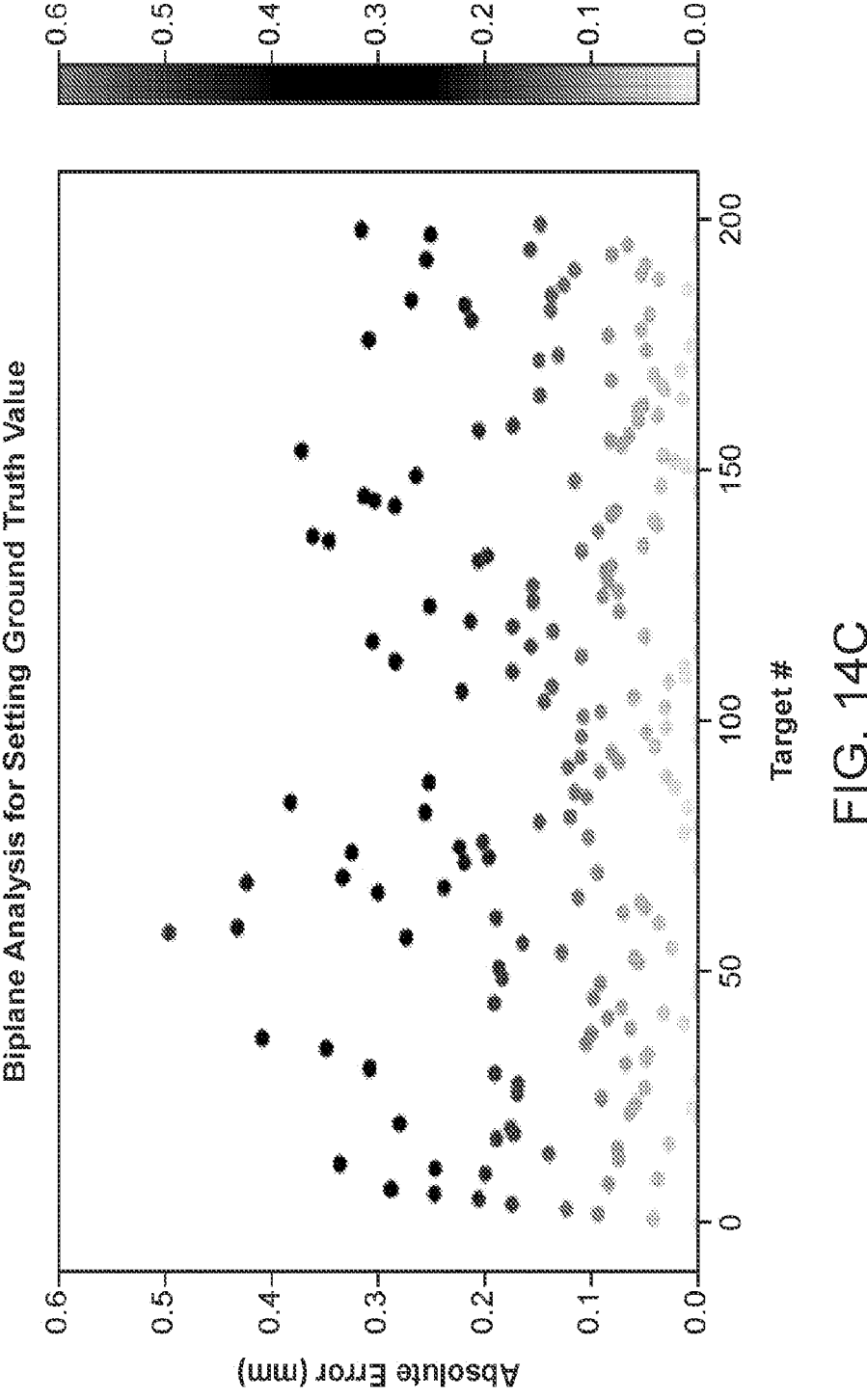
Figure 14D:
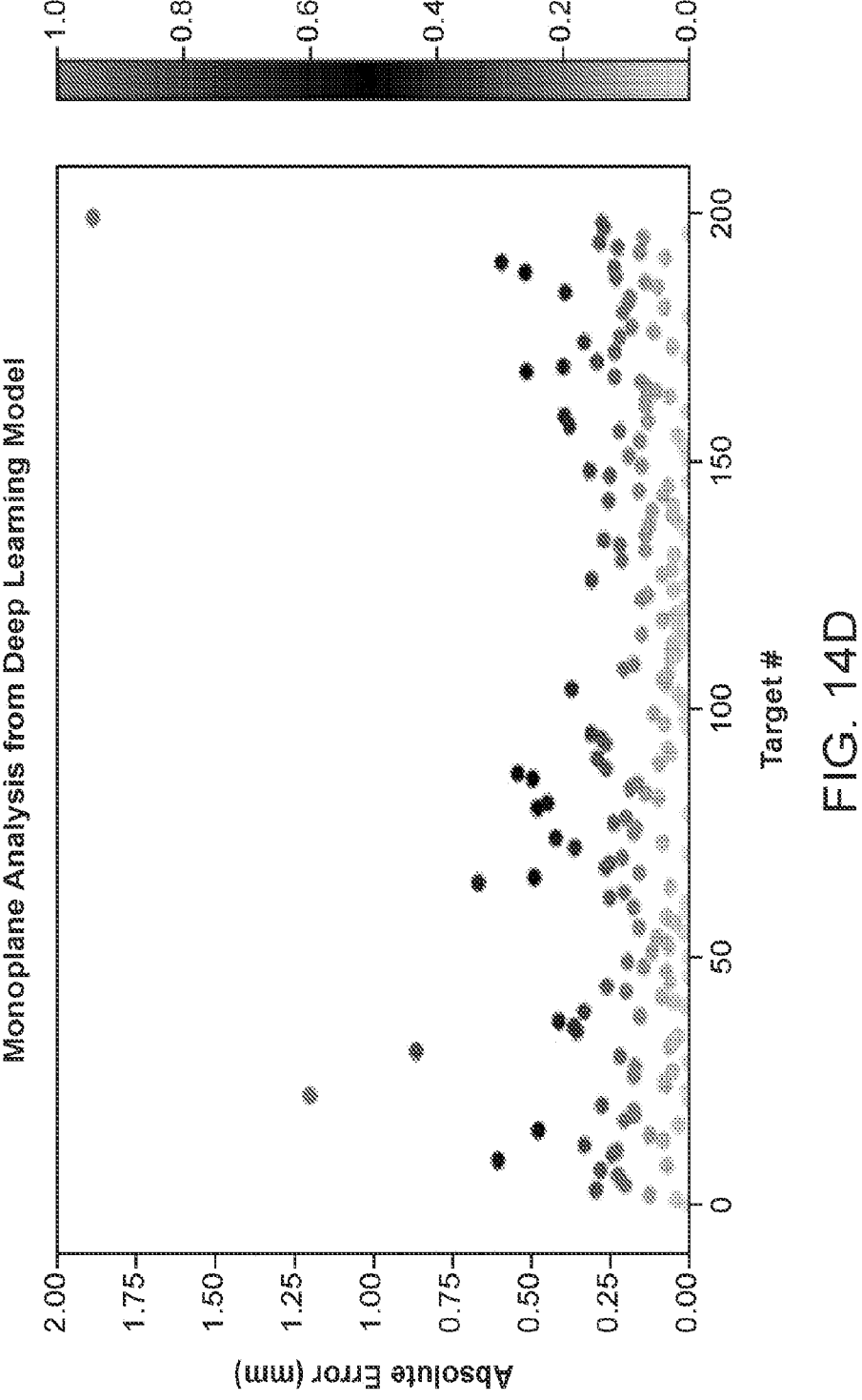

In various embodiments, fluoroscopic images are often taken as short videos and therefore the motion of the heart can be indirectly seen due to cyclic motion of certain features (e.g., contrast, background artifacts), including the catheter itself (see, e.g., FIG. 11). Various embodiments may utilize image-processing algorithms to track the motion of the catheter from these fluoroscopic video files, in real-time, to extract an image that has the catheter in end-diastolic phase. In various embodiments, it is important to note that the magnitude of this motion will not be used to directly compensate for the motion in the heart, it is only used to select an image that is in the same phase as the CT scan, and therefore changes in amplitude of the waveforms will not influence the accuracy of this method. However, the angle of the c-arm will change which direction needs to be analyzed by the image-processing algorithms. This approach may be optimized using the database of fluoroscopic images with known c-arm angles to do so.

Similarly, various embodiments may use the same image-processing used for compensating motion from cardiac contractions to compensate for respiration in real-time. Alternatively, since a patient is told to hold their breath at full inhalation, referred to as deep inspiration breath hold (DIBH), during CT acquisition, only a single target position is needed to be matched. Therefore, during fluoroscopic acquisition, the patient will also perform a DIBH (either consciously or via a respirator), and thus, there is no expected motion in the video files due to respiration and the heart should be near the position taken during the CT scan. However, there can still be misalignment of the heart due to a mismatch in the amount of inhalation between the time of the CT scan and the procedure. This misalignment has been previously studied and determined to be, on average, 1 mm in the left direction, 1 mm in the superior direction, and 0 mm in the AP direction. In certain embodiments, this error may be acceptable for most guidance needed in structural heart interventions (TAVR, LAA occlusion, TMVR).

In the case that direct image processing methods are not sufficient, sensors may be employed to compensate for cardiac motion since gating can be directly performed from the ECG signal. However, in various embodiments, respiration may need to be done using strain sensors on the chest of the patient to understand when they are in a deep inspiratory phase. In various embodiments, commercial systems with such sensor types may be integrated to perform both of these functions.

In various embodiments, another strategy, may incorporate 4 spherical metal ball markers that are placed on a patient's chest either independently or integrated within a pad. The 4 spherical balls are located at different positions and can be used as fiducial markers when positioned during a CT scan or rotational angiography. When the relative distances of the marker balls are changed due to respiration, those changes can be captured by fluoroscopy during the procedure and used to select the same phase as the CT scan (e.g., deep inspiration) to minimize error in co-registration. This approach is much more general than for cardiac motion and can be applied to any organ system.

Advantages of various potential embodiments: A major factor that influences how transcatheter procedures are developed is how an interventionalist can visualize the delivery of the catheter or cardiac device. Given that CT images are taken prior to many of these procedures, this information may be leveraged to improve visualization during the procedure. Currently, due to limitations in registration speed and detecting 3D orientations, systems simply overlay 2 projections of the 3D images over the 2D fluoroscopy images to provide a frame of reference of where the cardiac tissue is located. Whereas, embodiments of the disclosed system may utilize real-time machine learning algorithms to display both the catheter and cardiac anatomy in a separate 3D rendering that provides quantitative metrics of their relative positions, thus ensuring unprecedented accuracy and precision. For example, during a transseptal puncture, the position and angle of the puncture on the septal wall will be dictated so that entry into the left atrium occurs at the desired orientation. This quantitative feedback will enable analytics of procedures for determining best practices for other interventionalists. Since this technology will improve the accuracy and precision of transcatheter delivery for cardiac devices, it will also enable the development of new procedures and lower the learning curve for existing procedures. Furthermore, the developed guidance system and benchtop models can be used for pre-procedural planning, practicing procedures, and as a teaching tool for residents and fellows; providing a quantitative platform for comparing methods for procedures amongst interventionalists.

A major advantage of this approach is the ability to coordinate a validation study with both experienced and inexperienced cardiac interventionalists to properly evaluate the usefulness of this developed system, both in terms of intra-operative guidance and pre-procedural training. Embodiments of the disclosed image-guidance system are useful not only for LAA delivery procedures, this method is applicable to any transcatheter procedure in which a MRI or CT scan is taken prior to the procedure, and thus has the potential for significant impact on the field of interventional cardiology. The improvements to clinical care will be multi-faceted, including improved patient recovery time, improved patient outcomes, and lowering costs for patients, hospitals, and the general population.

Figure 4:
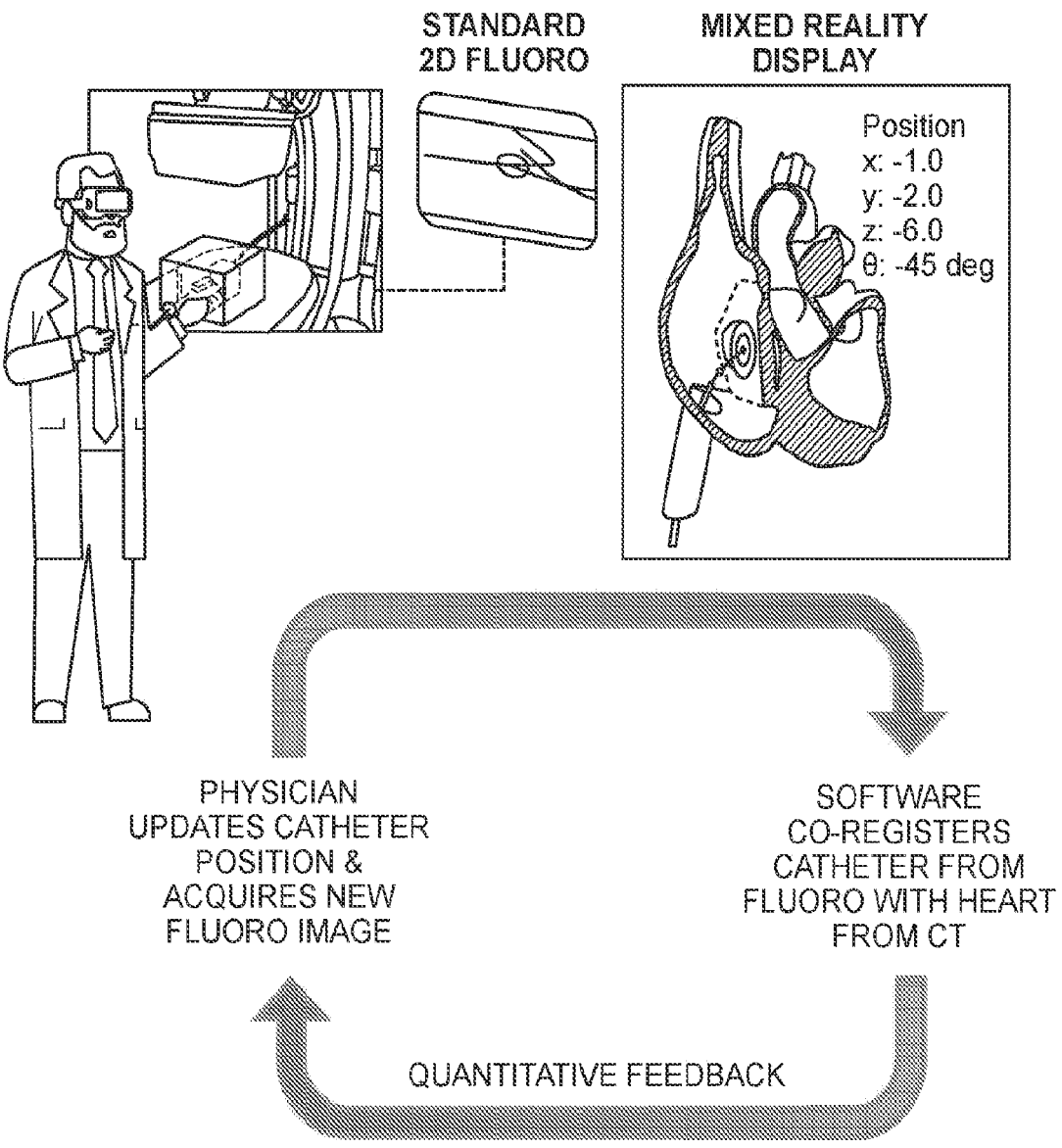
FIG. 4 depicts a schematic of a mixed reality navigation system according to various potential embodiments, in which fluoroscopic image may be converted in real-time to a 3D rendering with quantitative feedback of catheter position and angle.
Figure 28A:
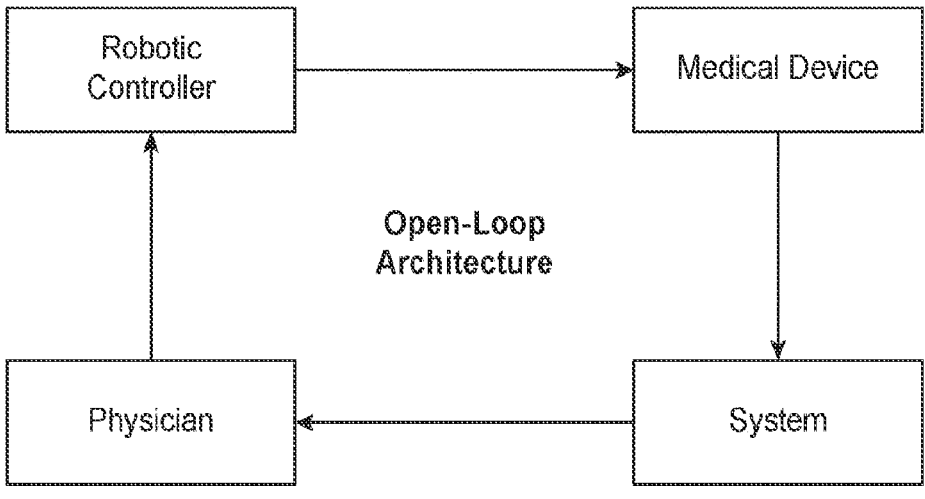
FIGS. 28A and 28B depict open-loop and closed-loop architectures according to various potential embodiments.
Figure 28B:
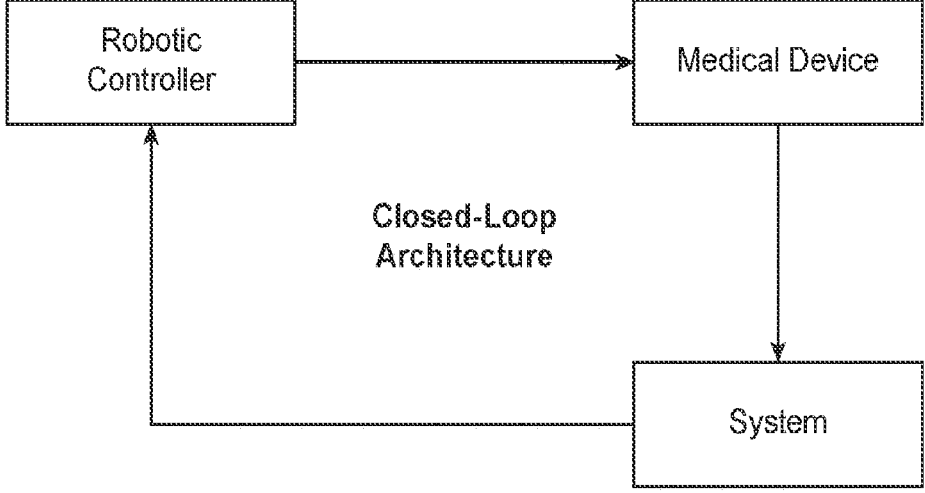

Because various potential embodiments provide real-time quantitative feedback, it naturally lends itself to development of robotic systems. This system can be open-loop (see FIG. 28A), where a human can still guide a robot, which controls the medical device (e.g., catheter's handle), thus, allowing the interventionalist to be remote; either in the next room to avoid unnecessary radiation, or across the world to allow telesurgery by experts. Closed-loop (see FIG. 28B) algorithms will also allow for robotic systems to automatically perform certain procedural tasks pre-procedurally. The disclosed approach may provide inherently safe catheters and other medical devices. In various embodiments of the disclosed approach may wholly (with respect to all steps) or partially (with respect to certain steps) be open-loop and/or closed-loop. In an open-loop system, the user would see the mixed reality renderings and quantitative feedback and make their own decision on how to move and/or deploy the medical device. In certain embodiments, the open-loop system may be similar to the system depicted in FIG. 4 if a robotic component were controlling the catheter handle remotely. If that same robotic controller were automatic, it would be closed-loop. In a closed-loop system, a robotic controller would control the medical device delivery.

Returning to FIG. 1, FIG. 1 illustrates an example system 100 to guide the placement, use, and/or movement of medical devices in subjects according to various potential embodiments. The system 100 can include a guidance system 102 that receives image data from a first imaging device 104 and second imaging device 106. The guidance system 102 can receive other physiological data additional sensors 108 (e.g., EKG data from an electrocardiogram (EKG) device, motion and/or position data, etc.). The guidance system 102 can generate guidance images can include models or images of a medical device co-registered, in real-time, with the models of anatomical targets. The guidance system 102 can transmit the guidance images to the display 110 for display to a user of the guidance system 102.

In various potential embodiments, the guidance system 102 can include a model generator 112 to generate virtual models of the medical device, target anatomy, and fiducial markers. The guidance system 102 can include a segmentation engine 114 to segment the medical device, target anatomy, and fiducial markers from the background or other contents of imaging data. The registration engine 116 can include a registration engine 116 to co-register the image data from the first imaging device 104 with the second imaging device 106. The guidance system 102 can include a motion correction engine 118 to correct for motion artifacts that can be present in the imaging data. The motion artifacts can be generated by, for example, movement of the patient's heart, lungs, or appendages. The guidance system 102 can include a guidance system 102 to generate and output an image that can include a co-registered virtual model of the medical device and target anatomy.

In various potential embodiments, the system 100 can include a guidance system 102. The guidance system 102 can include at least one server or computer having at least one processor. For example, the guidance system 102 can include a plurality of servers located in at least one data center or server farm or the guidance system 102 can be a desktop computer, laptop computer, tablet computer, or other computing devices. The guidance system 102 can include a processor that can include a microprocessor, application-specific integrated circuit (ASIC), a field-programmable gate array (FPGA), other special purpose logic circuits, or combinations thereof.

In various potential embodiments, the guidance system 102 can include a model generator 112. The model generator 112 can be an application, applet, script, service, daemon, routine, or other executable logic to generate computer models of the target anatomy or other components within image data, such as the universal fiducial marker. The model generator 112 can generate the models from image data sets 134. The generation of models by the model generator 112 is described further below. The model generator 112 can receive the image data sets 134 from the first imaging device 104, the second imaging device 106, and/or the sensors 108. The first imaging device 104 can be a computed tomography (CT) device or a magnetic resonance (MR) imaging device. The model generator 112 can receive the image data sets 134 from the first imaging device 104 that include pre-operative images (e.g., CT images). For example, 1 week before an operation, the first imaging device 104 can capture CT images of the patient's heart. The CT images can include a universal fiducial marker, such as the patient's spine. The model generator 112 can receive the pre-operative images and generate the models before the operation involving the patient's heart.

In various potential embodiments, the model generator 112 can generate models for one or more components within the image data sets 134. The models can be 3D, CG models. The model generator 112 can generate a model for the anatomical target based on the pre-operative image data sets 134. The anatomical target can be or can include the heart or other portion of the patient's vasculature. The model generator 112 can generate a model of the patient's spine based on the pre-operative image data sets 134. The guidance system 102 can use the spine as a universal fiducial marker.

In various potential embodiments, the guidance system 102 can include a segmentation engine 114. The segmentation engine 114 can be an application, applet, script, service, daemon, routine, or other executable logic to segment image data from the image data sets 134 from the first imaging device 104 or the second imaging device 106. For example, the second imaging device 106 can be a fluoroscope or electrocardiogram. The segmentation engine 114 can, for example, segment fluoroscopic images. The segmentation engine 114 can segment the fluoroscopic images to segment or otherwise identify a universal fiducial marker (e.g., the subject's spine) and a medical device (e.g., a catheter). In some implementations, the segmentation engine 114 can segment the spine and medical device and generate a mask of the spine and medical device. The mask can be a bit mask. For example, the mask can be an image that includes 0's at locations in the fluoroscopic image that do not include the medical device or spine and 1's at locations in the fluoroscopic image that do include the medical device or the spine. In certain embodiments, in addition or alternatively to a mask, a center coordinate can be generated. The center coordinate may be a pixel that represents a specific region (e.g., the center of mass, or a specific corner) of that structure. The center coordinate could be used to identify a fiducial point for rendering that structure. For example, this could be three coordinate points at the tip, middle, and base of a catheter, such that the rendering of the catheter is performed by connecting those three points with a spline.

In some implementations, the fluoroscope can transmit image data sets 134 to the guidance system 102 that can include a plurality of images captured at different angles. The segmentation engine 114 can segment each of the images captured at the different angles. The segmentation of the spine and medical device from the fluoroscopic image is further described below. The segmentation engine 114 can segment the images of the first and the second modalities using image processing to, for example, identify edges within the images. The segmentation engine 114 can identify objects within the images based on the identified edges. In some implementations, the segmentation engine 114 can use machine learning or computer vision to identify and segment objects from the image data sets 134. The segmentation engine 114 can include a convolutional neural network to identify the objects in the image data sets 134.

In various potential embodiments, the guidance system 102 can include a registration engine 116. The registration engine 116 can be an application, applet, script, service, daemon, routine, or other executable logic to determining a transformation between the model of the universal fiducial marker generated from a first image data sets 134 from the first imaging device 104 (e.g., a CT or magnetic resonance device) and the universal fiducial marker segmented from the image data sets 134 of the second imaging device 106 (e.g., a fluoroscopic imaging device).

In various potential embodiments, the registration engine 116 can use the spine or other anatomical structure as a universal fiducial marker to co-register the coordinate systems of models that the model generator 112 generates from the images of a first imaging modality (e.g., CT images) and the images of a second imaging modality (e.g., fluoroscopic images). For example, since the spine is a rigid object and has a relatively consistent position within the subject, the spine can be used as a universal fiducial marker. The registration engine 116 can generate a transformation that can include scaling factors, rotation factors, and translation factors that enable the guidance system 102 to place the spine and medical device as imaged by the first imaging device 104 and the second imaging device 106 within a single coordinate system. In some implementations, the transformation can be a transform matrix.

In various potential embodiments, the guidance system 102 can include a motion correction engine 118. The motion correction engine 118 can be an application, applet, script, service, daemon, routine, or other executable logic to correct for motion artifacts. In some implementations, movement of the subject can introduce motion artifacts into the image data sets 134 generated by the first imaging device 104 or the second imaging device 106. The movement can include the movement of the subject's chest due to breathing or movement within the subject's chest due to the beating of the heart. The motion correction engine 118 can identify time points when the subject was in the same position of the breathing cycle or heartbeat to capture or analyze images from the first imaging device 104 and the second imaging device 106. In some implementations, the first imaging device 104 can be configured to capture pre-operative image data sets 134 during an inter-beat interval. For example, the first imaging device 104 can be coupled with an EKG device 108 to identify heartbeats and then capture the image data sets 134 between two consecutive heartbeats. The motion correction engine 118 can control the second imaging device 106 to capture image data sets 134 during the same portion of the heartbeat (e.g., the inter-beat interval) or can identify portions of the image data sets 134 captured during the same portion of the heartbeat as the image data sets 134 of the first imaging device 104. For example, the image data sets 134 generated by the second imaging device 106 can include a plurality of images sampled over a predetermined time to form a movie or series of images. The images can be time-locked with the signal from the EKG device 108. The motion correction engine 118 can identify, for example, an inter-beat interval between contractions of the subject's heart in the EKG signal and select the portions of the image data set 134 from the second imaging device 106 captured during the inter-beat interval.

In various potential embodiments, the guidance system 102 can include a display generator 120. The display generator 120 can be an application, applet, script, service, daemon, routine, or other executable logic to generate virtual models that illustrate the real-time position of the medical device within the anatomical target. The display generator 120 can retrieve the transformation data structure 132 from the registration engine 116. The display generator 120 can register the geometry and position of the medical device with the with the model of the anatomical target based on the transformation to generate an image that includes the medical device's real-time position within the target anatomy. The display generator 120 can generate a 2D image that illustrates the real-time position of the medical device within the model of the anatomical target. The display generator 120 can generate a 3D image that illustrates the real-time position of the medical device within the model of the anatomical target. In some implementations, the display generator 120 can receive a user input to update the rotation, pan, zoom, or view of the 3D image. For example, the user can click and drag the displayed model of the anatomical target with a mouse, or gesture on a touchscreen, to provide a different view of the 3D model of the anatomical target.

In various potential embodiments, the guidance system 102 can include a database 122. The database 122 can be stored in device memory or other suitable storage for computer program instructions and data. The memory can include all forms of non-volatile memory, media and memory devices, including semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry. As described above, the guidance system 102 can store model of the spines 124, the model of the targets 126, the mask of the spines 128, the mask of the devices 130, transformation data structures 132, and a training library 136 in the database 122.

In various potential embodiments, the model of the spine 124 and the model of the target 126 can be generally referred to as models. The models can be computer generated models. For example, the models can be computer-aided design (CAD) models that represent that anatomy of a subject. The models can be data structures that can include data indicating the 3D geometry and position of an object. For example, the data structure can be in an STL or other file format for storing 3D data. The mask of the spine 128 and the mask of the device 130 can generally be referred to as masks. The masks can be a data structure that indicates the location of an object (e.g., the spine or medical device) within, for example, a fluoroscopic image. The mask can be a matrix the same size as the fluoroscopic image that can include 0's at the position of the pixels in the fluoroscopic that do not include the object and 1's at the position of the pixels in the fluoroscopic that do include the object. The guidance system 102 can store transformation data structures 132 in the database 122. The transformation data structure 132 can be a data structure that includes a matrix of the scaling factors, rotation factors, and translation factors for transforming register the image data sets 134 from the first imaging device 104 with the image data sets 134 of the second imaging device 106. For example, the matrix can enable the location or coordinates of the spine in a fluoroscopic image (as identified by a mask of the spine 128) to be transformed into the coordinate system of the model of the spine 124. The guidance system 102 can store image data sets 134 in the database 122. The image data sets 134 can be images captured by the first imaging device 104 or the second imaging device 106. The image data sets 134 can be CT images, MR images, fluoroscopic images, or other types of image data.

In various potential embodiments, the database 122 can include a training library 136. As described above, the segmentation engine 114 and the registration engine 116 can include a machine learning module, such as a convolutional neural network. The training library 136 can include training data for training the machine learning modules of the segmentation engine 114 and the registration engine 116. For example, the training library 136 can include image data sets 134 that are pre-segmented or include masks to identify the objects within the training data. The training library 136 can include pre-segmented fluoroscopic images, pre-segmented CT images, and/or pre-segmented magnetic resonance images.

In various potential embodiments, the system 100 can include a first imaging device 104. The first imaging device 104 can be a medical imaging device to capture pre-operative images of the subject and the subject's anatomy. For example, the first imaging device 104 can capture pre-operative images of the patient's heart and spine. The first imaging device 104 can be a medical imaging device capable of capturing 3D images of the subject. For example, the first imaging device 104 can capture a plurality of images (or "slices") along an axis of the subject. The plurality of slices can be stitched together to form a 3D volume. The first imaging device 104 can be a CT imager or a magnetic resonance imager, for example. The first imaging device 104 can capture images that are provided to the guidance system 102 as image data sets 134.

In various potential embodiments, the system 100 can include a second imaging device 106. The second imaging device 106 can be an imaging device that has a different imaging modality than the first imaging device 104. For example, the second imaging device 106 can be a fluoroscopic or echocardiographic imaging device. The second imaging device 106 can capture images that are provided to the guidance system 102 as image data sets 134. The second imaging device 106 can capture intra-operative images of the patient. The intra-operative images can include the spine and the medical device (e.g., a catheter). In some implementations, the second imaging device 106 captures 2D images. The image data sets 134 from the second imaging device 106 can include metadata. In some implementations, the fluoroscopic imaging device can be mounted on a C-arm such that the fluoroscopic imaging device can capture images from a plurality of different angles. The metadata can include an indication of the angle at the fluoroscopic imaging device captured the image.

In various potential embodiments, the system 100 can include a display 110. The guidance system 102 can display the generated models to the user via the display 110. The display 110 can be a cathode ray tube (CRT), a flat-panel device such as a liquid crystal display (LCD), a projection device, or some other mechanism for creating a visible image. In some implementations, the display 110 can be or can include an augmented reality (AR), virtual reality (VR), and/or mixed reality (MR) system. For example, the display 110 can be integrated into glasses or other wearables with an integrated computing device. The display 110 can generate images overlaid on the user's field of view. For example, the display 110 can include one or more headsets, usable by one or more clinicians, such as VR headsets, AR headsets, MR headsets, wearable devices comprising heads-up-displays, and/or area displays.

The guidance system 102 can include one computing device, or multiple computing devices that are co-located or remotely-located and in wired or wireless communication with each other via any suitable communications networks and protocols. Similarly, the first imaging device 104, the second imaging device 106, the sensors 108, and the display 110 may each comprise one or more computing devices and sensors that are co-located or remotely-located and in wired or wireless communication with each other and/or with the guidance system 102 (or components thereof). It is noted that any two or more elements or components in FIG. 1 can be combined, any single element or component can be split up into two or more components, or otherwise the functionality of the elements of or components in FIG. 1 can be reconfigured into different components than the ones depicted in FIG. 1. A system or device may be deemed external to another system or device if the two communicate over a network via wired or wireless communication, can operate independently, or are not in the same housing. A system or device may be deemed remote to another system or device if the two are not in each other's physical presence and thus not physically accessible, such as systems and devices that are deemed to be in the "cloud." Systems and devices may be deemed to be local or co-located if they are in close proximity to each other or otherwise in each other's physical presence. A device or system that is external to another device or system may be local or remote with respect to the other device or system. External systems and devices may be computers with the ability to perform local or wireless data transfer.

FIG. 12 provides a general scheme of various embodiments of the disclosed guidance system, where a clinician manipulates a catheter and sees a 3D rendering with quantitative feedback floating in mixed reality, next to the standard fluoroscopy monitors. (Ref. [1] includes additional details.) In FIG. 12: "Cath lab" refers to a catheterization (or other) room to perform a medical procedure; "MR Headset" (mixed reality headset) is used to visualize the renderings of the medical device and patient anatomy in 3D (e.g., display 110); "Wireless MR Rendering Data" refers to data from software to render mixed reality environments sent to the MR headset for visualization; "Wireless EKG and Respiration Signal" refers to data from external sensors (e.g., sensors 108) to track heart contraction phases and respiration phases to perform motion-compensation; "Cath Lab Side Room" refers to a room adjacent to the procedure room (e.g., the catheterization room) to store computer and hardware equipment (e.g., computing devices that communicate with and obtain data from first and second imaging devices 104, 106); "Mixed Reality View" refers to a floating mixed reality rendering projected in the MR headset; and "Video Grabber" may obtain images from a computing device (e.g., "Cath Lab PC" (personal computer)) that, for example, acquires physiological images from imaging devices for rendering or other processing by one or more computing devices (e.g., "Research Laptop") for display. The image tracking aims to detect and co-register the catheter's 3D position using bi-plane C-arm X-ray fluoroscopy and provide a 3D trajectory as quantitative feedback, as illustrated in FIGS. 13A-13D.

Mono-Plane Fluoroscopy Tracking

Various potential embodiments provide an approach for calculating a z-dimension of objects from a monoplane fluoroscopic image by leveraging deep learning models. Previous approaches used analytical calculations based on automated feature recognition algorithms (see Refs. [2, 3]). However, they have shown poor accuracy, and therefore more sophisticated approaches are necessary. The disclosed approach can leverage, for example, a vast amount of data to train models. In example embodiments, the data may include clinical images accessible through, for example, a catheterization lab that takes fluoroscopy images, such as through Weill Cornell Medicine and NewYork-Presbyterian.

In various potential embodiments, the disclosed approach employs deep learning to leverage patterns in the fluoroscopic image to accurately calculate an object's z-position from a single angle projection. FIGS. 14A-14D depict a deep learning model that can predict the z-position of an object, in this case a sphere, with an average accuracy of 0.12±0.11 mm using only a monoplane fluoroscopic image (see FIG. 14D). The ground truth value of the z-dimension used to train this regression-based model may be calculated analytically from the positions of the sphere in the bi-plane image (see FIG. 14B). Such a model when trained with images from a catheter will have similar or better accuracy, since it will be trained with a higher number of images and its more complex shape should have more imaging features for the model to recognize.

Figure 15B:
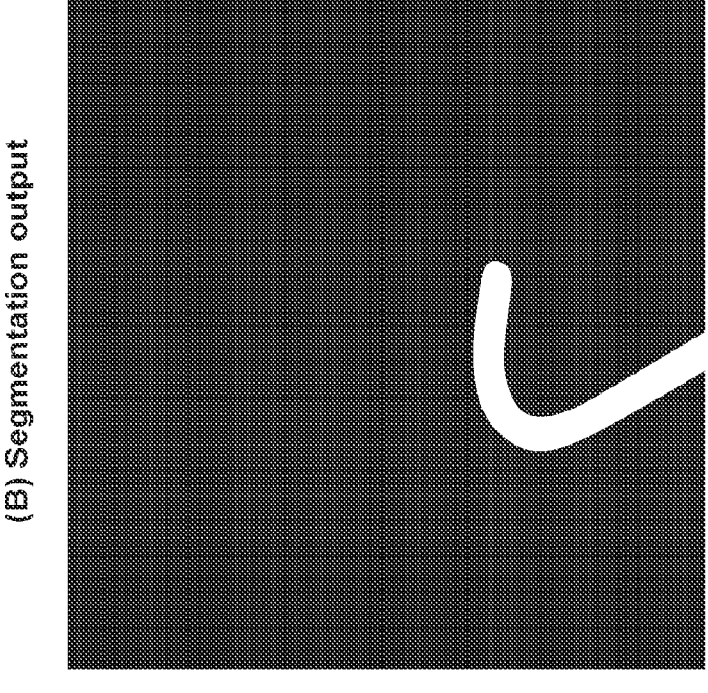
FIGS. 15A-15D provide illustration of sequential feature engineering steps to prepare training datasets for a deep learning regression model, according to various potential embodiments. From 15A, obtaining Fluoroscopic Image, FIG. 15B, segmenting the catheter using U-Net architecture, FIG. 15C, performing additional post-processing, FIG. 15D, detecting the points of interest on catheter.
Figure 15A:
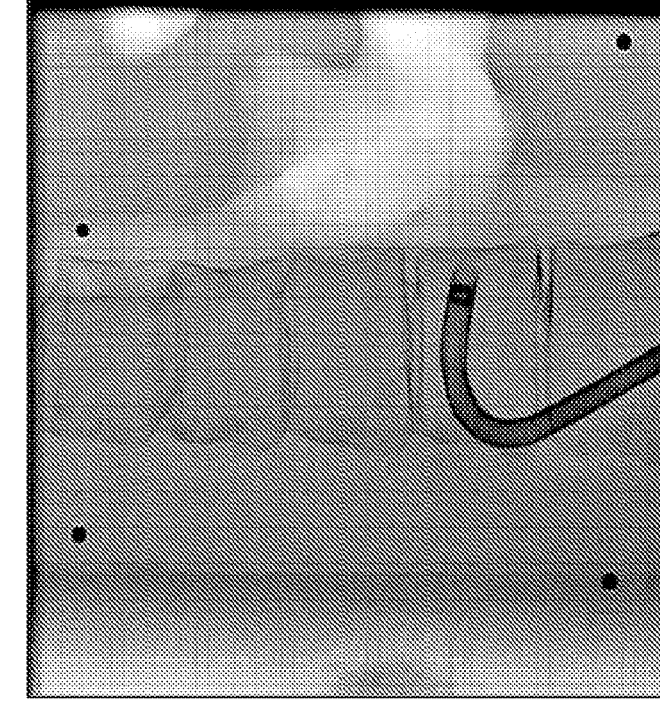
Figure 15D:
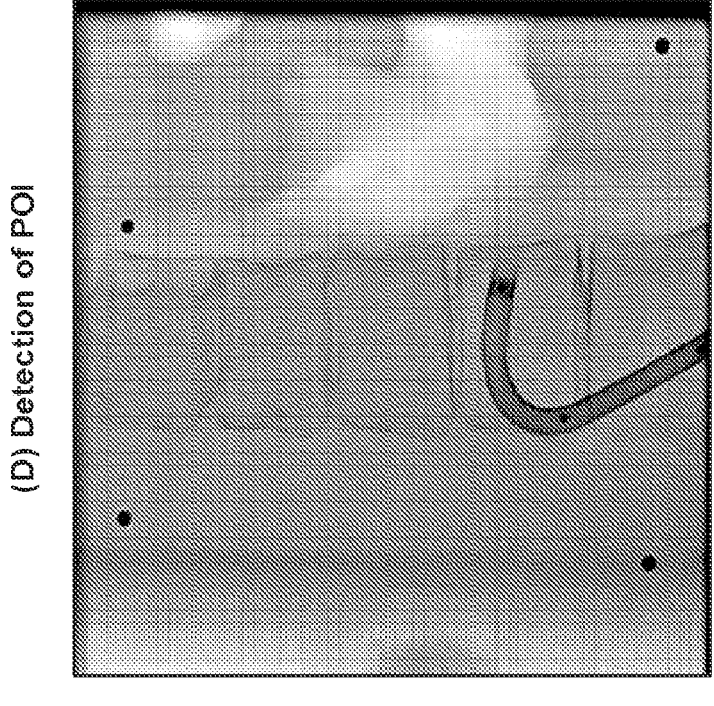
Figure 15C:
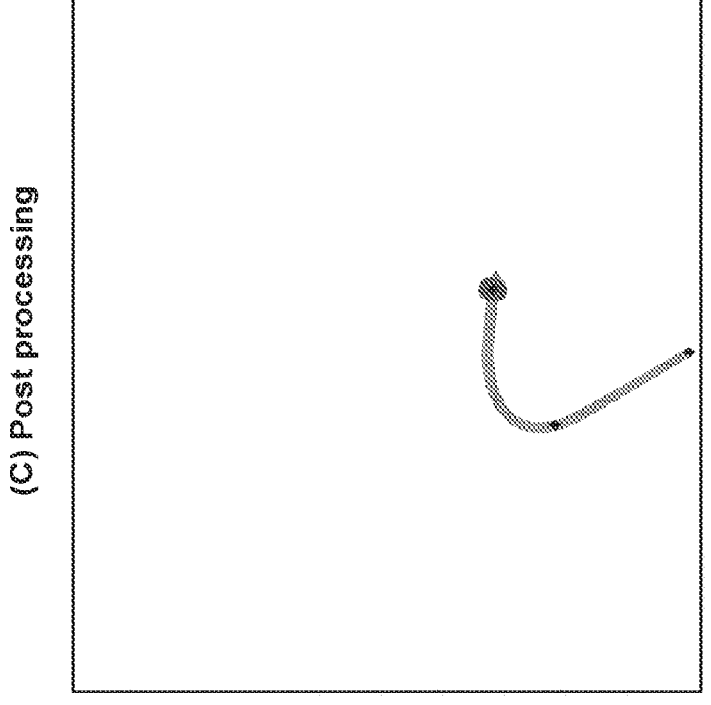

In various embodiments, for feature engineering, first, the approach may leverage the U-net model (see Ref. [4]) to segment the catheter (see FIGS. 15A and 15B), followed by post-processing to detect the radiopaque marker, middle and beginning of the catheter (see FIG. 15C). From this post-processing, three points of interest (POIs) on the catheter's image are selected (FIG. 15D), which will be used to define the spline for rendering the catheter in mixed reality. With the detected position of the catheter (x, y) and (x', y') and the known rotation angle, the third dimensional positions (z, z') are solved from the equation in FIG. 16B. In various embodiments, the ground truth value of the z-dimension for the POIs and only the AP fluoroscopic image will be used to train the CNN regression model in a supervised manner, (FIGS. 16C and 16D). Optimal hyperparameter settings often differ for different datasets. As a result, hyperparameter tuning algorithms such as Random Search and Bayesian Search may be employed in an existing CNN regression model. The Bayesian Search considers the previously known knowledge (from the trained model on radiopaque spherical markers) and searches only those hyperparameter combinations that will increase the model's performance. An example deep learning (DL) model (see FIG. 16D) consists of 1 input layer, 4 convolution blocks, 3 max pooling layers, 1 fully connected layer, and 1 regression layer. Each convolution block consisted of 2 repetitions of two-dimensional convolution, batch normalization, rectified linear unit (ReLU) activation layers. An adaptive moment (ADAM) estimation algorithm was used for training the CNNs. The loss function was a mean-squared-error (MSE). The following hyperparameters of the developed CNNs were Bayesian-optimized with a coarse-to-fine search filter size and number of filters for each convolution layer, the number of neurons of the first fully connected layer, and initial learning rate. An early stopping rule was applied with 200 epochs. The Learning Rate Schedule and Time-Based Decay were both used for the DL model, and the rate was scheduled to drop every 10 epochs by a factor of 0.9. Finally, the performance of the regression DL model was evaluated by computing mean absolute error (MAE) and the accuracy of the z-position prediction was determined to be below 2 mm (see FIG. 14D). The ground truth value of the z-dimension used to train this regression-based model was calculated analytically from the sphere's positions in the bi-plane image (see FIG. 14B).

Dynamic Heart Phantom

Figures 17A, 17B, 17C, 17D:
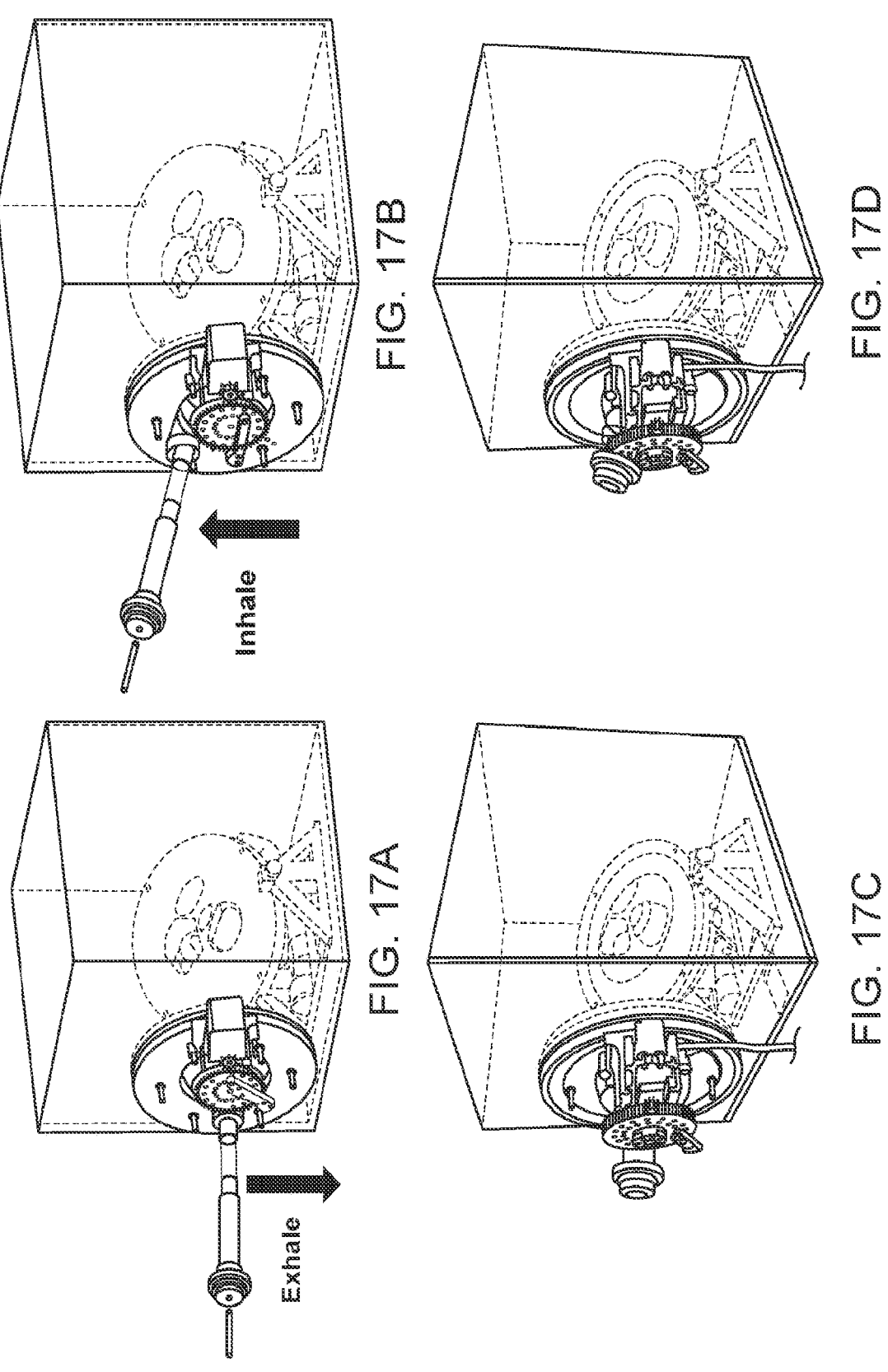
FIGS. 17A-17D depict a dynamic heart phantom according to various potential embodiments.

In various embodiments, to train deep learning algorithms and optimize the system in an efficient manner, a way to acquire large sets of data may be employed. 3D printing may be used to build a dynamic phantom model (see FIG. 17), that recapitulates cardiac respiratory motion, to perform mock procedures and gather ground truth images. With actual fluoroscopic images from these patients, the disclosed approach may digitally replace the background images before training on deep learning algorithms to have realistic background features. Alternatively, the approach may obtain clinical bi-plane images to maximize the translatability of this approach. In an example, a CT scan may be employed to 3D print a patient-specific phantom containing the atrial anatomy and a spine, by which the 3D position of the catheter may be determined using bi-plane imaging (see Ref. [5]). In certain embodiments, ventricular and atrial contractions are not recapitulated since in this application, motions compensation for contractions is simply gated and therefore not needed to be mimicked.

Motion-Compensation

The motion of the heart occurs due to both respiration and contraction, and therefore, will not always be in the same position as displayed in the CT scan, which can lead to error in the co-registration of the position of the catheter relative to the heart. Embodiments of the disclosed approach decouple these two motions and provide gating for the high-frequency motion due to contractions and provide estimated compensation for the low-frequency motion due to respiration. Both motions may be tracked in real-time using wireless sensors that can communicate with the research laptop (or other computing device) performing the deployment of the inference of the deep learning model. Contractile cardiac motion during image acquisition (X-Ray, CT, PET) is conventionally monitored using electrocardiography (ECG) gating, which has a strong, established position in clinical settings (see Refs. [6, 7]). ECG gating may be based on R waves' detection and the subsequent division of RR intervals into eight to sixteen frames. Our system will leverage this standard approach to gait the MR display of quantitative measurements to only instances that the fluoroscopic image temporally aligns with the phase of the CT scan. In certain embodiments, doing so will ensure that the geometric deformations of the heart are at a minimum, and thus, real-time tracking of the catheter tip to a target position is optimal. For compensating respiratory induced motion of the heart, certain embodiments may track the chest's motion derived from a commercial respiratory effort transducer (e.g., BioPack TSD201) as surrogate signal. During pre-operative CT acquisition, a patient may be told to hold their breath at both full inhalation (DIBH) and full exhalation during two different acquisitions scans. The same respiratory effort transducer may measure the chest circumference, setting the upper and lower bounds of the surrogate signal. Certain embodiments may segment the heart and spine at each respiratory phase, as shown in FIG. 18A. Next, physicians may select the target points at each respiratory phase (see FIG. 18B). During the procedure, the signal derived from the patient's chest motion using the commercial respiratory effort transducer may be used to interpolate the motion of the target points' as they travers between the two bounds of the respiratory phase, as illustrated in FIG. 18C. Although such an approach may provide perfect motion-compensation (since respiratory motion is not a rigid transformation), in various embodiments the needed accuracy for structural heart cases (<5 mm) can be achieved using this approach.

Deep Learning-Based Co-Registration Using the Spine

Figure 19A:
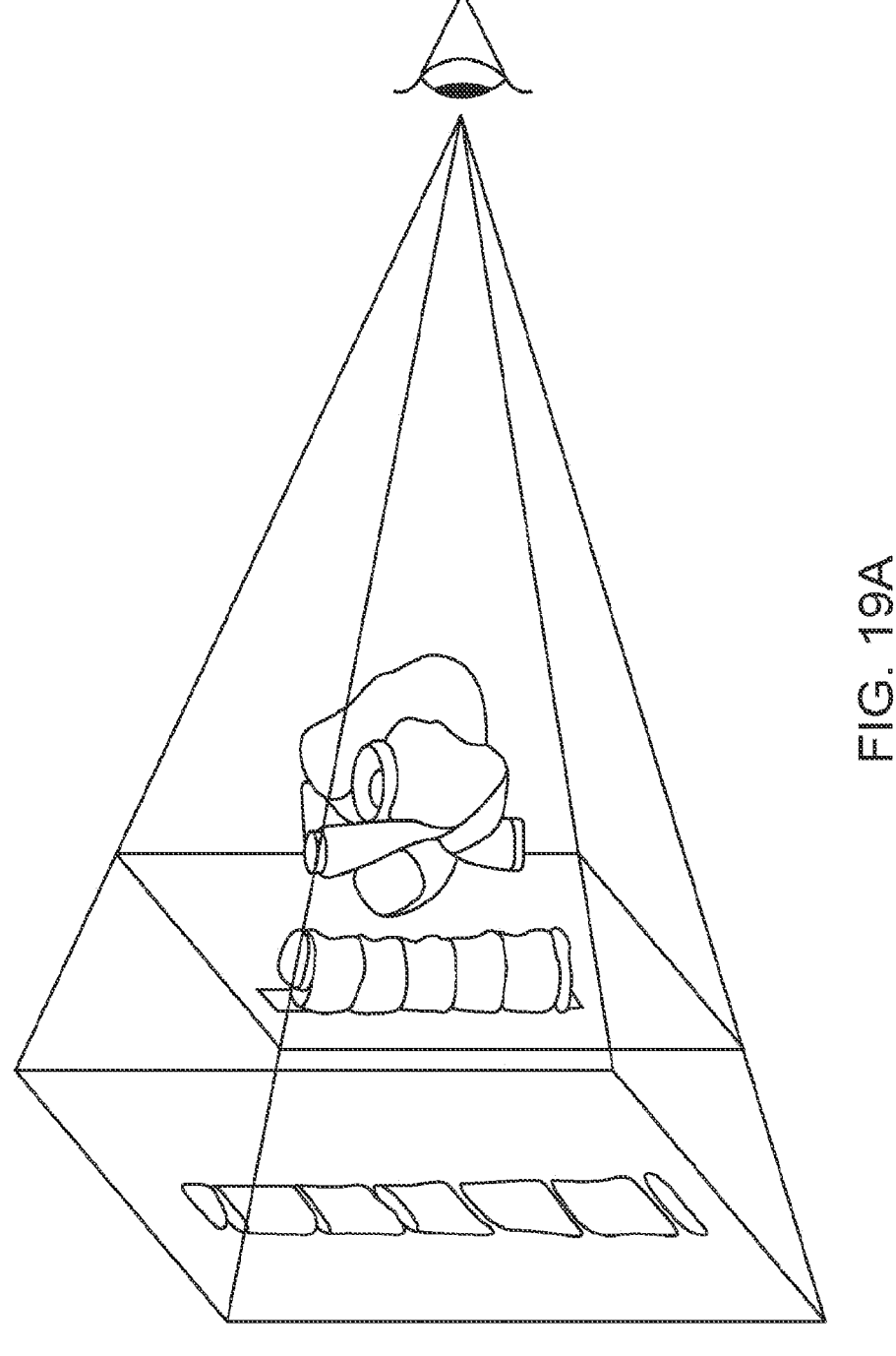
FIGS. 19A-19E depict co-registration using spine according to various potential embodiments.
Figure 19B:
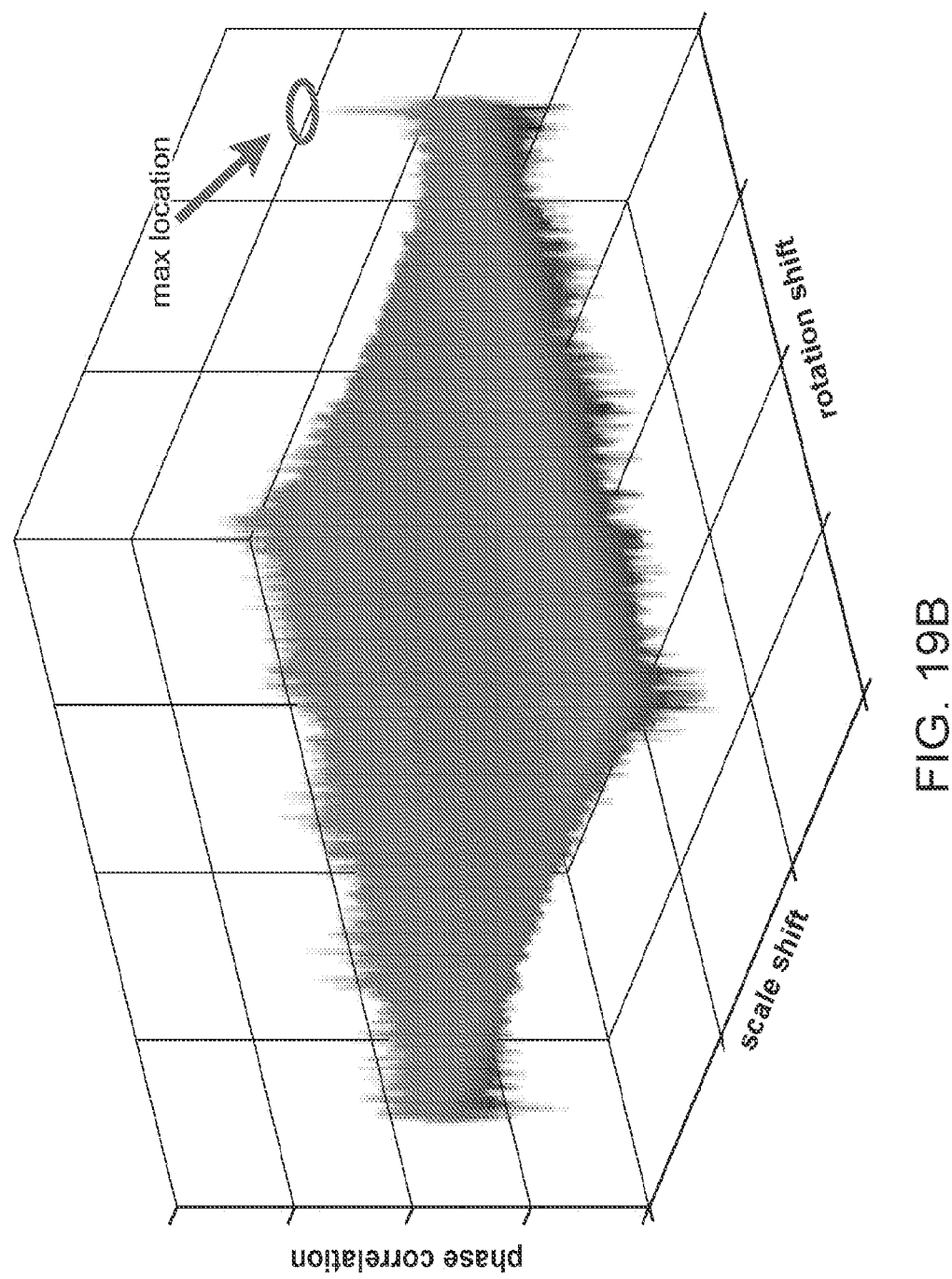
Figures 19C, 19D, 19E:
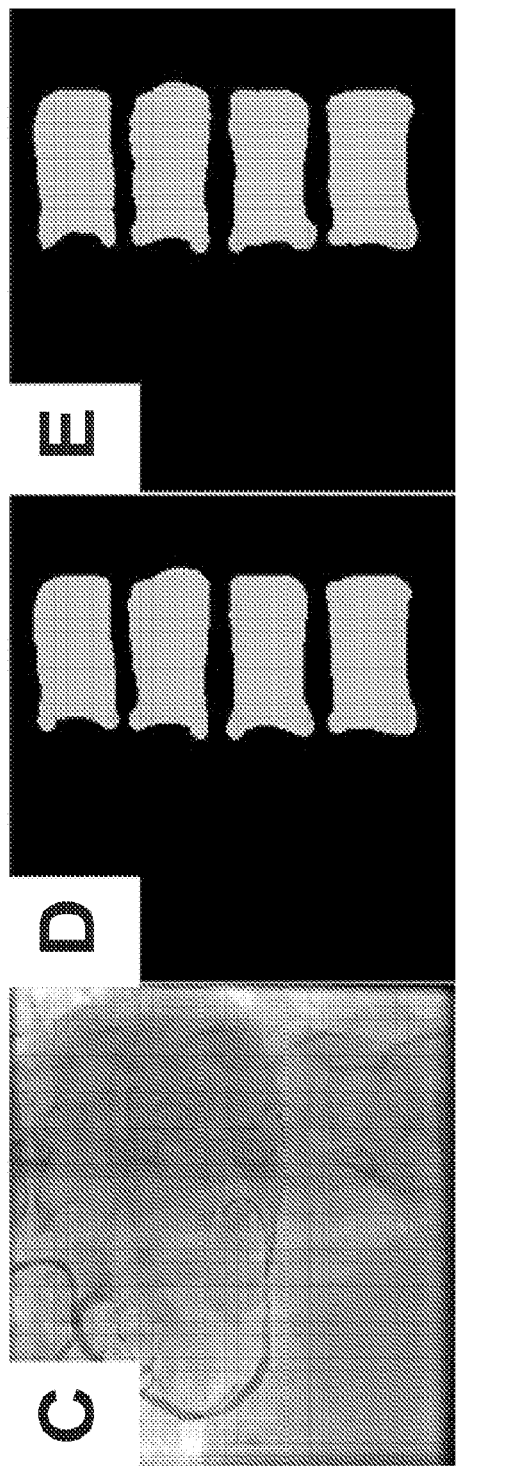

In various embodiments, a key step in this system may be to co-register the catheter with the CT-segmented heart. The spine may be used as an intrinsic fiducial marker (see Ref [5]). This method has shown that the spine can be used to perform 2D to 3D co-registration by finding the maximal overlap between a projected 2D image generated from the segmented 3D spine from a CT scan with the 2D real-time fluoroscopic image of the spine (see FIGS. 19A and 19B). However, various embodiments may use deep learning models to automate the spine segmentation (e.g., U-net), which can work well (see FIGS. 19C to 19E). The CT and flouroscopic images obtained may be manually labelled for the spine and catheter. This may serve as the ground truth for supervised CNN models. These ground truths together with the original images may be fed into the U-Net model for segmentation of the spine and catheters from the fluoroscopic images. Similarly, a variant of U-Net architecture called 3D U-Net may be used to perform 3D segmentation of the spine and heart from the volumetric CT scans. In certain embodiments, a patient data set may be divided into 3 parts: (1) training set (60% of patients), (2) validation set (20% of patients), and (3) testing set (20% of patients). The training and validation sets may be used during model training. The testing set may be used for model evaluation at the end of the model training. The performance of the model may be assessed on the testing set by Dice coefficient and overall computational time for generating spine and catheter masks. Once segmentations are done, 4 centroid points in the vertebrae may be targeted to serve as fiducial markers for the affine transformation steps needed to perform the co-registration (see Ref. [9]).

Proposed Software and User Interface Thereof

In various potential embodiments, 3D renderings may be displayed on 2D screens, augmented reality glasses, and mixed reality headsets. Pre-procedural planning software may be designed to allow for specific targets to be dictated and voice commands customized. A survey of cardiac interventionalists may be used to determine which options should be made available based on personal preference, integration in the catheterization lab, and cost. Risk assessments and validation testing may be performed based on feedback from regulatory agencies (such as the U.S. FDA (Food & Drug Administration). In various embodiments, three mixed reality scenes and associated user functions may be provided for each stage of the intervention, including pre-operative, intra-operative, and post-operative. 3D renderings may be displayed on 2D screens, augmented reality glasses, and mixed reality headsets as deemed suitable. Features and sequential steps of potential embodiments of the software are shown in FIG. 20, where a physician starts selecting the relevant stage of the intervention.

Pre-procedural planning (preoperative) software. In various potential embodiments, the pre-operative software will be designed to allow for specific targets to be dictated and voice commands customized. This will allow use of customize voice, gesture, and gaze tracking as interventionalist input continues to progress, rendering more intuitive control methods. In potential embodiments, first, the physician loads the CT scan and the software's backend automatically segments the 3D structure of the heart. Next, the physician sets the expected steps that will be taken in the intervention. Then, the physician continues by placing the target points and determining their corresponding orientation for each of the two phases of the respiratory cycle. The physicians may be asked to define the level of accuracy required for each target to optimize for needed precision for that procedure. Then, physicians may input descriptions for that action/step in the procedure, if needed, which will allow for higher-level patient-specific tailoring. Finally, the physicians may review and save the preoperative file. Additionally, the software may provide several additional features, such as cross-section views, angle of projections, and voice command features, enabling a more intuitive control and experience. Once the pre-operative file is available, it could potentially be displayed in MR and allow the physicians to discuss with a patient during a consultation.

Intra-operative software. In various embodiments, the physician may begin by loading the saved pre-operative file in the intra-operative module of the software, followed by acquiring fluoroscopic images (at two different angles for bi-plane method, or at one angle for the monoplane method). In certain embodiments, the file may be pre-loaded or automatically loaded upon completion of a prior relevant or detection of another user input indicative of the need for loading of the file. The hardware of the system (e.g., frame grabber) may allow the fluoroscopic images to be uploaded into the intra-operative software in real-time without going through any encrypted hospital servers or storage systems. The software's backend may co-register the fluoroscopic images and CT scan in a single coordinate system by using the spine. Once co-registration is complete, the software's backend starts tracking the catheter's position, followed by reading the ECG signal and strain-sensor signal to interpolate motion compensation due to cardiac and respiration, respectively. The software's front-end may render a catheter in the headset (e.g., a Microsoft "HoloLens" headset). The relative position of the catheter's tip to the target in that step of the procedure may be measured. If within the accepted accuracy, the software indicates to proceed to the next procedural step; if not, the software may ask the physician to return to step 2, as shown in FIG. 20. If all procedural steps are performed, the physician may save the intra-operative file and exits the program.

Post-operative software. In various potential embodiments, the real-time data gathered in the intra-operative file can provide a basis to establish effective standardized metrics for specific steps of a transcatheter procedure. Such data can be used as a self-assessment and quality improvement for the interventional cardiologist, accompanied by the necessary comparison with internal and/or national benchmarks. Furthermore, reviewing post-analysis results and implementing an improvement plan ensures the sustainability of the ongoing cyclic process's performance.

Software's frontend framework and Implementation. In various embodiments, the frontend may be developed using any suitable platform. In an example embodiments, the software's frontend may be developed in the Unity game development platform (Unity 2018.2.9f1) and C# visual studio (.NET Framework). The software's backend may be developed in, for example, TensorFlow/Keras framework using Python2 as described earlier in C.2.2.d. To implement deep learning models into Unity/C# and mixed reality toolkit (MRTK), once machine learning training is complete, the trained model may be converted from Keras (.h5 file) into an Open Neural Network Exchange (ONNX) file that is read into Unity using Tensorflow Sharp. Various embodiments may employ Unity's new Entity-Component-System architecture, along with a Job System and Burst Compiler. From MRTK, various embodiments may implement different features and packages, including camera systems, cross-platform support, multi-scene systems, rendering, and UX (user interface) building blocks. These features may be integrated into the software's frontend, ensuring intuitive design, robust performance, and a smooth experience for the interventional cardiologist.

Physician evaluation and feedback. In various embodiments, a key factor in the iteration of the user interface and user experience is to get broad feedback from physicians or other users. The disclosed approach may systematically obtain feedback by having a review session on a periodic basis (e.g., weekly, monthly, quarterly, or annually). Responses to the system may be recorded in a written survey that is generated before meetings. Both quantitative scoring and qualitative comments may be obtained to provide objective directions for iterations of the system.

Coordinate Regression Network

In various embodiments, one or more of the below models may be employed for tracking of medical devices (or components thereof) relative to organs or other tissues during various medical procedures. Details of example models are presented and their performance compared for catheter tracking and the application of landmark localization in X-ray fluoroscopy imaging.

(A) Convolutional layers+Fully connected layers (Conv+FCN).

(B) Localizer Network (Loc-Net) (Conv+COM).

(C) Heatmap.

(D) U-Net+Postprocessing.

Various embodiments highlight the efficacy of implementing more max-pooling layers in Conv+FCN models, and employ techniques to address or work around the high dependency of the fully connected layer weights on the spatial distribution. Additionally, in various embodiments Unet+COM may be superior over U-Net+Postprocessing. In various embodiments, the center of the mass layer could boost the performance over a heatmap regression method, while simultaneously yielding more interpretable heatmaps. The pros and cons of implementing each model for tracking a catheter's position in an X-ray fluoroscopy image in a 3D printed heart phantom will be discussed.

Figure 21A:
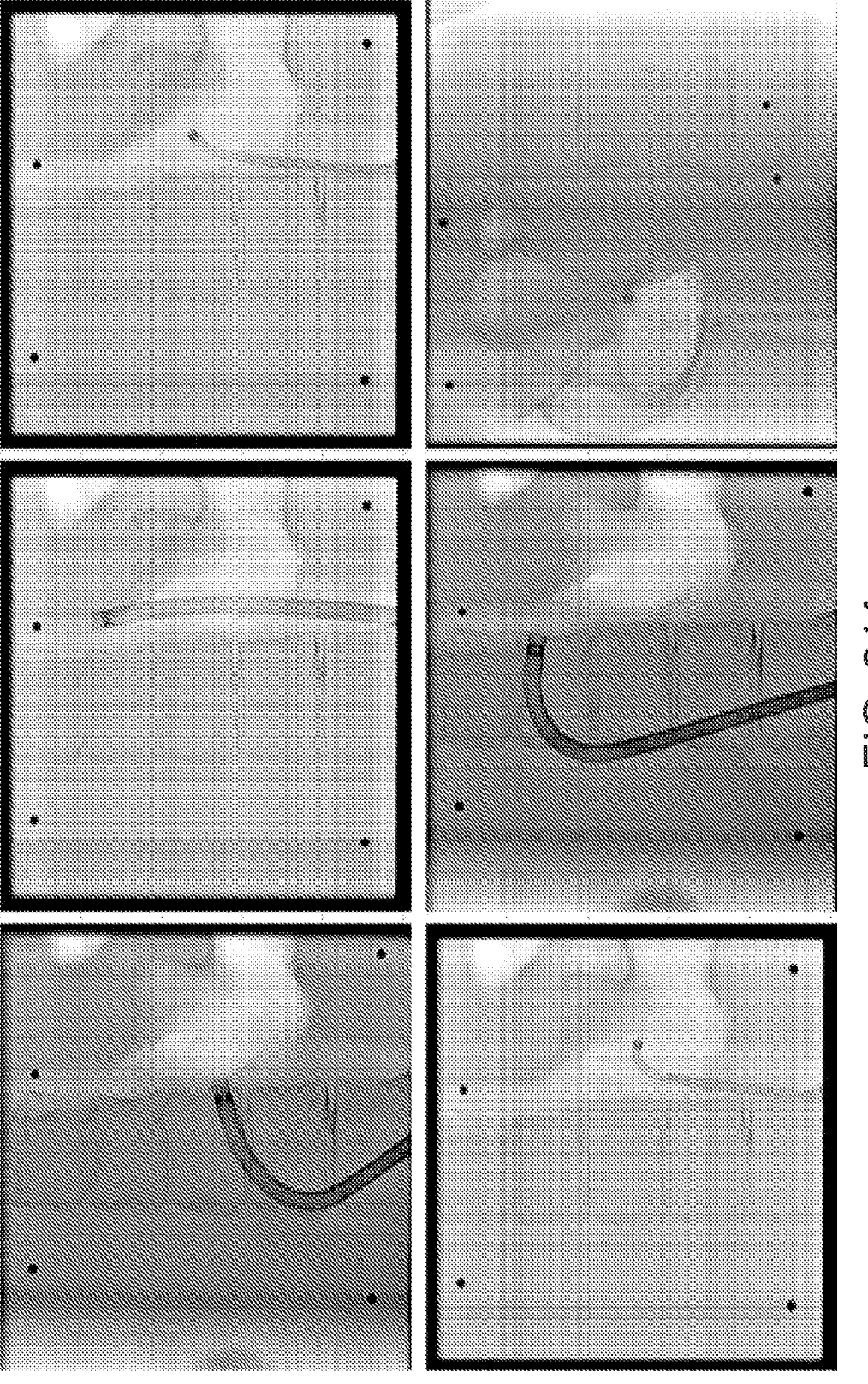
FIGS. 21A and 21B provide example fluoroscopic image datasets of various catheter sizes and configurations within the patient-specific 3D printed model, according to various potential embodiments. The opacity of the catheter, the tip's radiopaque marker, the catheter size, brightness, field of view, the angle of projections, and image artifacts all vary among the entire datasets.
Figure 21B:
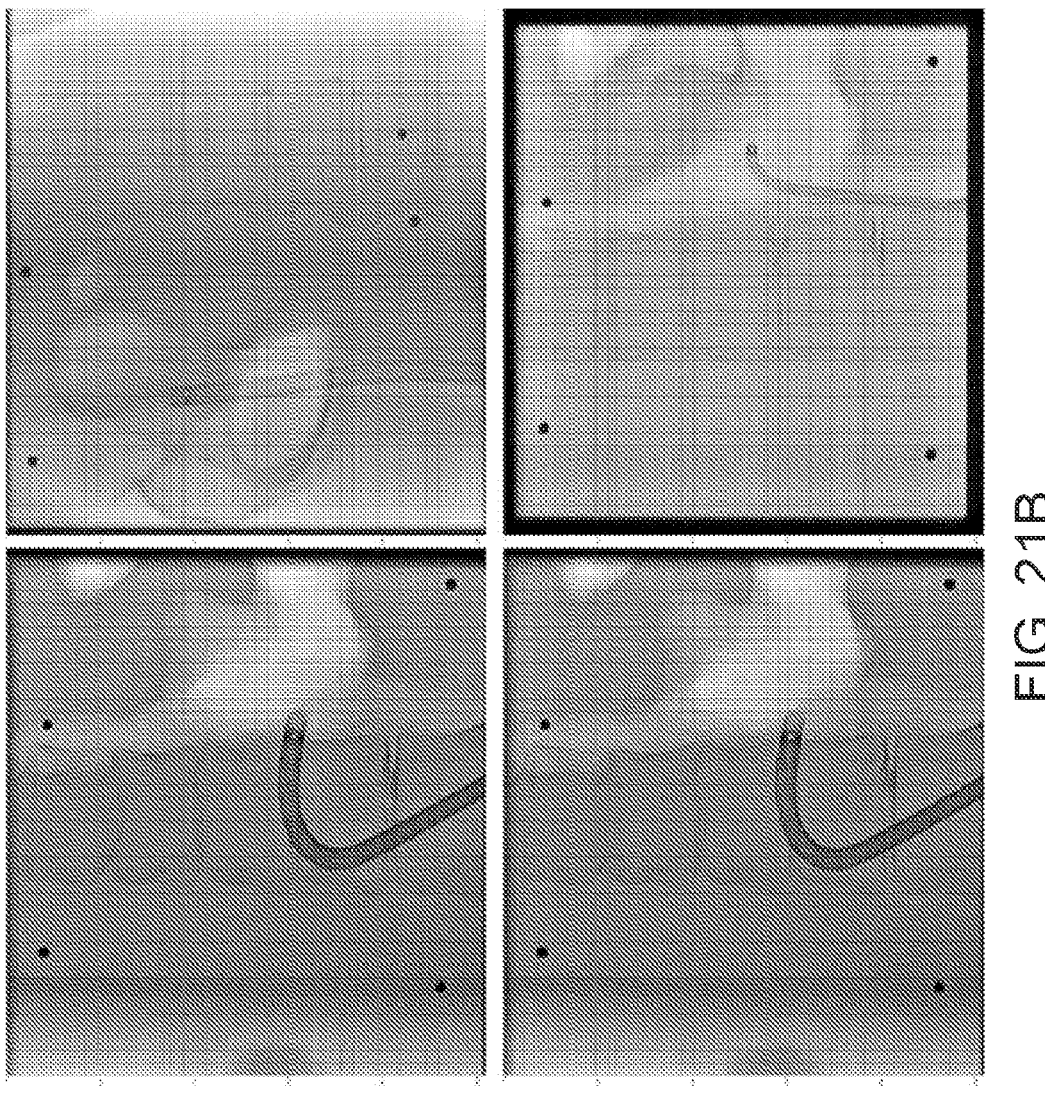

Problem description. A primary target for the application of landmark localization in X-ray fluoroscopy imaging involves the realm of catheter tracking for congenital heart disease (CHD). With the development of catheter techniques, percutaneous interventions have replaced some forms of surgery but also extended the therapeutic arsenal. Nevertheless, both simple and complex CHD typically manifest in unique anatomies that are difficult to study with conventional catheterization techniques. Placing the catheter is complex and requires high expertise to control and navigate as the blood vessels to which the catheter should be inserted are not visible without a contrasting agent. Moreover, the narrowed or blocked blood vessels are not visible even when the contrast agent is used. The size of the catheters to be inserted during the procedures is made by balancing the needs to opacify the coronary arteries and cardiac chambers adequately, to have sufficient catheter manipulation, limit vascular complications, and permit early ambulation. Although the larger catheters enable greater catheter manipulation and excellent visualization, the most commonly used catheters (4F to 6F) facilitate earlier ambulation after catheterization and generally provide adequate visualization. However, smaller catheters require the more excellent technical skill of manipulation and have lower flow rates. Thus, their use in tortuous anatomy, large body habitus, or high coronary flow states (e.g., aortic regurgitation) could be restricted. To this end, various embodiments created fluoroscopic image datasets of various catheter sizes and configurations within the patient-specific 3D printed model, shown in FIG. 21. All fluoroscopic images for training CNNs were acquired during the mock procedures in the catheterization lab at Weill Cornell Medicine/New York Presbyterian Hospital. The datasets comprise 530 paired bi-plane images pertaining to the maneuvering of a catheter (OSCAR Deflectable Steerable Guiding Sheath, Destino™ Twist) within the patient-specific 3D printed model. As can be seen, the opacity of the catheter, the tip's radiopaque marker, the catheter size, brightness, field of view, the angle of projections, and image artifacts all vary from one image to other, ensuring a balanced dataset representing catheterization for CHD. Additionally, four fiducial markers (black circles), shown in the fluoroscopic image, were used for the co-registration of bi-plane images in a single coordinate system.

Figure 22:
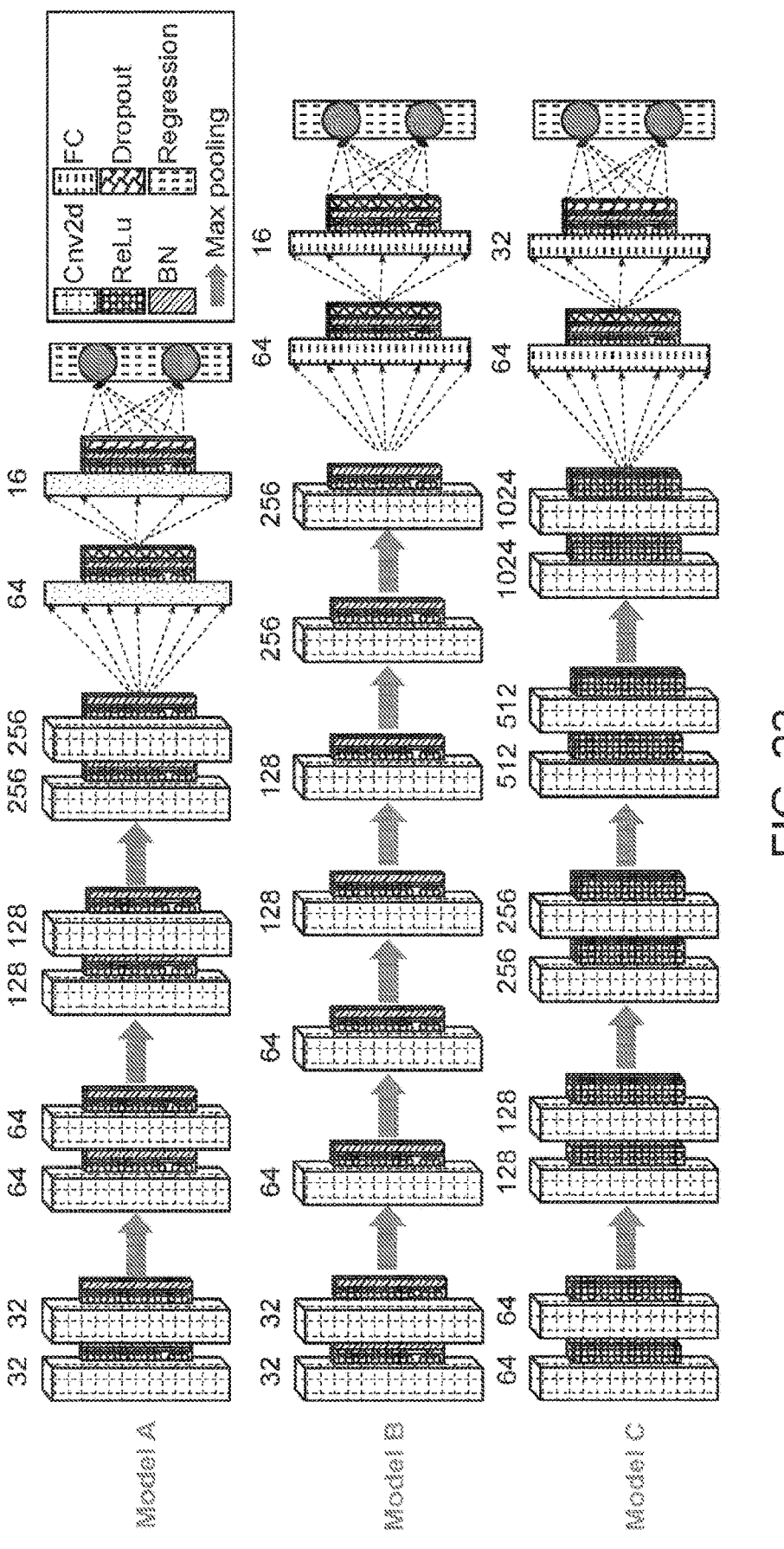
FIG. 22 provides architectures of networks for different assemblies of CNNs (convolutional neural networks or ConvNets) and FCNs (fully convolutional networks), according to various potential embodiments.

Architectures. Various embodiments may implement one or more of five different landmark localization methods for catheter tracking from X-ray fluoroscopy of 3D printed heart phantoms. Different assemblies of CNNs and FCN networks may be employed, and performances compared during both training and inference. FIG. 22 shows the architectures of potential networks for different assemblies of CNNs and FCNs. A desirable property of a system that is able to reason about images is to disentangle object pose and part deformation from texture and shape. In various embodiments, the introduction of local max-pooling layers in CNNs has helped to satisfy this property by allowing a network to be somewhat spatially invariant to the position of features. As a result, each model's performance was assessed upon implementing more max-pooling layers in CNNs, illustrated as Model A, B in FIG. 21.

As opposed to the heatmap matching approach, FCN allows end-to-end backpropagation from the predicted numerical coordinates to the input image. Therefore, to highlight the high dependency of the fully connected layer weights on the spatial distribution of the inputs during training, the FCN architectures were trained on different datasets with various distributions of groundtruth and the results compared.

Figure 24A:
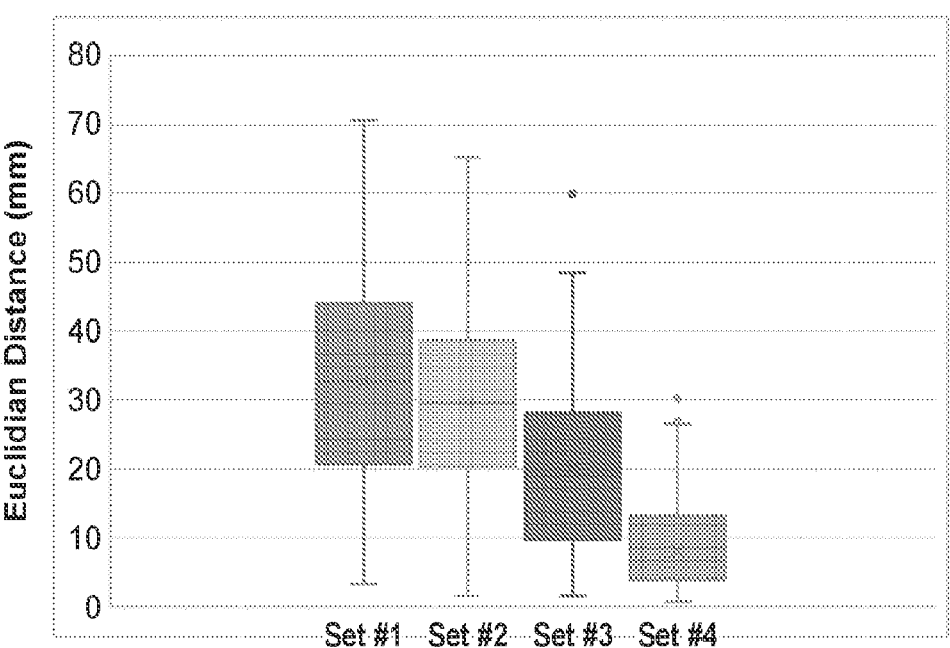
FIGS. 24A-24C depict Model B performance according to various potential embodiments.
Figure 24B:
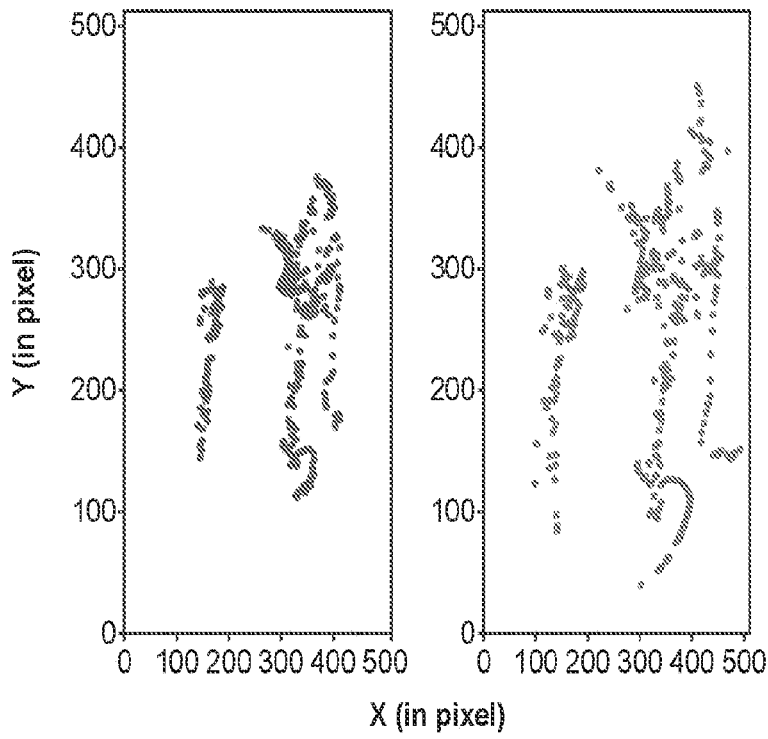
Figure 24C:
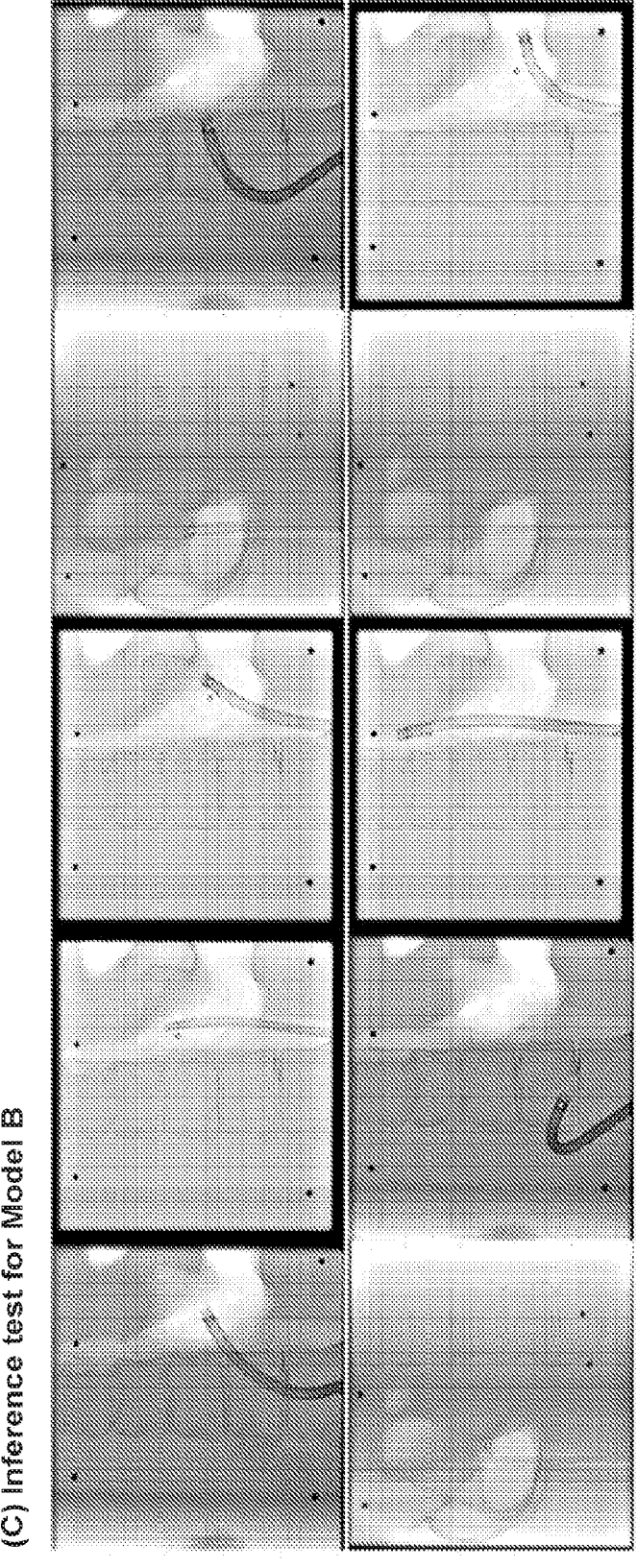
Figure 25A:
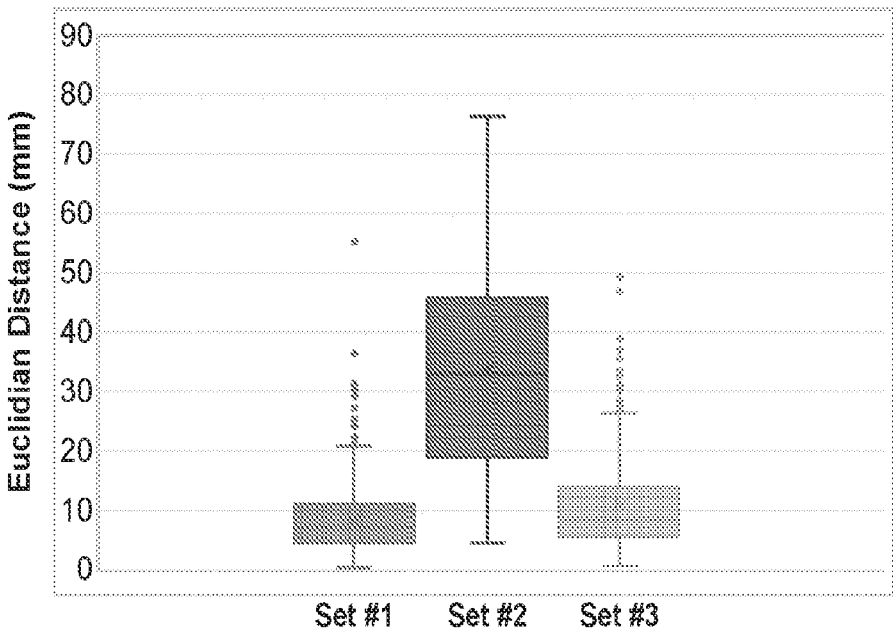
FIGS. 25A-25C depict Model C performance according to various potential embodiments.
Figure 25B:
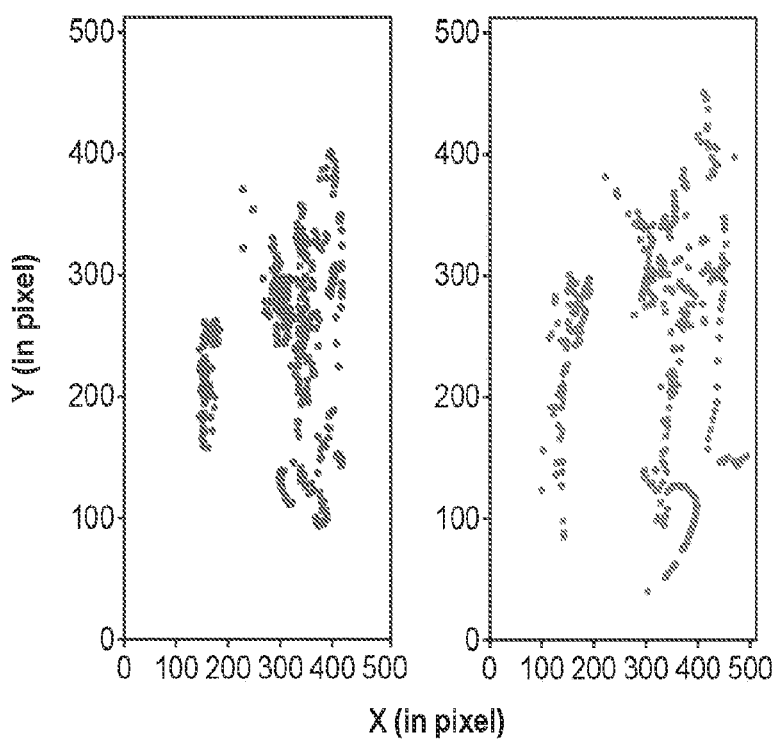
Figure 25C:
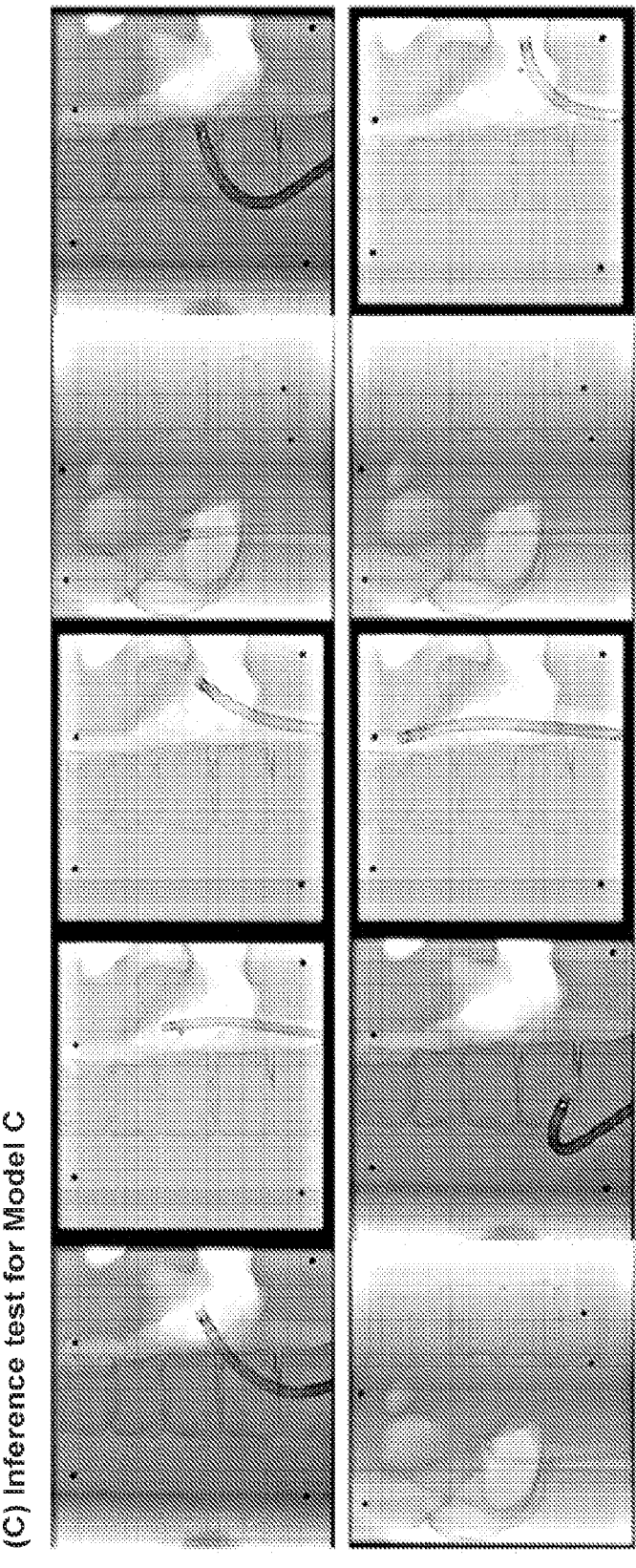

FIGS. 23, 24, 25 correspond to Model A (see Table 2), Model B (see Table 3), and Model C (see Table 4) performance, respectively.

Figure 23A:
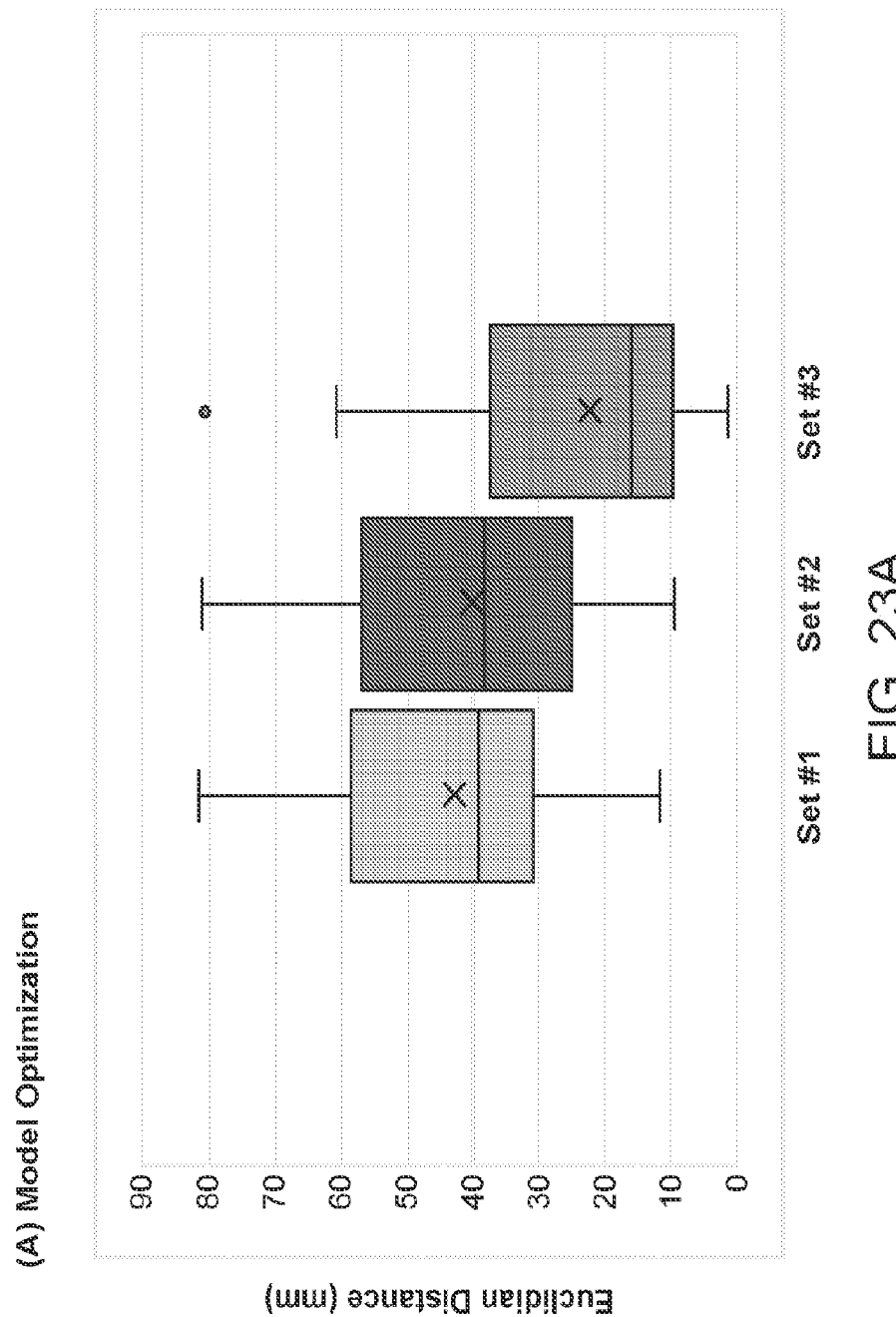
FIGS. 23A-23C depict Model A performance according to various potential embodiments.
Figure 23B:
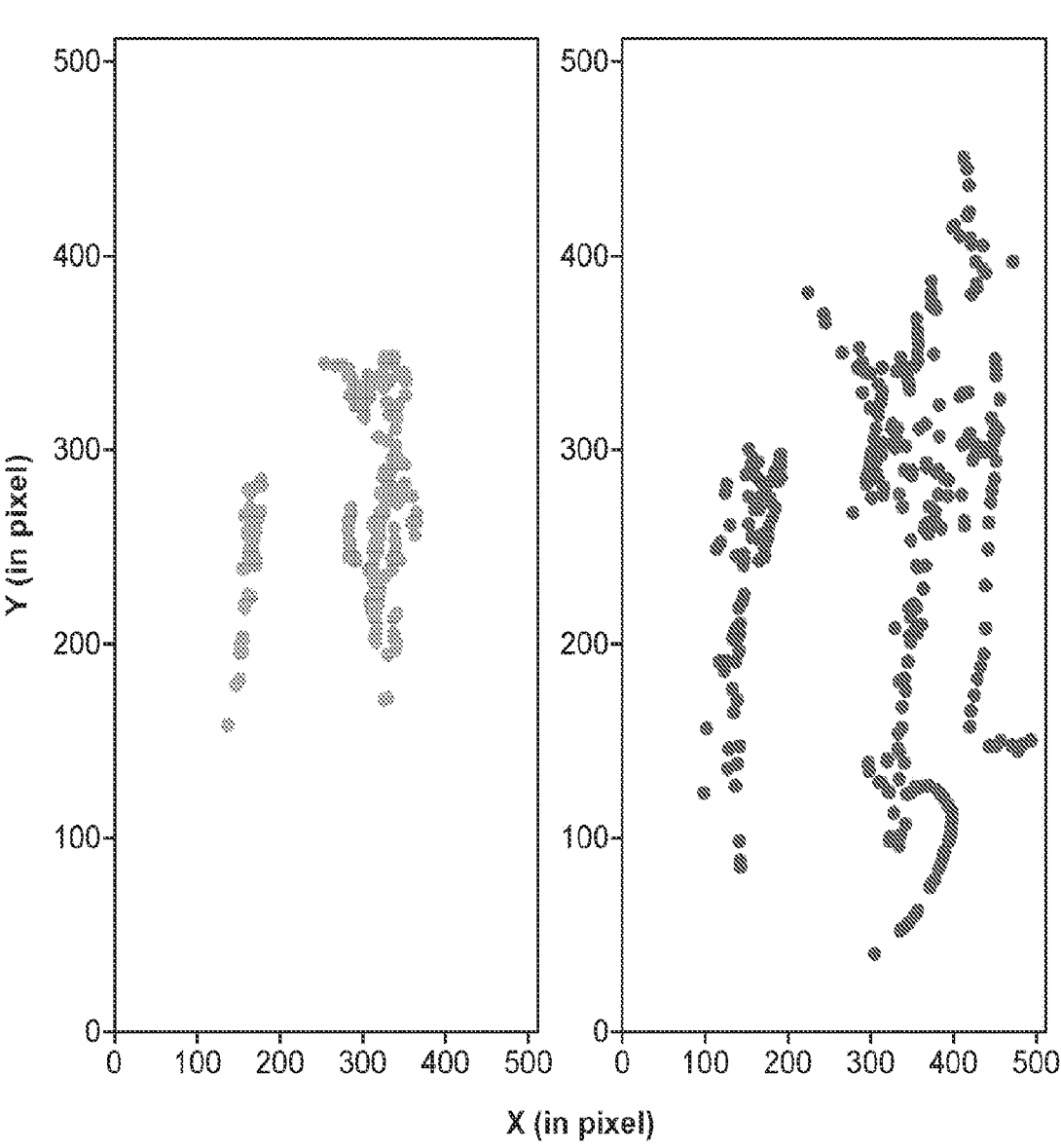
Figure 23C:
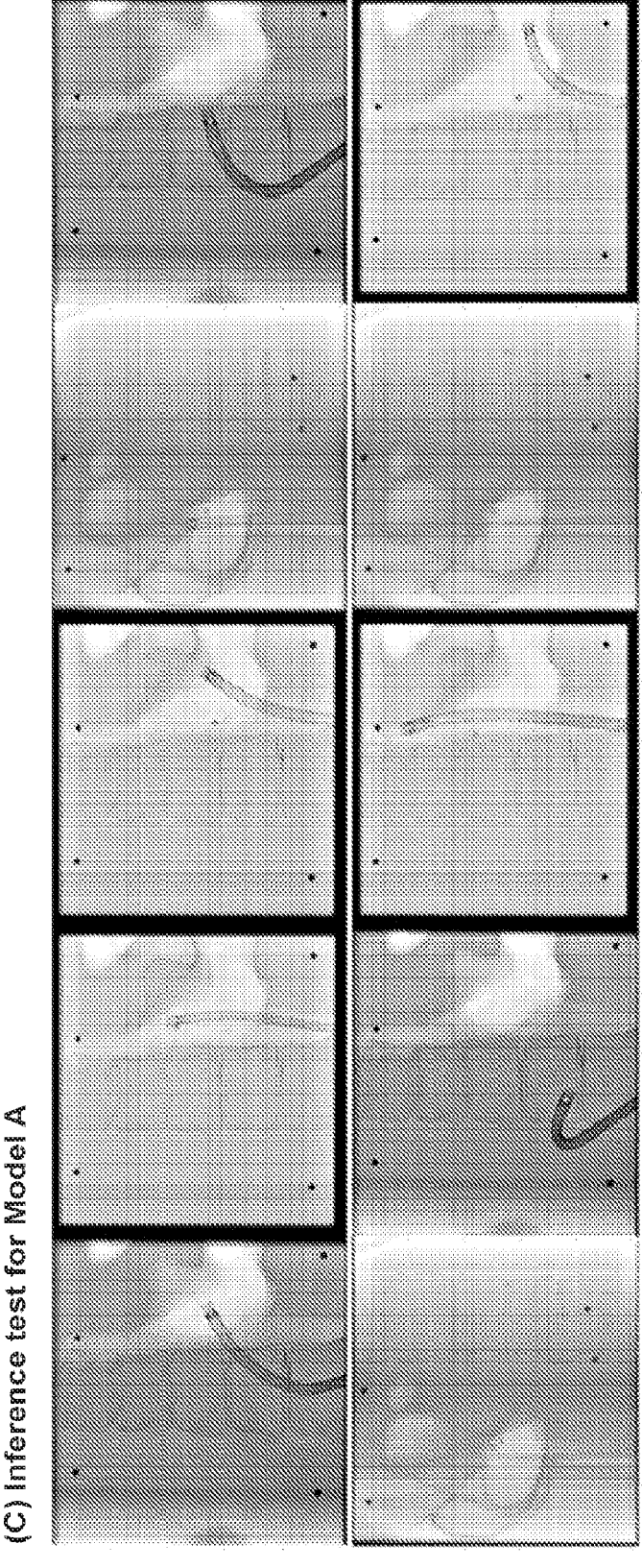

In various embodiments, all three model architectures proposed for the 'Cony+FCN' method were optimized for the lowest Euclidean distance error on the test dataset. The summary of the hyperparameter optimization for each model can be found in Tables 2-4 (see below and FIGS. 26A-26C). FIG. 23A shows the comparison of the performance for Model A, and recognized the optimized set for the hyperparameters. Similarly, the performance comparison was conducted to optimize Models B and C, and compare the Euclidian distance error on the test dataset, shown in FIG. 24A and FIG. 25A, respectively. As can be seen, the optimized model B has shown the lowest Euclidean distance error on the test dataset. Additionally, the spatial invariancy of the models were compared and illustrated in FIGS. 23B, 24B, and 25B where it depicts the effect of spatial distribution of groundtruth during training, suggesting the high dependency of the fully connected layer weights on the spatial distribution of the inputs during training. Lastly, the performance of each optimized model was visualized and compared in FIG. 23C, FIG. 24C, and FIG. 25C.

TABLE 2

The summary of hyperparameters optimization for Model A.

| Hyperparameter | Learning rate | Batch size | Epochs number | Augmentation | Total size |
|---|---|---|---|---|---|
| Set # 1 | 1e−3 | 32 | 80 | False | 529 images |
| Set # 2 | 1e−3 | 32 | 110 | False | 529 images |
| Set # 3 | 7e−4 | 32 | 250 | True* | 1058 images |

TABLE 3

The summary of hyperparameters optimization for Model B.

| Hyperparameter | Learning rate | Batch size | Epochs number | Augmentation | Total size |
|---|---|---|---|---|---|
| Set # 1 | 5e−4 | 32 | 190 | True* (2x) | 1058 images |
| Set # 2 | 7e−4 | 32 | 200 | True* (3x) | 1587 images |
| Set # 3 | 7e−4 | 32 | 200 | 10-fold** | 2116 images |
| Set # 4 | 7e−4 | 32 | 250 | True* (4x) | 2116 images |

TABLE 4

The summary of hyperparameters optimization for Model C.

| Hyperparameter | Learning rate | Batch size | Epochs number | Augmentation | Total size |
|---|---|---|---|---|---|
| Set # 1 | 1e−2, decay = 1e−3, rate = 0.9 | 32 | 150 | True* (6x) | 3408 images |
| Set # 2 | 1e−2, decay = 1e−3, rate = 0.9 | 32 | 200 | True* (6x) | 3408 images |
| Set # 3 | 1e−2, | 32 | 200 | True* (6x) | 3408 |

TABLE 4-continued

The summary of hyperparameters optimization for Model C.

| Hyperparameter | Learning rate | Batch size | Epochs number | Augmentation | Total size |
|---|---|---|---|---|---|
| | decay = 1e−5, rate = 0.3 | | | | images |

Figure 27:
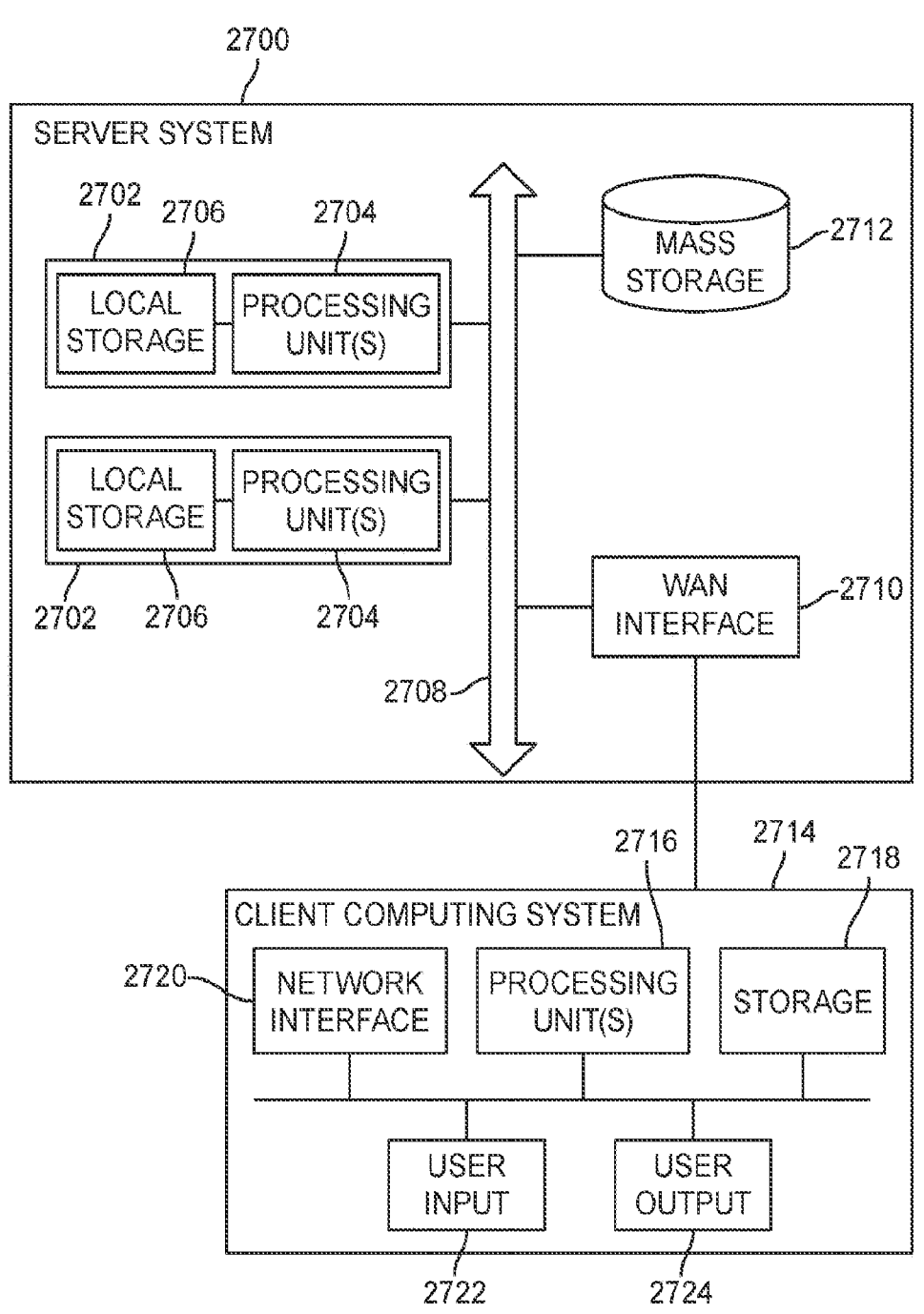
FIG. 27 shows a simplified block diagram of a representative server system and client computer system usable to implement certain embodiments of the present disclosure.

Various operations described herein can be implemented on computer systems having various design features. FIG. 27 shows a simplified block diagram of a representative server system 2700 (e.g., guidance system 102 in FIG. 1, catheterization lab personal computer (Cath Lab PC) of FIG. 12, and/or research laptop of FIG. 12) and client computer system 2714 (e.g., guidance system 102, first imaging device 104, second imaging device 106, sensors 108, video grabber of FIG. 12, and/or MR headset of FIG. 12) usable to implement certain embodiments of the present disclosure. In various embodiments, server system 2700 or similar systems can implement services or servers described herein or portions thereof. Client computer system 2714 or similar systems can implement clients described herein.

Server system 2700 can have a modular design that incorporates a number of modules 2702 (e.g., blades in a blade server embodiment); while two modules 2702 are shown, any number can be provided. Each module 2702 can include processing unit(s) 2704 and local storage 2706.

Processing unit(s) 2704 can include a single processor, which can have one or more cores, or multiple processors. In some embodiments, processing unit(s) 2704 can include a general-purpose primary processor as well as one or more special-purpose co-processors such as graphics processors, digital signal processors, or the like. In some embodiments, some or all processing units 2704 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 2704 can execute instructions stored in local storage 2706. Any type of processors in any combination can be included in processing unit(s) 2704.

Local storage 2706 can include volatile storage media (e.g., conventional DRAM, SRAM, SDRAM, or the like) and/or non-volatile storage media (e.g., magnetic or optical disk, flash memory, or the like). Storage media incorporated in local storage 2706 can be fixed, removable or upgradeable as desired. Local storage 2706 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 2704 need at runtime. The ROM can store static data and instructions that are needed by processing unit(s) 2704. The permanent storage device can be a non-volatile read-and-write memory device that can store instructions and data even when module 2702 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

Figure 1:
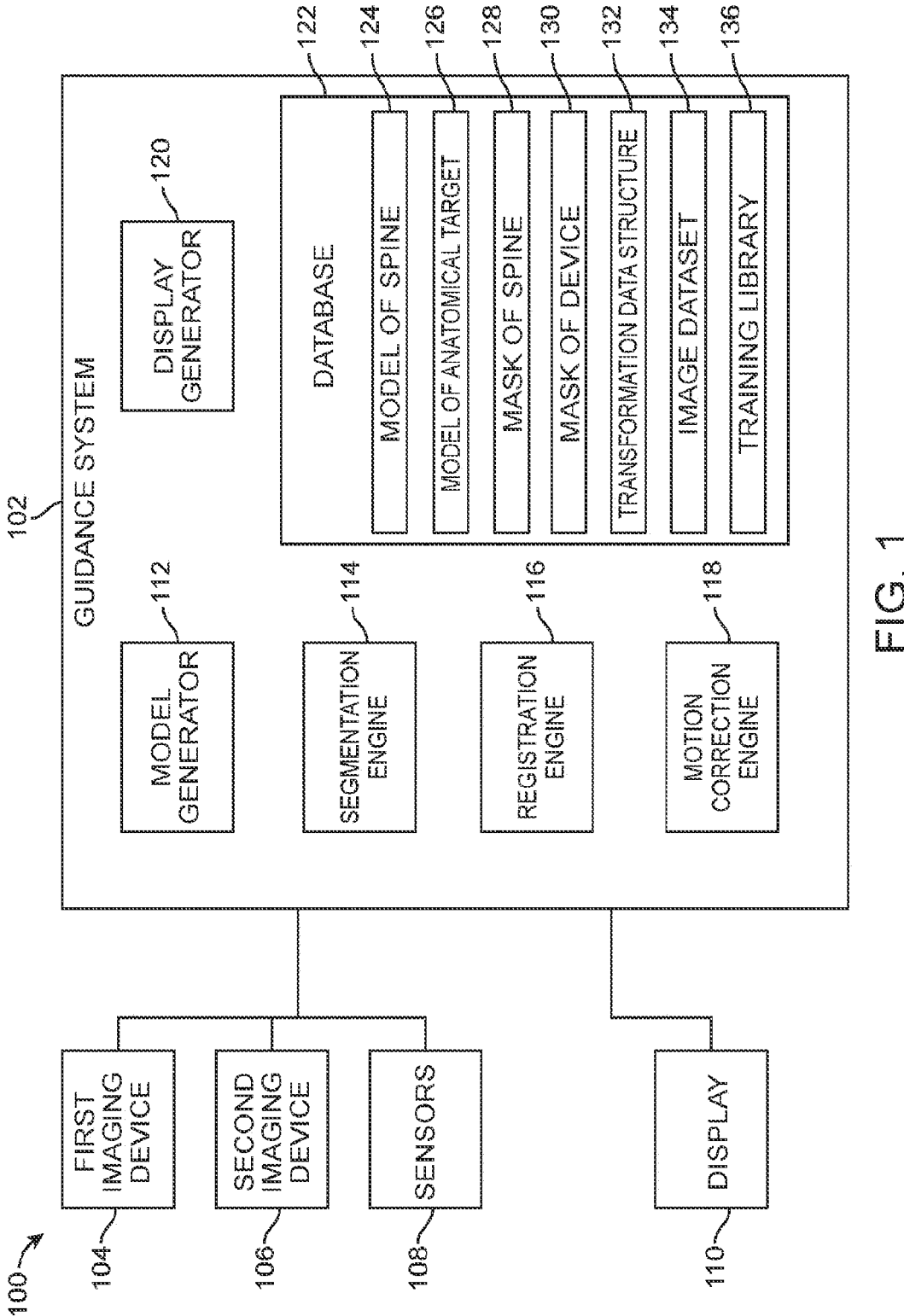
FIG. 1 illustrates an example system to guide the placement of medical devices, according to various potential embodiments.

In some embodiments, local storage 2706 can store one or more software programs to be executed by processing unit(s) 2704, such as an operating system and/or programs implementing various server functions or computing functions, such as any functions of any components of FIGS. 1 and 12 or any other computing device, computing system, and/or sensor identified in this disclosure.

"Software" refers generally to sequences of instructions that, when executed by processing unit(s) 2704 cause server system 2700 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 2704. Software can be implemented as a single program or a collection of separate programs or program modules that interact as desired. From local storage 2706 (or non-local storage described below), processing unit(s) 2704 can retrieve program instructions to execute and data to process in order to execute various operations described above.

In some server systems 2700, multiple modules 2702 can be interconnected via a bus or other interconnect 2708, forming a local area network that supports communication between modules 2702 and other components of server system 2700. Interconnect 2708 can be implemented using various technologies including server racks, hubs, routers, etc.

A wide area network (WAN) interface 2710 can provide data communication capability between the local area network (interconnect 2708) and a larger network, such as the Internet. Conventional or other activities technologies can be used, including wired (e.g., Ethernet, IEEE 802.3 standards) and/or wireless technologies (e.g., Wi-Fi, IEEE 802.11 standards).

In some embodiments, local storage 2706 is intended to provide working memory for processing unit(s) 2704, providing fast access to programs and/or data to be processed while reducing traffic on interconnect 2708. Storage for larger quantities of data can be provided on the local area network by one or more mass storage subsystems 2712 that can be connected to interconnect 2708. Mass storage subsystem 2712 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 2712. In some embodiments, additional data storage resources may be accessible via WAN interface 2710 (potentially with increased latency).

Server system 2700 can operate in response to requests received via WAN interface 2710. For example, one of modules 2702 can implement a supervisory function and assign discrete tasks to other modules 2702 in response to received requests. Conventional work allocation techniques can be used. As requests are processed, results can be returned to the requester via WAN interface 2710. Such operation can generally be automated. Further, in some embodiments, WAN interface 2710 can connect multiple server systems 2700 to each other, providing scalable systems capable of managing high volumes of activity. Conventional or other techniques for managing server systems and server farms (collections of server systems that cooperate) can be used, including dynamic resource allocation and reallocation.

Server system 2700 can interact with various user-owned or user-operated devices via a wide-area network such as the Internet. An example of a user-operated device is shown in FIG. 27 as client computing system 2714. Client computing system 2714 can be implemented, for example, as a consumer device such as a smartphone, other mobile phone, tablet computer, wearable computing device (e.g., smart watch, eyeglasses), desktop computer, laptop computer, and so on.

For example, client computing system 2714 can communicate via WAN interface 2710. Client computing system 2714 can include conventional computer components such as processing unit(s) 2716, storage device 2718, network interface 2720, user input device 2722, and user output device 2724. Client computing system 2714 can be a computing device implemented in a variety of form factors, such as a desktop computer, laptop computer, tablet computer, smartphone, other mobile computing device, wearable computing device, or the like.

Processor 2716 and storage device 2718 can be similar to processing unit(s) 2704 and local storage 2706 described above. Suitable devices can be selected based on the demands to be placed on client computing system 2714; for example, client computing system 2714 can be implemented as a "thin" client with limited processing capability or as a high-powered computing device. Client computing system 2714 can be provisioned with program code executable by processing unit(s) 2716 to enable various interactions with server system 2700 of a message management service such as accessing messages, performing actions on messages, and other interactions described above. Some client computing systems 2714 can also interact with a messaging service independently of the message management service.

Network interface 2720 can provide a connection to a wide area network (e.g., the Internet) to which WAN interface 2710 of server system 2700 is also connected. In various embodiments, network interface 2720 can include a wired interface (e.g., Ethernet) and/or a wireless interface implementing various RF data communication standards such as Wi-Fi, Bluetooth, or cellular data network standards (e.g., 3G, 4G, LTE, 5G, etc.).

User input device 2722 can include any device (or devices) via which a user can provide signals to client computing system 2714; client computing system 2714 can interpret the signals as indicative of particular user requests or information. In various embodiments, user input device 2722 can include any or all of a keyboard, touch pad, touch screen, mouse or other pointing device, scroll wheel, click wheel, dial, button, switch, keypad, microphone, and so on.

User output device 2724 can include any device via which client computing system 2714 can provide information to a user. For example, user output device 2724 can include a display to display images generated by or delivered to client computing system 2714. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 2724 can be provided in addition to or instead of a display. Examples include indicator lights, speakers, tactile "display" devices, printers, haptic devices (e.g., tactile sensory devices may vibrate at different rates or intensities with varying timing), and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 2704 and 2716 can provide various functionality for server system 2700 and client computing system 2714, including any of the functionality described herein as being performed by a server or client, or other functionality associated with message management services.

It will be appreciated that server system 2700 and client computing system 2714 are illustrative and that variations and modifications are possible. Computer systems used in connection with embodiments of the present disclosure can have other capabilities not specifically described here. Further, while server system 2700 and client computing system 2714 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

Various details and features discussed above may find additional support and discussion in the following publications:

[1] Torabinia, M., Caprio, A., Jang, S. J., Ma, T., Tran, H., Mekki, L., . . . & Mosadegh, B. (2021). Deep learning-driven catheter tracking from bi-plane X-ray fluoroscopy of 3D printed heart phantoms. Mini-invasive Surgery, 5.

[2] Sra J, Krum D, Choudhuri I, Belanger B, Palma M, Brodnick D, Rowe D B. Identifying the third dimension in 2D fluoroscopy to create 3D cardiac maps. JCI Insight. 2016; 1(21):e90453. doi: 10.1172/jci.insight.90453. PubMed PMID: 28018976; PMCID: PMC5161213 D. Krum and I. Choudhuri are consultants of APN Health. B. Belanger, M. Palma, D. Brodnick, and D. Rowe are contract employees of APN Health.

[3] Fallavollita P. Is single-view fluoroscopy sufficient in guiding cardiac ablation procedures? Int J Biomed Imaging. 2010; 2010:631264. doi: 10.1155/2010/631264. PubMed PMID: 20368770; PMCID: PMC2846336.

[4] Ronneberger O, Fischer P, Brox T, editors. U-net: Convolutional networks for biomedical image segmentation. International Conference on Medical image computing and computer-assisted intervention; 2015: Springer.

[5] Liu J, Al'Aref S J, Singh G, Caprio A, Moghadam A A A, Jang S-J, Wong S C, Min J K, Dunham S, Mosadegh B. An augmented reality system for image guidance of transcatheter procedures for structural heart disease. PLOS ONE. 2019; 14(7):e0219174. doi: 10.1371/journal.pone.0219174.

[6] Desjardins B, Kazerooni E A. ECG-gated cardiac CT. AJR Am J Roentgenol. 2004; 182(4):993-1010. Epub 2004/03/25. doi: 10.2214/ajr.182.4.1820993. PubMed PMID: 15039178.

[7] Buther F, Dawood M, Stegger L, Wubbeling F, Schafers M, Schober O, Schafers K P. List mode-driven cardiac and respiratory gating in PET. J Nucl Med. 2009; 50(5): 674-81. Epub 2009/04/18. doi: 10.2967/jnumed.108.059204. PubMed PMID: 19372491.

[8] Koivumaki T, Nekolla S G, Furst S, Loher S, Vauhkonen M, Schwaiger M, Hakulinen M A. An integrated bio-impedance—ECG gating technique for respiratory and cardiac motion compensation in cardiac PET. Phys Med Biol. 2014; 59(21):6373-85. Epub 2014/10/09. doi: 10.1088/0031-9155/59/21/6373. PubMed PMID: 25295531.

[9] Jang S-J, Torabinia M, Dhrif H, Caprio A, Liu J, Wong S C, Mosadegh B. Development of a Hybrid Training Simulator for Structural Heart Disease Interventions. Advanced Intelligent Systems. 2020; 2(12):2000109.

Non-limiting examples of various embodiments are disclosed herein. Features from one embodiments disclosed herein may be combined with features of another embodiment disclosed herein as someone of ordinary skill in the art would understand. The foregoing description is illustrative only and is not intended to be in any way limiting. Further non-limiting aspects and features of various potential embodiments are found in the images and supplemental materials in the Appendix. This disclosure also incorporates by reference PCT application WO2019/165430, attached hereto.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method of providing real-time image guidance and/or navigation for a medical procedure, comprising:
   receiving a first image data set of an anatomical target in relation to at least one fiducial marker in a selected coordinate system;
   generating a 3D model of the anatomical target, in relation to the first image data set and the at least one fiducial marker, in the selected coordinate system;
   receiving at least one single-plane fluoroscopic image comprising the at least one fiducial marker and a medical device;
   generating a mask or a center coordinate of the at least one fiducial marker from the at least one single-plane fluoroscopic image;
   generating a 3D model of the medical device from the at least one single-plane fluoroscopic image in the selected coordinate system by performing feature extraction on the medical device and the at least one fiducial marker, and using a trained machine learning model to infer, based on extracted features, a z-position of at least one portion of the medical device;
   registering the 3D model of the medical device with the 3D model of the anatomical target in the selected coordinate system; and
   generating a real-time output image comprising the 3D model of the medical device registered with a geometry of the anatomical target in the selected coordinate system.

2. The method of claim 1, wherein the first image data set comprises preoperative images, images acquired during the medical procedure, or images acquired both preoperatively and during the medical procedure.

3. The method of claim 1, wherein the at least one fiducial marker is visible in both an act of receiving the first image data set of the anatomical target and the act of receiving the at least one single-plane fluoroscopic image comprising the medical device.

4. The method of claim 1, wherein the first image data comprises at least one of fluoroscopy data, echocardiography data, computed tomography (CT) data, or magnetic resonance (MR) data.

5. The method of claim 1, wherein the at least one fiducial marker comprises at least one first fiducial marker internal to a subject and at least one second fiducial marker external to the subject.

6. The method of claim 1, wherein the feature extraction comprises edge detection of a dimension of at least a portion of the medical device or a dimension of a fiducial marker borne by the medical device.

7. The method of claim 1, wherein the feature extraction comprises edge detection of a rotational position of at least a portion of the medical device or a rotational position of the fiducial marker borne by the medical device relative to one or more axes.

8. The method of claim 1, wherein the generating the 3D model of the medical device comprises determining at least one of a rotation angle, a translation, or a scaling factor based on a projection of the at least one fiducial marker in the at least one single-plane fluoroscopic image.

9. The method of claim 1, further comprising outputting a haptic output to a haptic device responsive to a predefined proximity of at least a portion of the 3D model of the medical device to a predetermined portion of the 3D model of the anatomical target in the selected coordinate system.

10. The method of claim 1, wherein the registering of the 3D model of the medical device with the 3D model of the anatomical target in the selected coordinate system comprises registering respiratory motion, cardiac motion, or both respiratory motion and cardiac motion, at least in part by processing image data, as between the first image data set and the received at least one single-plane fluoroscopic image, having a same phase of motion.

11. The method of claim 1, further comprising outputting the real-time output image to a display device, wherein the display device comprises a virtual reality (VR) headset, an augmented reality (AR) headset, a mixed reality (MR) headset, a wearable device comprising a heads-up-display, or an area display.

12. The method of claim 1, wherein the generating of the real-time output image yields quantitative feedback of z-axis position of at least a portion of the medical device relative to the anatomical target or another anatomical feature with an accuracy ranging from 0.1 mm to 5 mm and a precision of about 10 μm to 1 mm.

13. The method of claim 12, further comprising outputting the quantitative feedback to a device providing auditory, visual or tactile guidance for open-loop instruction to an interventionalist.

14. The method of claim 12, further comprising outputting the quantitative feedback as a closed-loop instruction to a robotic controller of the medical device.

15. A system for image guidance comprising:
one or more processors; and
a non-transitory memory device storing processor executable instructions to cause the one or more processors, upon execution of the executable instructions, to:
receive a first image data set of an anatomical target in relation to at least one fiducial marker in a selected coordinate system;

generate a 3D model of the anatomical target, in relation to the first image data set and the at least one fiducial marker, in the selected coordinate system;
receive at least one single-plane fluoroscopic image comprising the at least one fiducial marker and a medical device;
generate a mask of the at least one fiducial marker from the at least one single-plane fluoroscopic image;
generate a 3D model of the medical device from the at least one single-plane fluoroscopic image in the selected coordinate system by performing feature extraction on the medical device and the at least one fiducial marker, and using a trained deep learning model to infer, based on extracted features, a z-position of at least one portion of the medical device;
register the 3D model of the medical device with the 3D model of the anatomical target in the selected coordinate system; and
generate a real-time output image comprising the 3D model of the medical device registered with a geometry of the anatomical target in the selected coordinate system.

16. The system of claim 15, wherein the first image data set comprises images acquired both preoperatively and during a medical procedure.

17. The system of claim 15, further comprising a haptic device, wherein the executable instructions stored on the non-transitory memory device cause the one or more processors, upon execution of the executable instructions, to output a haptic output to the haptic device responsive to a predefined proximity of at least a portion of the 3D model of the medical device to a predetermined portion of the 3D model of the anatomical target in the selected coordinate system.

18. The system of claim 15, further comprising a display device, the display device including a virtual reality (VR) headset, an augmented reality (AR) headset, a mixed reality (MR) headset, a wearable device comprising a heads-up-display, or an area display, wherein the executable instructions stored on the non-transitory memory device cause the one or more processors, upon execution of the executable instructions, to output the real-time output image to the display device.

19. The system of claim 15, further comprising:
a device providing auditory, visual and/or tactile guidance for open-loop instruction to an interventionalist,
wherein the executable instructions stored on the non-transitory memory device cause the one or more processors, upon execution of the executable instructions, to output quantitative feedback of z-axis position of at least a portion of the medical device relative to the anatomical target or another anatomical feature to the device to provide guidance for open-loop instruction to the interventionalist.

20. The system of claim 15, further comprising a robotic controller and a robot comprising an end effector to control the medical device,
wherein the executable instructions stored on the non-transitory memory device cause the one or more processors, upon execution of the executable instructions, to output quantitative feedback of z-axis position of at least a portion of the medical device relative to the anatomical target or another anatomical feature as a closed-loop instruction to the robotic controller to cause the robot to move the end effector controlling the medical device to cause a related movement of the medical device.

* * * * *